United States Patent [19]
Weiner et al.

[11] Patent Number: 5,817,637
[45] Date of Patent: *Oct. 6, 1998

[54] GENETIC IMMUNIZATION

[75] Inventors: David B. Weiner, Merion; William V. Williams; Bin Wang, both of Havertown, all of Pa.

[73] Assignees: The Trustees of the University of Pennsylvania; The Wistar Institute, both of Philadelphia, Pa.

[ * ] Notice: The term of this patent shall not extend beyond the expiration date of Pat. No. 5,593,972.

[21] Appl. No.: 783,818

[22] Filed: Jan. 13, 1997

Related U.S. Application Data

[63] Continuation of Ser. No. 125,012, Sep. 21, 1993, Pat. No. 5,593,972, which is a continuation-in-part of Ser. No. 29,336, Mar. 11, 1993, abandoned, which is a continuation-in-part of Ser. No. 8,342, Jan. 26, 1993, abandoned.

[51] Int. Cl.$^6$ .......................... A61K 45/05; A61K 48/00; A61K 31/00
[52] U.S. Cl. .......................... 514/44; 424/278.1; 435/975; 514/44; 514/615; 514/818
[58] Field of Search ............................ 514/44, 615, 818; 424/278.1; 435/975

[56] References Cited

U.S. PATENT DOCUMENTS

| | | | |
|---|---|---|---|
| 4,224,404 | 9/1980 | Viza et al. | 435/2 |
| 4,394,448 | 7/1983 | Szoka, Jr. et al. | 435/172.3 |
| 4,806,463 | 2/1989 | Goodchild et al. | 435/5 |
| 4,945,050 | 7/1990 | Sanford et al. | 435/172.1 |
| 5,017,487 | 5/1991 | Stunnenberg et al. | 435/172.3 |
| 5,036,006 | 7/1991 | Sanford et al. | 435/170.1 |
| 5,185,254 | 2/1993 | Linnenbach | 435/172.3 |
| 5,466,676 | 11/1995 | Booth et al. | 514/44 |
| 5,593,972 | 1/1997 | Weiner et al. | 514/44 |

FOREIGN PATENT DOCUMENTS

| | | |
|---|---|---|
| WO 90/11092 | 10/1990 | WIPO . |
| WO 91/12329 | 8/1991 | WIPO . |
| WO 93/17706 | 9/1993 | WIPO . |
| WO 93/23552 | 11/1993 | WIPO . |

OTHER PUBLICATIONS

Waisman et al., Nature Medicine 2(8):899–905 (1996).
Tanuma et al., Cellular Immunology 168:85–90 (1996).
Acsadi et al., "Human dystrophin expression in mdx mice after intramuscular injection of DNA constructs," *Nature* 352:815–818, 1991.
Anderson, W. French, "Prospects for Human Gene Therapy," *Science* 226:401–409, 1984.
Anilionis et al., "Structure of the glycoprotein gene in rabies virus," *Nature* 294:275278, 1981.
Benoit et al., "Destruction and regeneration of skeletal muscle after treatment with a local anaesthetic, bupivacaine (Marcaine®)," *J. Anat.* 107:547–556, 1970.
Berman eta l., "Protection of chimpanzees from infection by HIV–1 after vaccination with recombinant glycoprotein gp120 but not gp160," *Nature*, 345:622–625, 1990.

Brigham et al., "Rapid Communication: In Vivo Transfection of Murine Lungs with a Functioning Prokaryotic Gene Using a Liposome Vehicle," *American Journal of the Medical Sciences*, 298:278–281, 1989.
Chaudhary et al., "A rapid method of cloning functional variable–region antibody genes in *Escherichia coli* as single–chain immunotoxins," *Proc. Natl. Acad. Sci. USA*, 87:1066–1070, 1990.
Chen et al.,"HIV–1 gp41 contains two sites for interaction with several proteins on the helper T–lymphoid cell line, H9," *AIDS*, 6:533–539, 1992.
Cheng–Mayer et al., "Human Immunodeficiency virus can productively infect cultured human glial cells," *Proc. Natl. Acad. Sci. USA*,84:3526–3530, 1987.
Crowe et al., Improved cloning efficiency of polymerase chain reaction (PCR) products after proteinase K digestion, *Nucleic Acids Research*, 19:184, 1991.
Desquenne–Clark et al., "T–cell receptor peptide immunization leads to enhanced and chronic experimental allergic encephalomyelitis," *Proc. Natl. Acad. Sci. USA*, 88:7219–7223, 1991.
Di Fiore et al., "erbB–2 Is a Potent Oncogene When Overexpressed in NIH/3T3 Cells," *Science*, 237:178–182, 1987.
Dubensky et al., "Direct transfection of viral and plasmid DNA into the liver of spleen of mice," *Proc. Natl. Acad. Sci. USA*, 81:7529–7533, 1984.
Felgner et al., "Gene Therapeutics," *Nature*, 349:351–352, 1991.
Fisher et al., "A molecular clone of HTLV–III with biological activity," *Nature*, 316:262–265, 1985.
Fisher et al., "HIV infection is blocked in vitro by recombinant soluble CD4," *Nature*, 331:76–78, 1988.
Goudsmit et al., "Human antibody response to a strain–specific HIV–1 gp120 epitope associated with cell fusion inhibition," *AIDS*, 2:157–164, 1988.

(List continued on next page.)

*Primary Examiner*—Johnny F. Railey, II
*Attorney, Agent, or Firm*—Woodcock Washburn Kurtz Mackiewicz & Norris LLP

[57] ABSTRACT

Methods of prophylactic and therapeutic immunization of an individual against pathogen infection, diseases associated with hyperproliferative cells and autoimmune diseases are disclosed. The methods comprise the steps of administering to cells of an individual, a nucleic acid molecule that comprises a nucleotide sequence that encodes a protein which comprises at least one epitope that is identical or substantially similar to an epitope of a pathogen antigen, a hyperproliferative cell associated protein or a protein associated with autoimmune disease respectively. In each case, nucleotide sequence is operably linked to regulatory sequences to enable expression in the cells. The nucleic acid molecule is free of viral particles and capable of being expressed in said cells. The cells may be contacted cells with a cell stimulating agent. Methods of prophylactically and therapeutically immunizing an individual against HIV are disclosed. Pharmaceutical compositions and kits for practicing methods of the present invention are disclosed.

34 Claims, 12 Drawing Sheets

OTHER PUBLICATIONS

Hah et al., "Suppression of Murine Lupus Nephritis By Administration of an Anti–Idiotypic Antibody to Anti–DNA," *J. of Immunology*, 132:187–190, 1984.

Hall–Craggs, E.C.B., "Rapid Degeneration and Regeneration of a Whole Skeletal Muscle Following Treatment with Bupivacain (Marcain)," *Experimental Neurology*, 43:349–358, 1974.

Howley, Peter M., "Papillomavirinae and Their Replication," *Virology*, Chapter 58:1625–1650, 1990.

Howell et al., "Limited T–cell receptor Beta–chain heterogeneity among interleukin 2 receptor–positive synovial T cells suggests a role for superantigen in rheumatoid arthritis," *Proc. Natl. Acad. Sci. USA*, 88:10921–10925, 1991.

Israel et al., "Biological Activity of Polyoma Viral DNA in Mice and Hamsters," *J. of Virology*, 29:990–996, 1979.

Klein et al., "Transformation of Microbes, Plants and Animals by Particle Bombardment," *Bio/Technology*, 10:286–291, 1992.

Koenig et al., "Detection of AIDS Virus in Macrophages in Brain Tissue from AIDS Patients with Encephalopathy," *Science*, 233:1089–1093, 1986.

Kowalski et al., "Functional Regions of the Envelope Glycoprotein of Human Immunodeficiency Virus Type 1," *Science*, 237:1351–1355, 1987.

Langlois et al., "The Ability of Certain HIV Vaccines to Provoke Reactions Against Normal Cells," *Science*, 255:292–293, 1992.

Lasky et al., "Neutralization of the AIDS Retrovirus by Antibodies to a Recombinant Envelope Glycoprotein," *Science*, 233:209–212, 1986.

Lasky et al., "Delineation of a Region of the Human Immunodeficiency Virus Type 1 gp120 Glycoprotein Critical for Interaction with the CD4 Receptor," *Cell*, 50:975–985, 1987.

Letvin et al., "Risks of Handling HIV," *Nature*, 349:573, 1991.

Maddon et al., "The T4 Gene Encodes the AIDS Virus Receptor and Is Expressed in the Immune System and the Brain," *Cell*, 47:333–348, 1986.

Montefiori et al., "Evaluation of Antiviral Drugs and Neutralizing Antibodies to Human Immunodeficiency Virus by a Rapid and Sensitive Microtiter Infection Assay," *J. of Clinical Microbiology*, 26:231–235, 1988.

Morgenstern et al., "Advanced mammalian gene transfer: high titre retroviral vectors with multiple drug selection markers and a complementary helper–free packaging cell line," *Nucl. Acids Res.*, 18:3587–3596, 1990.

Nabel et al., "Site–Specific Gene Expression in Vivo by Direct Gene Transfer into the Arterial Wall," *Science*, 249:1285–1288, 1990.

Nara, Peter L., "Quantitative Infectivity Syncytium–Forming Microassay," *Basic Virologic Techniques*, 77–86.

Oksenberg et al., "Limited heterogeneity of rearranged T–cell receptor V alpha transcripts in brains of multiple sclerosis patients," *Nature*, 345:344–348, 1990.

Osther et al., "Protective Humoral Immune Responses to the Human Immunodeficiency Virus Induced in Immunized Pigs: A Possible Soure of Therapeutic Immunoglobulin Preparations," *Hybridoma*, 10:673–683, 1991.

Osther et al., "The Quick Western Blot, A Novel Transportable 50–Minute HIV–1 Antibody Test," *Transplantation*, 47:834–838, 1989.

Paliard et al., "Evidence for the Effects of a Superantigen in Rheumatoid Arthritis," *Science*, 253:325–329, 1991.

Putney et al., "Development of an HIV Subunit Vaccine," *V International Conference on AIDS*, Quebec, Canada; Jun. 4–9, 1989.

Schrier et al., "B–and T–Lymphocyte Responses to an Immunodominant Epitope of Human Immunodeficiency Virus," *J. of Virology*, 62:2531–2536, 1988.

Sun et al., "Generation and Characterization of Monoclonal Antibodies to the Putative CD4–Binding Domain of Human Immunodeficiency Virus Type 1 gp120," *J. of Virology*, 63:3579–3585, 1989.

Shah et al., "Papillomaviruses," *Virology*, Chapter 59:1651–1676, 1990.

Seed et al., "Molecular cloning of the CD2 antigen, the T–cell erythrocyte receptor, by a rapid immunoselection procedure," *Proc. Natl. Acad. Sci. USA*, 84:3365–3369, 1987.

Szala et al., "Molecular cloning of cDNA for the carcinoma–associated antigen GA733–2," *Proc. Natl. Acad. Sci. USA*, 87:3542–3546, 1990.

Tang et al., "Genetic immunization is a simple method for eliciting an immune response," *nature* 356:152–154, 1992.

Teitelbaumet et al., "In Vivo Effects of Antibodies Against a High Frequency Idiotype of Anti–DNA Antibodies in MRL Mice," 132:1282–1285, 1984.

Thomason et al., "Stable incorporation of a bacterial gene into adult rat skeletal muscle in vivo," *Cell Physiol.*, 27:C578–581, 1990.

Ulmer et al., "Heterologous Protection Against Influenza by Injection of DNA Encoding a Viral Protein," *Science*, 259:1745–1749, 1993.

Vanderbark et al., "Immunization with a synthetic T–cell receptor V–region peptide protects against experimental autoimmune encephalomyelitis," *Nature*, 341:541–544, 1989.

Vitadello et al., "Gene Transfer in Regenerating Muscle," *J. of Cellular Biochemistry*, Suppl. 17E:252, Mar. 29–Apr. 25, 1993.

Weiner et al., "Non–CD4 Molecules on Human Cells Important in HIV–1 Cell Entry," *Vaccines*, 115–120, 1989.

Will et al., "Cloned HBV DNA causes hepatitis in chimpanzees," *Nature*, 299:740–742, 1982.

Williams et al., Molecular Diagnosis of Borrelia burgdorferi Infection (Lyme Disease), *DNA and Cell Biology*, 11:207–213, 1992.

Williams et al., "Restricted heterogeneity of T Cell Receptor Transcripts in Rheumatoid Synovium," *J. Clin. Invest.*, 90:326–333, 1992.

Wolff et al., "Direct Gene Transfer into Mouse Muscle in Vivo," *Science*, 247:1465–1468, 1990.

Wolff et al., "Conditions Affecting Direct Gene Transfer into Rodent Muscle In Vivo," *BioTechniques*, 11:474–485, 1991.

Wucherpfennig te al., "Shared Human T Cell Receptor V Beta Usage to Immunodominant Regions of Myelin Basic Protein," *Science*, 248:1016–1019, 1990.

Fleckenstein et al., "Tumour induction with DNA of oncogenic primate herpesviruses," *Nature*, 274:57–59, 1978.

Boiron et al., "A Biological Property of Deoxyribonucleic Acid," *Discussion and Preliminary Reports*, 150–153, 1965.

McCoy et al., "Human Colon Carcinoma Ki–ras2 Oncogene and Its Correspondence Proto–Oncogene," *Mol. and Cellular Biology*, 4:1577–1582, 1984.

Rowe et al., "Studies of Mouse Polyoma Virus Infection," U.S. Department of Health, Education and Welfare, 379–391, 1958.

Orth et al., "Infectious and Oncogenic Effect of DNA Extracted from Cells Infected with Polyoma Virus," *P.S.E.B.M.,* 115:1090–1095, 1964.

McCutchan et al., "Enhancement of the Infectivity of Simian Virus 40 Deoxyribonucleic Acid with Diethylaminoethyl–Dextran," *J. of the Nat. Cancer Institute,* 41:351–356, 1968.

Mayne et al., "Tumour Induction by Simian Adenovirus SA7 DNA Fragments," *Nature New Biology,* 232:182–183, 1971.

Sol et al., "Oncogenicity of SV40 DNA in the Syrian Hamster," *J. gen. Vir.* 37:635–638, 1977.

Rowe et al., "B. Ecology of a Mouse Tumor Virus," *Perspectives in Virology,* 177–190.

Aldovini et al., "Mutations of RNA and Protein Sequences Involved in Human Immnodeficiency Virus Type 1 Packaging Result in Production of Noninfectious Virus," *J. Of Virology,* 64:1920–1926, 1990.

Benvenisty et al., "Direct introduction of genes into rats and expression of the genes," *Proc. Natl. Acad. Sci. USA,* 83:9551–9555, 1986.

Brandsma et al., "Use of a rapid, efficient inoculation method to induce papillomas by cottontail rabbit papillomavirus DNA shows that the E7 gene is required," *Proc. Natl. Acad. Sic. USA,* 88:4816–4820, 1991.

Desrosiers, "HIV with Multiple Gene Deletions as a Live Attenuated Vaccine for AIDS," *AIDS Res. And Human Retrovirues,* 8:411–421, 1992.

Friedmann et al., "Progress Toward Human Gene Therapy," *Science,* 244:1275–1281, 1989.

Kaneda et al., "Increased Expression of DNA Cointroduced with Nuclear Protein in Adult Rat Liver," *Science,* 243:375–378, 1989.

Nicolau et al., "In vivo expression of rat insulin after intravenous administration of the liposome–entrapped gene for rat insulin I," *Proc. Natl. Acad. Sci. USA,* 80:1068–1072, 1983.

Ronen et al., "Expression of wild–type and mutant p53 proteins by recombinant vaccinia viruses," *Nucl. Acids Res.,* 20:3435–3441, 1992.

Schauer et al., "The N–Terminal Region of HIV–1 Integrase is Required for Integration Activity, but not for DNA–Binding," *Biochem. Biophys. Res. Commun.,* 185:874–880, 1992.

Seeger et al., "The cloned genome of ground squirrel hepatitis virus is infectious in the animal," *Proc. Natl. Acad. Sci. USA,* 81:5849–5852, 1994.

Wu et al., "Receptor–mediated Gene Delivery and Expression in Vivo," *J. Biol. Chem.,* 263:14621–14624, 1988.

Yang et al., "In vivo and in vitro gene transfer to mammalian somatic cells by particle bombardment," *Proc. Natl. Acad. Sci. USA,* 87:9568–9572, 1990.

Zelenin et al., "High–velocity mechanical DNA transfer of the chloramphenicolacetyl transferase gene into rodent liver, kidney and mammary gland cells in organ explants and in vivo," *FEBS Letts,* 280:94–96, 1991.

Butini et al., *J. Cell. Biochem.,* Suppl. 18B:147, Abstract J306, 1994.

Eisen, *Microbiology,* "Introduction to Immune Responses," Bernard D. Davis et al. (eds.), Hagerstown: Harper & Row Publishers, p. 294, 1980.

Garry et al., *Science,* 250:1127–1129, 1990.

Glaser, *Genetic Engineering News,* 16(1) :6, 1996.

Haynes *Science,* 260:1279–1286, 1993.

Hoffenbach et al., *J. Immunol.,* 142:452–462, 1989.

Knuth et al., *Curr. Opin. Immunol.,* 3:659–664, 1991.

Ledley, *Human Gene Therapy,* 2:77–83, 1991.

Schultz et al. *AIDS,* 7(suppl. 1) :S161–170, 1993.

Torpey et al., *Clinical Immunol. Immunopathol.,* 68 (3): 263–272, 1993.

Wang et al., *Proc. Natl. Acad. Sci. USA,* 90:4356–4160, 1993.

Wells, *FEBS Lett.,* 332(1,2) :179–182, 1993.

 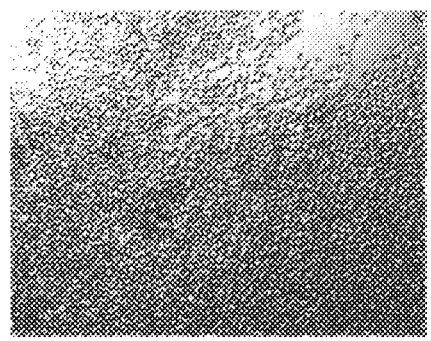
FIG.4A  FIG.4B
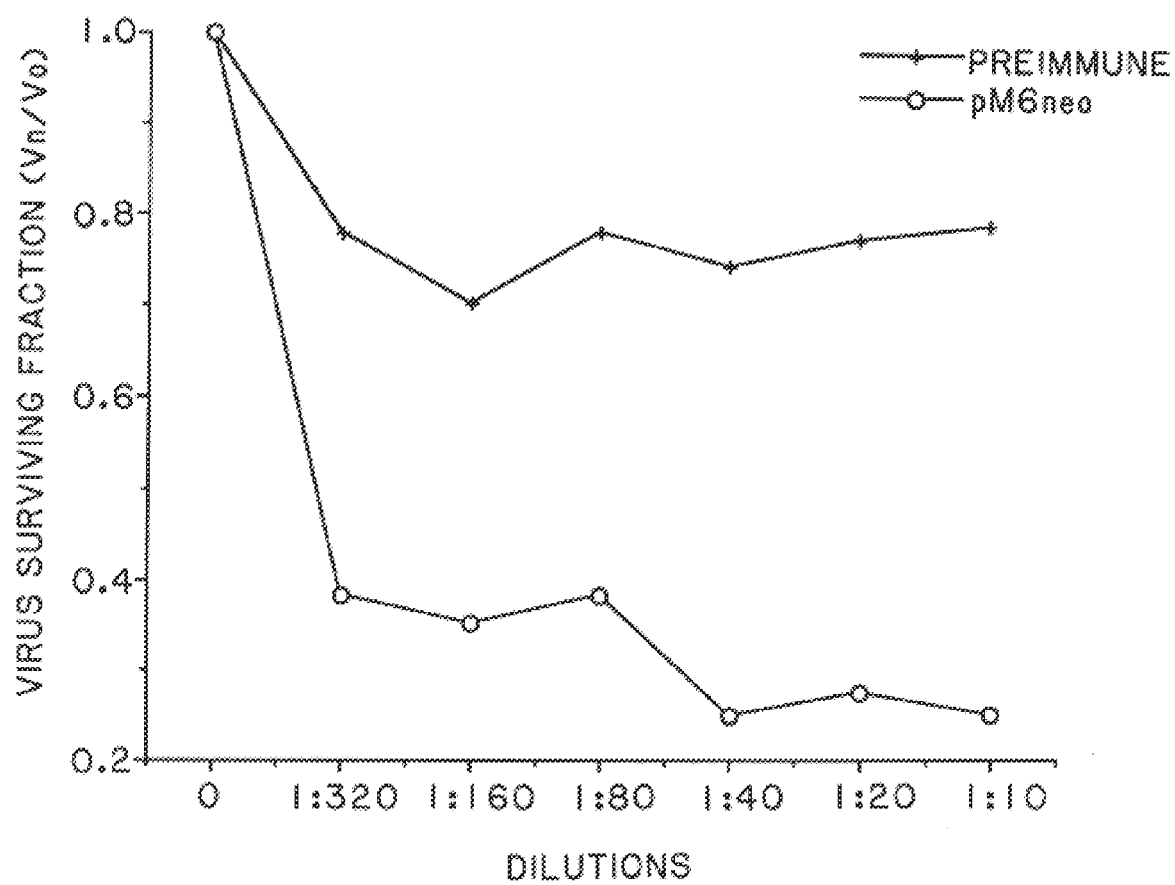
FIG.4C

GENETIC IMMUNIZATION

CROSS REFERENCE TO RELATED APPLICATIONS

This application is a Continuation application of U.S. patent application Ser. No. 08/125,012 filed Sep. 21, 1993, which issued as U.S. Pat. No. 5,593,972 on Jan. 14, 1997, which is a Continuation-In-Part application of U.S. patent application Ser. No. 08/029,336 filed Mar. 11, 1993, abandoned; which is a Continuation-In-Part application of U.S. patent application Ser. No. 08/008,342 filed Jan. 26, 1993, abandoned; all of which are incorporated herein by reference.

FIELD OF THE INVENTION

The present invention relates to use of genetic material as immunizing agents. In particular, the present invention relates to the introduction of DNA molecules into an individual's tissues or cells that then can produce proteins capable of eliciting an immune response.

BACKGROUND OF THE INVENTION

Vaccination and immunization generally refer to the introduction of a non-virulent agent against which an individual's immune system can initiate an immune response which will then be available to defend against challenge by a pathogen. The immune system identifies invading "foreign" compositions and agents primarily by identifying proteins and other large molecules which are not normally present in the individual. The foreign protein represents a target against which the immune response is made.

The immune system can provide multiple means for eliminating targets that are identified as foreign. These means include humoral and cellular responses which participate in antigen recognition and elimination. Briefly, the humoral response involves B cells which produce antibodies that specifically bind to antigens. There are two arms of the cellular immune response. The first involves helper T cells which produce cytokines and elicit participation of additional immune cells in the immune response. The second involves killer T cells, also known as cytotoxic T lymphocytes (CTLs), which are cells capable of recognizing antigens and attacking the antigen including the cell or particle it is attached to.

Vaccination has been singularly responsible for conferring immune protection against several human pathogens. In the search for safe and effective vaccines for immunizing individuals against infective pathogenic agents such as viruses, bacteria, and infective eukaryotic organisms, several strategies have been employed thus far. Each strategy aims to achieve the goal of protecting the individual against pathogen infection by administering to the individual, a target protein associated with the pathogen which can elicit an immune response. Thus, when the individual is challenged by an infective pathogen, the individual's immune system can recognize the protein and mount an effective defense against infection. There are several vaccine strategies for presenting pathogen proteins which include presenting the protein as part of a non-infective or less infective agent or as a discreet protein composition.

One strategy for immunizing against infection uses killed or inactivated vaccines to present pathogen proteins to an individual's immune system. In such vaccines, the pathogen is either killed or otherwise inactivated using means such as, for example, heat or chemicals. The administration of killed or inactivated pathogen into an individual presents the pathogen to the individual's immune system in a noninfective form and the individual can thereby mount an immune response against it. Killed or inactivated pathogen vaccines provide protection by directly generating T-helper and humoral immune responses against the pathogenic immunogens. Because the pathogen is killed or otherwise inactivated, there is little threat of infection.

Another method of vaccinating against pathogens is to provide an attenuated vaccine. Attenuated vaccines are essentially live vaccines which exhibit a reduced infectivity. Attenuated vaccines are often produced by passaging several generations of the pathogen through a permissive host until the progeny agents are no longer virulent. By using an attenuated vaccine, an agent that displays limited infectivity may be employed to elicit an immune response against the pathogen. By maintaining a certain level of infectivity, the attenuated vaccine produces a low level infection and elicits a stronger immune response than killed or inactivated vaccines. For example, live attenuated vaccines, such as the poliovirus and smallpox vaccines, stimulate protective T-helper, T-cytotoxic, and humoral immunities during their nonpathogenic infection of the host.

Another means of immunizing against pathogens is provided by recombinant vaccines. There are two types of recombinant vaccines: one is a pathogen in which specific genes are deleted in order to render the resulting agent non-virulent. Essentially, this type of recombinant vaccine is attenuated by design and requires the administration of an active, non-virulent infective agent which, upon establishing itself in a host, produces or causes to be produced antigens used to elicit the immune response. The second type of recombinant vaccine employs infective non-virulent vectors into which genetic material that encode target antigens is inserted. This type of recombinant vaccine similarly requires the administration of an active infective non-virulent agent which, upon establishing itself in a host, produces or causes to be produced, the antigen used to elicit the immune response. Such vaccines essentially employ infective non-virulent agents to present pathogen antigens that can then serve as targets for an anti-pathogen immune response. For example, the development of vaccinia as an expression system for vaccination has theoretically simplified the safety and development of infectious vaccination strategies with broader T-cell immune responses.

Another method of immunizing against infection uses subunit vaccines. Subunit vaccines generally consist of one or more isolated proteins derived from the pathogen. These proteins act as target antigens against which an immune response may be mounted by an individual. The proteins selected for subunit vaccine are displayed by the pathogen so that upon infection of an individual by the pathogen, the individuals immune system recognizes the pathogen and mounts a defense against it. Because subunit vaccines are not whole infective agents, they are incapable of becoming infective. Thus, they present no risk of undesirable virulent infectivity that is associated with other types of vaccines. It has been reported that recombinant subunit vaccines such as the hepatitis B surface antigen vaccine (HBsAg) stimulate a more specific protective T-helper and humoral immune response against a single antigen. However, the use of this technology to stimulate board protection against diverse pathogens remains to be confirmed.

Each of these types of vaccines carry severe drawbacks which render them less than optimally desirable for immunizing individuals against a particular pathogen.

It has been observed that absent an active infection, a complete immune response is not elicited. Killed and inactivated vaccines, because they do not reproduce or otherwise undergo an infective cycle, do not elicit the CTL arm of the cellular immune response in most cases. Additionally, killed and inactivated vaccines are sometimes altered by the means used to render them inactivated. These changes can affect the immunogenicity of the antigens. Subunit vaccines, which are merely discreet components of a pathogen, do not undergo any sort of infective cycle and often do not elicit the CTL arm of the cellular immune response. Absent the CTL arm, the immune response elicited by either vaccine is often insufficient to adequately protect an individual. In addition, subunit vaccines have the additional drawback of being both expensive to produce and purify.

Attenuated vaccines, on the other hand, often make very effective vaccines because they are capable of a limited, non-virulent infection and result in immune responses involving a humoral response and both arms of the cellular immune response. However, there are several problems associated with attenuated vaccines. First, it is difficult to test attenuated vaccines to determine when they are no longer pathogenic. The risk of the vaccine being virulent is often too great to properly test for effective attenuation. For example, it is not practically possible to test an attenuated form of Human Immunodeficiency virus (HIV) to determine if it is sufficiently attenuated to be a safe vaccine. Secondly, attenuated vaccines carry the risk of reverting into a virulent form of the pathogen. There is a risk of infecting individuals with a virulent form of the pathogen when using an attenuated vaccine.

Recombinant vaccines require the introduction of an active infective agent which, in many cases, is undesirable. Furthermore, in cases where the recombinant vaccine is the result of deletion of genes essential for virulence, such genes must exist and be identified. In vaccines in which pathogen genes are inserted into infective non-virulent vectors, many problems exist related to the immune response elicited against the vector antigens. These problems negatively impact the immune response elicited against the target antigen. First, the recombinant vaccine introduces a great number of vector antigens against which the immune system also responds. Secondly, the vector can be used only once per individual since, after the first exposure, the individual will develop immunity to the vector. These problems are both present, for example, in recombinant vaccines that employ vaccinia vectors such as those disclosed in U.S. Pat. No. 5,017,487 issued May 21, 1991 to Stunnenberg et al. This technology has not been universally successful against diverse pathogenic organisms. It is also complicated by the large amount of excess vaccinia antigens presented in the vaccinee. Once vaccinated with the vaccinia vector, the vaccinee cannot be effectively vaccinated again using the vaccinia vector.

Accordingly, the most effective vaccines for invoking a strong and complete immune response carry the most risk of harming the individual while the safer alternatives induce an incomplete, and therefore, less effective immune response. Furthermore, many subunit vaccines and recombinant vaccines using non-virulent vectors to produce target proteins are most useful if a single antigenic component can be identified which is singularly protective against live challenge by a pathogen. However, both technologies require that the protective component be identified. Such identification is often both laborious and time-consuming.

A distinct advantage would exist if there were a rapid system for directly testing subunit vaccination strategies without tissue culture and in the absence of excess vector antigens. Furthermore, it would be particularly advantageous if such a system could deliver an antigen that could be presented for development of both T cell immune arms.

There is a need for a means to immunize individuals against pathogen infection which can elicit a broad, biologically active protective immune response without risk of infecting the individual.

HIV infection represents a great threat to the human population today. Despite the intense resources expended and efforts made to develop an effective vaccine, the problem remains intractable. No vaccine is currently available that protects an individual against HIV infection. There is a great need for a method of immunizing an individual against HIV infection. There is a great need for an effective immunotherapy method to combat the development of AIDS in HIV infected individuals.

In addition to immunizing against pathogens, work has recently been undertaken to develop vaccines against cancer. Cancer vaccines currently being studied are essentially analogous to anti-pathogen subunit vaccines. Anti-cancer subunit vaccines essentially introduces a cancer-associated target protein into an individual. An immune response is elicited against the target protein in the same manner an immune response is elicited against a pathogen protein in the individual. The target protein is a protein that is specific to cancer cells. Subsequent appearance of the target protein when cancer occurs provides an immunogenic target for an immune response. Thus, the cancer vaccine immunizes an individual against cancer cells, an "endogenous pathogen", by immunizing against a target antigen specifically associated with the cancer. Specific proteins are administered which represent targets for an immunological response. As in the case of anti-pathogen subunit vaccines, the immune response elicited is often incomplete and insufficient to protect the individual. In particular, administration of a protein or peptide does not elicit a CTL response.

There is a need for an effective means to immunize individuals against hyperproliferative disease such as cancer in order to provide individuals with broad, biologically active protective immunity against specifically targeted hyperproliferating cells.

Many autoimmune diseases are mediated by specific antigen receptors. Autoimmune diseases generally refer to those diseases involving a self-directed immune response. Autoimmune diseases are referred to as being B cell mediated or T cell mediated. For example, Systemic Lupus Erythematosus (SLE) is considered a B cell mediated autoimmune disease. Many of the clinical manifestations of SLE are believed to be due to the presence of anti-DNA antibodies in the patients' serum, which combine with the antigen to form immune complexes. These immune complexes are deposited in tissues, setting off the inflammatory cascade. Rheumatoid Arthritis (RA) is an example of T cell mediated autoimmune disease. RA is believed to be mediated by autoreactive T cells present in the synovium (joint tissue), where they respond to an unknown antigen in the context of class II major histocompatibility complex (MHC II) molecules, such as HLA-DR4 which is genetically linked to RA. These T cells recognize a specific antigen associated with MHC II via their T cell antigen receptors (TCRs). Thus, autoreactive antigen receptors, such as antibodies or T cell antigen receptors are responsible for the initial recognition event in a series of pathogenic, inflammatory events which culminates in the clinical manifestations of autoimmune diseases such as SLE and RA.

Several studies have been performed in experimental systems where such autoreactive antigen receptors have been targeted or deleted. Animal model systems for autoimmune disease include a murine lupus model which occurs in a strain of NZB/NZW mice, and an experimental allergic encephalomyelitis (EAE) model which can be produced in susceptible mouse and rat strains following inoculation with myelin basic protein (MBP). In murine SLE, anti-idiotypic antibodies have been used therapeutically in an attempt to delete the autoreactive B cells which produce the autoreactive antibodies. In some cases, these anti-idiotypic antibodies have improved clinical manifestations of the disease (Hahn, B. H. and F. M. Ebling, 1984 *J. Immunol.* 132(1) :187–190), while in others they have worsened disease (Teitelbaum, D. et al., 1984 *J. Immunol.* 132(3):1282–1285). Similarly, in EAE, antibodies to autoreactive T cell antigen receptors have been utilized, as has been immunization with T cell antigen receptor-derived peptides. Again, in some instances this improves the disease Vandenbark, A., et al., 1989 *Nature* 341:541–544, while in other worsening of the disease occurs (Desquenne-Clark, L., et al., 1990 *Proc. Natl. Acad. Sci. USA* 88:7219–7223).

Thus, while it is possible to vaccinate against autoimmune disease in some cases, the nature of the immune response elicited affects the clinical outcome of such therapies. For example, if the vaccination results in development of an antibody response, with subsequent anti-idiotype development, these anti-idiotypic antibodies could target the autoreactive B cells or T cells for complement-mediated mediated lysis, with resulting clinical improvement. Alternatively, if the immunization results in production of non-complement fixing anti-idiotypic antibodies, these would bind to the autoreactive B cells or T cells and cross-link their antigen receptors. Typically, this leads to activation of the cells and subsequent increased production of the autoreactive antibodies or T cells, with worsening of the clinical condition. Alternatively, if a predominant T cell response is elicited by vaccination, this could result in either a helper T cell response which would be expected to worsen disease or a killer/suppressor cell response which should improve the disease.

There is a need for an effective means to immunize individuals against and treat individuals suffering from autoimmune diseases which would elicit a CTL response capable of targeting either B cells that produce the antibodies involved in the disease (in the case of B cell mediated autoimmune disease) or the T cells that produce the specific T cell antigen receptor which are involved in the disease (in the case of T cell mediated autoimmune disease).

The direct introduction of a normal, functional gene into a living animal has been studied as a means for replacing defective genetic information. In such studies, DNA is introduced directly into cells of a living animal. Nabel, E. G., et al., (1990) *Science* 249:1285–1288, disclose site-specific gene expression in vivo of a beta-galactosidase gene that was transferred directly into the arterial wall in mice. Wolfe, J. A. et al., (1990) *Science* 247:1465–1468, disclose expression of various reporter genes that were directly transferred into mouse muscle in vivo. The use of direct gene transfer as an alternative anti-pathogen vaccination method is suggested. Acsadi G., et al., (1991) *Nature* 352:815–818, disclose expression of human dystrophin gene in mice after intramuscular injection of DNA constructs. Wolfe, J. A., et al., 1991 *BioTechniques* 11(4):474–485, which is incorporated herein by reference, refers to conditions affecting direct gene transfer into rodent muscle in vivo. Multiple injections of plasmid DNA are reported to result in higher levels of protein production but not to the extent that the levels of protein production are proportional to additional plasmid DNA added. Feigner, P. L. and G. Rhodes, (1991) *Nature* 349:351–352, disclose direct delivery of purified genes in vivo as drugs without the use of retroviruses. Use of direct gene transfer by single injection are suggested as a possible vaccination strategy and a cellular immune response to HIV gp120 resulting from introduction of plasmid DNA encoding the same into cells is reported to have been observed. PCT International Application Number PCT/US90/01515 published Oct. 4, 1990 discloses methods of immunizing an individual against pathogen infection by directly injecting naked polynucleotides into the individual's cells in a single step procedure. The use of transfecting agents other than lipofectins is specifically excluded from the disclosed methods. The stimulation of inoculated cells is neither disclosed nor suggested. An HIV vaccine is disclosed which consists of the introduction of polynucleotides that encode the viral protein gp120. The operability of this vaccine is not evidenced. Thomason, D. B. et al., (1990) *Cell Physiol.* 27:C578–581 and PCT Patent Application Serial No. WO 91/12329 disclose administering bupivacaine to muscle cells in order to induce satellite cell proliferation. In particular, Thomason, D. B. et al., (1990) *Cell Physiol.* 27:C578–581 and PCT Patent Application Serial No. WO 91/12329 disclose retroviral-mediated transfer of genes into adult tissue in which a mitotically-active state of satellite cells is induced. The retroviruses contain recombinant retroviral RNA that includes a foreign reporter gene incorporated within the viral particle.

SUMMARY OF THE INVENTION

The present invention relates to a method of immunizing an individual against a pathogen. The method comprises the steps of contacting cells of said individual with an agent that facilitates the uptake of DNA by the cells, the agent preferably being a cell stimulating agent, and administering to the cells, a DNA molecule that comprises a DNA sequence that encodes a peptide which comprises at least an epitope identical or substantially similar to an epitope displayed on a pathogen antigen operatively linked to regulatory sequences. The DNA molecule is capable of being expressed in the cells of the individual.

The present invention relates to a method of immunizing a human against HIV. The method comprises the steps of administering to a human a DNA molecule that comprises a DNA sequence that encodes at least one peptide that comprises at least one epitope identical or substantially similar to an epitope displayed on an HIV protein operatively linked to regulatory sequences.

The present invention relates to a method of immunizing a human against HIV. The method comprises the steps of administering two different DNA molecules to different cells of the human. Each DNA molecule comprises a DNA sequence that encodes at least one peptide which comprises at least one epitope identical or substantially similar to an epitope displayed on an HIV protein operatively linked to regulatory sequences. The different DNA molecules are each capable of being expressed in human cells. The different DNA molecules comprise different DNA sequences that encode at least one different peptide from the other.

The present invention related to a method of immunizing an individual against a hyperproliferative disease. The method comprises the steps of administering to cells of an individual, a DNA molecule that comprises a DNA sequence that encodes a peptide that comprises at least an epitope identical or substantially similar to an epitope displayed on a hyperproliferative disease-associated protein operatively linked to regulatory sequences; the DNA molecule being capable of being expressed in the cells.

The present invention relates to a method of immunizing an individual against an autoimmune disease. The method comprises the steps of administering to cells of an individual, a DNA molecule that comprises a DNA sequence that encodes a peptide that comprises at least an epitope identical or substantially similar to an epitope displayed on an autoimmune disease-associated protein operatively linked to regulatory sequences; the DNA molecule being capable of being expressed in the cells.

The present invention relates to an HIV vaccine comprising a pharmaceutically acceptable carrier or diluent and a DNA molecule that encodes one or more peptides that each comprises at least an epitope identical or substantially similar to an epitope displayed on at least one HIV protein operatively linked to regulatory sequences; the DNA molecule being capable of being expressed in human cells.

The present invention relates to an HIV vaccine comprising two inoculants. The first inoculant comprises a pharmaceutically acceptable carrier or diluent and a first DNA molecule. The first DNA molecule comprises a DNA sequence that encodes one or more peptides that each comprises at least an epitope identical or substantially similar to an epitope displayed on at least one HIV protein operatively linked to regulatory sequences; the DNA molecule being capable of being expressed in human cells. The second inoculant comprises a pharmaceutically acceptable carrier or diluent and a second DNA molecule. The second DNA molecule comprises a DNA sequence that encodes one or more peptides that each comprises at least an epitope identical or substantially similar to an epitope displayed on at least one HIV protein operatively linked to regulatory sequences; the DNA molecule being capable of being expressed in human cells. The first and second DNA molecules are different and encode different peptides.

BRIEF DESCRIPTION OF THE DRAWINGS

FIGS. 4A and 4B are photographs of MT-2 cells infected with $TCID_{50}$HIV-1/III$_B$ cell-free virus that was preincubated with serial dilutions of antisera.

FIG. 4C is a graph illustrating the neutralization values $(V_n/V_o)$ versus the dilution factors from results using control serum (x=pMAMneoBlue vector-immunized mice) and test sera (O=pM160-immunized mice).

DETAILED DESCRIPTION OF THE INVENTION

Figure 1A:
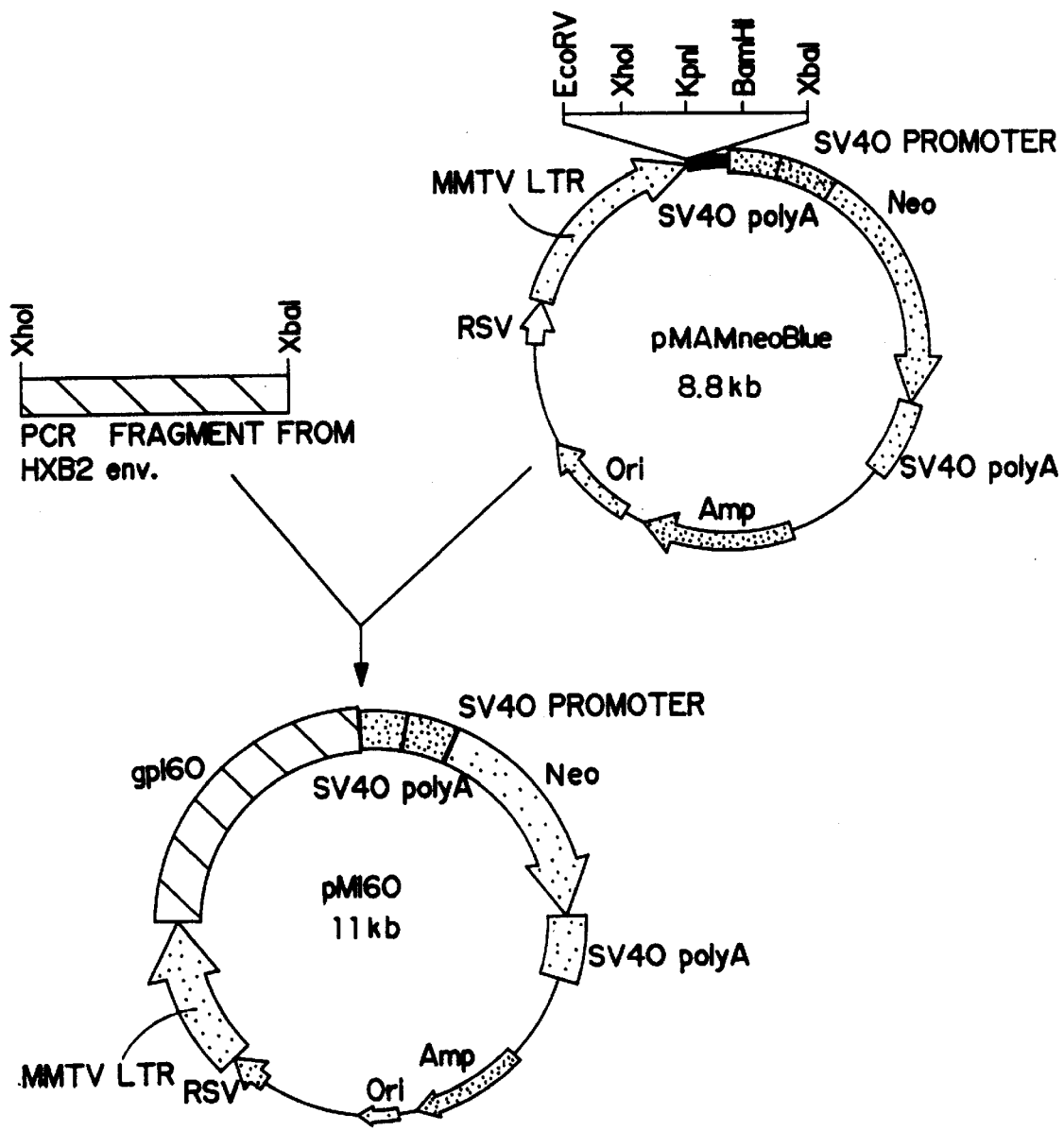
FIG. 1A is a diagram depicting the construction of plasmid pM160 which was produced by inserting a PCR-generated fragment that encodes the HIV-HXB2 glycoprotein gp160 into plasmid pMAMneoBlue (Clonetech).

The present invention relates to methods of eliciting immune responses in an individual which can protect an individual from pathogen infection or combat diseases and disorders involving cells that produce specific proteins. According to the present invention, genetic material that encodes an immunogenic peptide or protein is directly administered to an individual either in vivo or to the cells of an individual ex vivo. The genetic material encodes a peptide or protein that shares at least an epitope with an immunogenic protein to be targeted. The genetic material is expressed by the individual's cells to form immunogenic target proteins that elicit an immune response. The resulting immune response is broad based: in addition to a humoral immune response, both arms of the cellular immune response are elicited. Thus, the immune responses elicited by vaccination methods of the present invention are particularly effective to protect against pathogen infection or combat cells associated with hyperproliferative diseases or autoimmune diseases.

The immune response elicited by the target protein that is produced by vaccinated cells in an individual is a broad-based immune response which involves B cell and T cell responses including cytotoxic T cell (CTL) responses. The target antigens produced within the cells of the host are processed intracellularly: broken down into small peptides, bound by Class I MHC molecules, and expressed on the cell surface. The Class I MHC-target antigen complexes are capable of stimulating $CD8^+$ T-cells, which are phenotypically the killer/suppressor cells. Genetic immunization according to the present invention is thus capable of eliciting cytotoxic T-cell (CTL) responses (killer cell responses). It has been observed that genetic immunization according to the present invention is more likely to elicit CTL responses than other methods of immunization.

The present invention is useful to elicit broad immune responses against a target protein. Target proteins may be proteins specifically associated with pathogens or the individual's own "abnormal" cells. The present invention is useful to immunize individuals against pathogenic agents and organisms such that an immune response against a pathogen protein provides protective immunity against the pathogen. The present invention is particularly useful to protect an individual against infection by non-encapsulated intracellular pathogens which produce proteins within the host cells. The immune response generated against such proteins is capable of eliminating infected cells using CTLs which specifically recognize and eliminate such infected cells. The CTL response is crucial in protection against pathogens such as viruses and other intracellular pathogens which produce proteins within infected cells. The present invention is useful to combat hyperproliferative diseases and disorders such as cancer by eliciting an immune response against a target protein that is specifically associated with the hyperproliferative cells. In such cases, a cytotoxic immune response against the hyperproliferating cells which produce the target protein is elicited. The present invention is useful to combat autoimmune diseases and disorders by eliciting an immune response against a target protein that is specifically associated with cells involved in the autoimmune condition. In such cases, the cytotoxic immune response against cells that produce the target protein is provided. The CTL response can be utilized for the specific elimination of deleterious cell types which, during their production of proteins, display antigens bound by Class I MHC molecules. Therefore, genetic immunization according to the present invention is more likely to result in anti-pathogen protection and therapy than standard immunization using killed, inactivated or protein- or peptide-based subunit vaccines and furthermore, may be used in immunization procedures to protect against and treat individuals suffering from cancer and autoimmune diseases.

Genetic immunization according to the present invention elicits an effective immune response without the use of infective agents or infective vectors. Vaccination techniques which usually do produce a CTL response do so through the use of an infective agent. A complete, broad based immune response is not generally exhibited in individuals immunized with killed, inactivated or subunit vaccines. The present invention achieves the full complement of immune responses in a safe manner without the risks and problems associated with vaccinations that use infectious agents.

According to some embodiments of the present invention, cells are treated with compounds that facilitate uptake of genetic constructs by the cells. According to some embodiments of the present invention, cells are treated with compounds that stimulate cell division and facilitate uptake of genetic constructs. Administration of compounds that facilitate uptake of genetic constructs by the cells including cell stimulating compounds results in a more effective immune response against the target protein encoded by the genetic construct.

According to some embodiments of the present invention, the genetic construct is administered to an individual using a needleless injection device. According to some embodiments of the present invention, the genetic construct is simultaneously administered to an individual intradermally, subcutaneously and intramuscularly using a needleless injection device. Administration of genetic constructs using needleless injection devices is disclosed in U.S. application Ser. No. 08/093,235 filed Jul. 15, 1993, which is incorporated herein by reference.

According to the present invention, DNA or RNA that encodes a target protein is introduced into the cells of an individual where it is expressed, thus producing the target protein. The DNA or RNA is linked to regulatory elements necessary for expression in the cells of the individual. Regulatory elements for DNA include a promoter and a polyadenylation signal. In addition, other elements, such as a Kozak region, may also be included in the genetic construct.

As used herein, the term "genetic construct" refers to the DNA or RNA molecule that comprises a nucleotide sequence which encodes the target protein and which includes. initiation and termination signals operably linked to regulatory elements including a promoter and polyadenylation signal capable of directing expression in the cells of the vaccinated individual. As used herein, the term "express-ible form" refers to gene constructs which contain the necessary regulatory elements operable linked to a coding sequence that encodes a target protein, such that when present in the cell of the individual, the coding sequence will be expressed. As used herein, the term "genetic vaccine" refers to a pharmaceutical preparation that comprises a genetic construct.

As used herein, the term "target protein" refers to a protein against which an immune response can be elicited. The target protein is an immunogenic protein which shares at least an epitope with a protein from the pathogen or undesirable cell-type such as a cancer cell or a cell involved in autoimmune disease against which immunization is required. The target protein is an immunogenic protein derived from the pathogen or undesirable cell-type such as a cancer cell or a cell involved in autoimmune disease. Target proteins share epitopes with either pathogen-associated proteins, proteins associated with hyperproliferating cells, or proteins associated with autoimmune disorders, depending upon the type of genetic vaccine. The immune response directed against the target protein will protect the individual against the specific infection or disease with which the target protein is associated. For example, a genetic vaccine with a DNA or RNA molecule that encodes a pathogen-associated target protein is used to elicit an immune response that will protect the individual from infection by the pathogen. Likewise, a genetic vaccine with a DNA or RNA molecule that encodes a target protein associated with a hyperproliferative disease such as, for example, a tumor-associated protein, is used to elicit an immune response directed at hyperproliferating cells. A genetic vaccine with a DNA or RNA molecule that encodes a target protein that is associated with T cell receptors or antibodies involved in autoimmune diseases is used to elicit an immune response that will combat the autoimmune disease by eliminating cells in which the natural form of target protein is being produced. Target proteins may be either pathogen-associated proteins, proteins associated with hyperproliferating cells, or proteins associated with autoimmune disorders, depending upon the type of genetic vaccine.

As used herein, the term "sharing an epitope" refers to proteins which comprise at least one epitope that is identical to or substantially similar to an epitope of another protein.

As used herein, the term "substantially similar epitope" is meant to refer to an epitope that has a structure which is not identical to an epitope of a protein but nonetheless invokes an cellular or humoral immune response which cross reacts to that protein.

The genetic construct of genetic vaccines comprise a nucleotide sequence that encodes a target protein operably linked to regulatory elements needed for gene expression. Accordingly, incorporation of the DNA or RNA molecule into a living cell results in the expression of the DNA or RNA encoding the target protein and thus, production of the target protein.

When taken up by a cell, the genetic construct which includes the nucleotide sequence encoding the target protein operably linked to the regulatory elements may remain present in the cell as a functioning extrachromosomal molecule or it may integrate into the cell's chromosomal DNA. DNA may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Since integration into the chromosomal DNA necessarily requires manipulation of the chromosome, it is preferred to maintain the DNA construct as a replicating or non-replicating extrachromosomal molecule. This reduces the risk of damaging the cell by splicing into the chromosome without affecting the effectiveness of the vaccine. Alternatively, RNA may be administered to the cell. It is also contemplated to provide the genetic construct as a linear minichromosome including a centromere, telomeres and an origin of replication.

The necessary elements of a genetic construct of a genetic vaccine include a nucleotide sequence that encodes a target protein and the regulatory elements necessary for expression of that sequence in the cells of the vaccinated individual. The regulatory elements are operably linked to the DNA sequence that encodes the target protein to enable expression.

The molecule that encodes a target protein is a protein-encoding molecule which is translated into protein. Such molecules include DNA or RNA which comprise a nucleotide sequence that encodes the target protein. These molecules may be cDNA, genomic DNA, synthesized DNA or a hybrid thereof or an RNA molecule such as mRNA. Accordingly, as used herein, the terms "DNA construct", "genetic construct" and "nucleotide sequence" are meant to refer to both DNA and RNA molecules.

The regulatory elements necessary for gene expression of a DNA molecule include: a promoter, an initiation codon, a stop codon, and a polyadenylation signal. In addition, enhancers are often required for gene expression. It is necessary that these elements be operable in the vaccinated individual. Moreover, it is necessary that these elements be operably linked to the nucleotide sequence that encodes the target protein such that the nucleotide sequence can be expressed in the cells of a vaccinated individual and thus the target protein can be produced.

Initiation codons and stop codon are generally considered to be part of a nucleotide sequence that encodes the target protein. However, it is necessary that these elements are functional in the vaccinated individual.

Similarly, promoters and polyadenylation signals used must be functional within the cells of the vaccinated individual.

Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

Examples of polyadenylation signals useful to practice the present invention, especially in the production of a genetic vaccine for humans, include but are not limited to SV40 polyadenylation signals and LTR polyadenylation signals. In particular, the SV40 polyadenylation signal which is in pCEP4 plasmid (Invitrogen, San Diego, Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration.

An additional element may be added which serves as a target for cell destruction if it is desirable to eliminate cells receiving the genetic construct for any reason. A herpes thymidine kinase (tk) gene in an expressible form can be included in the genetic construct. When the construct is introduced into the cell, tk will be produced. The drug gangcyclovir can be administered to the individual and that drug will cause the selective killing of any cell producing tk. Thus, a system can be provided which allows for the selective destruction of vaccinated cells.

In order to be a functional genetic construct, the regulatory elements must be operably linked to the nucleotide sequence that encodes the target protein. Accordingly, it is necessary for the initiation and termination codons to be in frame with the coding sequence.

In order to maximize protein production, regulatory sequences may be selected which are well suited for gene expression in the vaccinated cells. Moreover, codons may be selected which are most efficiently transcribed in the vaccinated cell. One having ordinary skill in the art can produce DNA constructs which are functional in vaccinated cells.

In order to test expression, genetic constructs can be tested for expression levels in vitro using tissue culture of cells of the same type as those to be vaccinated. For example, if the genetic vaccine is to be administered into human muscle cells, muscle cells grown in culture such as solid muscle tumors cells of rhabdomyosarcoma may be used as an in vitro model to measure expression level.

The present invention provides methods of conferring a broad based protective immune response against pathogen infection, hperproliferative diseases and autoimmune diseases without the use of infectious agents. The genetic constructs used in the present invention are not incorporated with retroviral particles. The genetic constructs are taken up by the cell without viral particle-mediated insertion such as that which occurs when retorvirus particles with retroviral RNA that is incorporated in retroviral particles infects a cell. As used herein, the term "free from viral particles" is meant to refer to genetic constructs that are not incorporated within viral particles. In some embodiments, the genetic constructs constitute less than a complete, replicatable viral genome such that upon introduction into the cell, the genetic construct possesses insufficient genetic information to direct production of infectious viral particles. As used herein, the term "incomplete viral genome" is meant to refer to a genetic construct which contains less than a complete genome such that incorporation of such a genetic construct into a cell does not constitute introduction of sufficient genetic information for the production of infectious virus.

One aspect of the present invention provides a method of conferring a broad based protective immune response against pathogen infection, diseases associated with hyperproliferative cells or autoimmune diseases by administering genetic constructs to cells contacted with an agent that facilitates the uptake of genetic material, particularly cell stimulating agents. The genetic construct may be administered with or without the use microprojectiles.

The present invention may be used to immunize an individual against all pathogens such as viruses, prokaryote and pathogenic eukaryotic organisms such as unicellular pathogenic organisms and multicellular parasites. The present invention is particularly useful to immunize an individual against those pathogens which infect cells and which are not encapsulated such as viruses, and prokaryote such as gonorrhoea, listeria and shigella. In addition, the present invention is also useful to immunize an individual against protozoan pathogens which include a stage in the life cycle where they are intracellular pathogens. As used herein, the term "intracellular pathogen" is meant to refer to a virus or pathogenic organism that, at least part of its reproductive or life cycle, exists within a host cell and therein produces or causes to be produced, pathogen proteins.

Table 1 provides a listing of some of the viral families and genera for which vaccines according to the present invention can be made. DNA constructs that comprise DNA sequences which encode the peptides that comprise at least an epitope identical or substantially similar to an epitope displayed on a pathogen antigen such as those antigens listed on the tables are useful in vaccines.

In addition to being particularly effective against pathogens which infect the cells of an individual, the present invention is also useful to immunize an individual against other pathogens including prokaryotic and eukaryotic protozoan pathogens as well as multicellular parasites. Table 2 contains a list of bacterial and eukaryotic pathogens for which vaccines according to the present invention may be made.

In order to produce a genetic vaccine to pagainst against pathogen infection, genetic material which encodes immunogenic proteins against which a protective immune response can be mounted must be included in the genetic construct. Whether the pathogen infects intracellularly, for which the present invention is particularly useful, or extracellularly, it is unlikely that all pathogen antigens will elicit a protective response. Because DNA and RNA are both relatively small and can be produced relatively easily, the present invention provides the additional advantage of allowing for vaccination with multiple pathogen antigens. The genetic construct used in the genetic vaccine can include genetic material which encodes many pathogen antigens. For example, several viral genes may be included in a single construct thereby providing multiple targets. In addition, multiple inoculants which can be delivered to different cells in an individual can be prepared to collectively include, in some cases, a complete or, more preferably, an incomplete such as a near complete set of genes in the vaccine. For example, a complete set of viral genes may be administered using two constructs which each contain a different half of the genome which are administered at different sites. Thus, an immune response may be invoked against each antigen without the risk of an infectious virus being assembled. This allows for the introduction of more than a single antigen target and can eliminate the requirement that protective antigens be identified.

The ease of handling and inexpensive nature of DNA and RNA further allow for more efficient means of screening for protective antigens. Genes can be sorted and systematically tested much more easily than proteins. The pathogenic agents and organism for which the vaccine is being produced to protect against is selected and an immunogenic protein is identified. Tables 1 and 2 include lists of some of the pathogenic agents and organisms for which genetic vaccines can be prepared to protect an individual from infection by them.

Another aspect of the present invention provides a method of conferring a broad based protective immune response against hyperproliferating cells that are characteristic in hyperproliferative diseases and to a method of treating individuals suffering from hyperproliferative diseases. As used herein, the term "hyperproliferative diseases" is meant to refer to those diseases and disorders characterized by hyperproliferation of cells. Examples of hyperproliferative diseases include all forms of cancer and psoriasis.

It has been discovered that introduction of a genetic construct that includes a nucleotide sequence which encodes an immunogenic "hyperproliferating cell"-associated protein into the cells of an individual results in the production of those proteins in the vaccinated cells of an individual. As used herein, the term "hyperproliferative-associated protein" is meant to refer to proteins that are associated with a hyperproliferative disease. These proteins can elicit a broad biologically active immune response in the individual including CTLs that can effectively combat and eliminate hyperproliferating cells in the individual. Thus, to immunize against hyperproliferative diseases, a genetic construct that includes a nucleotide sequence which encodes a protein that is associated with a hyperproliferative disease is administered to an individual. When expressed, the protein produced elicits an immune response directed at cells that produce the protein.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides which comprise at least an epitope found on such proteins. In some cases, a hyperproliferative-associated protein is the product of a mutation of a gene that encodes a protein. The mutated gene encodes a protein which is nearly identical to the normal protein except it has a slightly different amino acid sequence which results in a different epitope not found on the normal protein.

Such target proteins include those which are proteins encoded by oncogenes. Generally, oncogenes can be divided into three groups depending upon the portion of the cell where their gene products are found. Oncogenes such as myb, myc, fyn, and the translocation gene bcr/ab1 encode products that remain in the nucleus and are involved in transcription and cell cycle events. Gene products of oncogenes such as ras, src and P53 are generally found in the cytoplasm. Membrane bound products of oncogenes include neu, trk and EGRF. While protein products of these genes are often found in normal cells, they exist at greater levels in cancer cells. Thus, cancer cells can be expected to be more likely to have these proteins bound to Class I MHC molecules at the cell surface. Accordingly, CTLs which specifically recognize the target protein/MHC I complex will be more effective against cancer cells.

In addition to oncogene products as target antigens, variable regions of antibodies made by B cell lymphomas and variable regions of T cell receptors of T cell lymphomas can also be used as target antigens. These antigens are discussed and described in greater detail below in the section referring to autoimmune disease. However, it is contemplated that similar vaccination strategies can be used for treating and preventing these types of cancer.

Additionally, other tumor-associated proteins can be used as target proteins. Such proteins are generally those which are found at higher levels in tumor cells. Examples include the protein recognized by monoclonal antibody 17-1A and folate binding proteins.

While the present invention may be used to immunize an individual against one or more of several forms of cancer, the present invention is particularly useful to immunize an individual who is predisposed to develop a particular cancer or who has had cancer and is therefore susceptible to a relapse.

Developments in genetics and technology as well as epidemiology allow for the determination of probability and risk assessment for the development of cancer in individual. Using genetic screening and/or family health histories, it is possible to predict the probability a particular individual has for developing any one of several types of cancer. Those individuals identified as being predisposed to developing a particular form of cancer can, by using the methods of the present invention, take prophylactic steps towards reducing the risk of cancer. According to the present invention, high-risk individuals can be immunized against the form of cancer that they have a predisposition to develop.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmunethyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) which are involved in the disease have been characterized. These TCRs include V$\beta$-3, V$\beta$-14, V$\beta$-17 and V$\alpha$-17. Thus, vaccination with a DNA construct that encodes at least one of these proteins will elicit an immune response that will target T cells involved in RA. See: Howell, M. D., et al., 1991 *Proc. Natl. Acad. Sci. USA* 88:10921–10925; Paliard, X., et al., 1991 *Science* 253:325–329; Williams, W. V., et al., 1992 *J. Clin. Invest.* 90:326–333; each of which is incorporated herein by reference.

In MS, several specific variable regions of TCRs which are involved in the disease have been characterized. These TCRs include V$\beta$-7 and V$\alpha$-10. Thus, vaccination with a DNA construct that encodes at least one of these proteins will elicit an immune response that will target T cells involved in MS. See: Wucherpfennig, K. W., et al., 1990 *Science* 248:1016–1019; Oksenberg, J. R., et al., 1990 *Nature* 345:344–346; each of which is incorporated herein by reference.

In scleroderma, several specific variable regions of TCRs which are involved in the disease have been characterized. These TCRs include V$\beta$-6, V$\beta$-8, V$\beta$-14 and V$\alpha$-16, V$\alpha$-3C, V$\alpha$-7, V$\alpha$-14, $\alpha$-15, V$\alpha$-16, V$\alpha$-28 and V$\alpha$-12. Thus, vaccination with a DNA construct that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies which bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al. 1987 *Sequence of Proteins of Immunological Interest* U.S. Department of Health and Human Services, Bethesda, Md., which is incorporated herein by reference. In addition, a general method for cloning functional variable regions from antibodies can be found in Chaudhary, V. K., et al., 1990 *Proc. Natl. Acad. Sci. USA* 87:1066, which is incorporated herein by reference.

According to the invention, the genetic vaccine may be administered directly into the individual to be immunized or ex vivo into removed cells of the individual which are reimplanted after administration. By either route, the genetic material is introduced into cells which are present in the body of the individual. Routes of administration include, but are not limited to, intramuscular, intraperitoneal, intradermal, subcutaneous, intravenous, intraarterially, intraoccularly and oral as well as transdermally or by inhalation or suppository. Preferred routes of administration include intramuscular, intraperitoneal, intradermal and subcutaneous injection. Genetic constructs may be administered by means including, but not limited to, traditional syringes, needleless injection devices, or "microprojectile bombardment gene guns". Alternatively, the genetic vaccine may be introduced by various means into cells that are removed from the individual. Such means include, for example, ex vivo transfection, electroporation, microinjection and microprojectile bombardment. After the genetic construct is taken up by the cells, they are reimplanted into the individual. It is contemplated that otherwise non-immunogenic cells that have genetic constructs incorporated therein can be implanted into the individual even if the vaccinated cells were originally taken from another individual.

The genetic vaccines according to the present invention comprise about 1 nanogram to about 1000 micrograms of DNA. In some preferred embodiments, the vaccines contain about 10 nanograms to about 800 micrograms of DNA. In some preferred embodiments, the vaccines contain about 0.1 to about 500 micrograms of DNA. In some preferred embodiments, the vaccines contain about 1 to about 350 micrograms of DNA. In some preferred embodiments, the vaccines contain about 25 to about 250 micrograms of DNA. In some preferred embodiments, the vaccines contain about 100 micrograms DNA.

The genetic vaccines according to the present invention are formulated according to the mode of administration to be used. One having ordinary skill in the art can readily formulate a genetic vaccine that comprises a genetic construct. In cases where intramuscular injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vaso-constriction agent is added to the formulation. The pharmaceutical preparations according to the present invention are provided sterile and pyrogen free.

Genetic constructs may optionally be formulated with one or more response enhancing agents such as: compounds which enhance transfection, i.e. transfecting agents; compounds which stimulate cell division, i.e. replication agents; compounds which stimulate immune cell migration to the site of administration, i.e. inflammatory agents; compounds which enhance an immune response, i.e. adjuvants or compounds having two or more of these activities.

As used herein, the term "transfection agent" is meant refer to an agent that promotes and facilitates the uptake of genetic material by the cells. According to the present invention, cells are contacted with one or more transfection agents prior to, simultaneously with or subsequent to administration of the genetic construct.

As used herein, the term "replicating agent" is meant to refer to an agent that stimulates cell division and replication. According to the present invention, cells are contacted with one or more replicating agents prior to simultaneously with, or subsequent to administration of the genetic construct.

As used herein, the term "inflammatory agent" is meant to refer to an agent that induces migration and chemotaxis of cells involved in an immune response to the site in an individual where it is administered. According to the present invention, cells are contacted with one or more inflammatory agents prior to, simultaneously with, or subsequent to administration of the genetic construct. An inflammatory agent can be an irritant which disrupts or damages tissue. Thus, in addition to the cells that are normally present at the site of administration, the migrating immune cells can come into contact with and take up the administered genetic construct.

As used herein, the term "cell stimulating agent" refers to a compound that is both a transfection agent in that it facilitates DNA and RNA uptake by cells and a replicating agent in that is stimulates cell division and replication. As used herein, the terms "cell stimulating agent" or "cell proliferative agent" are used interchangeably and refer to compounds which are transfecting agents and replicating agents. Cell stimulating agents facilitate DNA and RNA uptake, and stimulate cell division.

In some embodiments, the transfecting agent used is preferably a cell stimulating agent. In some embodiments, a transfecting agent is used which is also an inflammatory agent. In some embodiments, a transfecting agent is used which is also an adjuvant. In some embodiments, a transfecting agent is used which is also an inflammatory agent and an adjuvant. In some embodiments, a cell stimulating agent is used which is also an inflammatory agent. In some embodiments, a cell stimulating agent is used which is also an adjuvant. In some embodiments, a cell stimulating agent is used which is also an inflammatory agent and an adjuvant. In some embodiments, a replicating agent is used which is also an inflammatory agent. In some embodiments, a replicating agent is used which is also an adjuvant. In some embodiments, a replicating agent is used which is also an inflammatory agent and an adjuvant. In some embodiments, an inflammatory agent is used which is also an adjuvant.

In a preferred embodiment, bupivacaine, a well known and commercially available pharmaceutical compound, is administered prior to, simultaneously with or subsequent to the genetic construct. Bupivacaine and the genetic construct may be formulated in the same composition. Bupivacaine is particularly useful as a cell stimulating agent in view of its many properties and activities when administered to tissue. Bupivacaine promotes and facilitates the uptake of genetic material by the cell. As such, it is a transfecting agent. Administration of genetic constructs in conjunction with bupivacaine facilitates entry of the genetic constructs into cells. Bupivacaine is believed to disrupt or otherwise render the cell membrane more permeable. Cell division and replication is stimulated by bupivacaine. Accordingly, bupivacaine acts as a replicating agent. Administration of bupivacaine also irritates and damages the tissue. As such, it acts as an inflammatory agent which elicits migration and chemotaxis of immune cells to the site of administration. In addition to the cells normally present at the site of administration, the cells of the immune system which migrate to the site in response to the inflammatory agent can come into contact with the administered genetic material and the bupivacaine. Bupivacaine, acting as a transfection agent, is available to promote uptake of genetic material by such cells of the immune system as well.

Bupivacaine is related chemically and pharmacologically to the aminoacyl local anesthetics. It is a homologue of mepivacaine and related to lidocaine. Bupivacaine renders muscle tissue voltage sensitive to sodium challenge and effects ion concentration within the cells. A complete description of bupivacaine's pharmacological activities can be found in Ritchie, J. M. and N. M. Greene, *The Pharmacological Basis of Therapeutics*, Eds.: Gilman, A. G. et al, 8th Edition, Chapter 15:3111, which is incorporated herein by reference. Bupivacaine and compounds that display a functional similarity to bupivacaine are preferred in the method of the present invention.

Bupivacaine-HCl is chemically designated as 2-piperidinecarboxamide, 1-butyl-N-(2,6-dimethylphenyl) monohydrochloride, monohydrate and is widely available commercially for pharmaceutical uses from many sources including from Astra Pharmaceutical Products Inc. (Westboro, Mass.) and Sanofi Winthrop Pharmaceuticals (New York, N.Y.), Eastman Kodak (Rochester, N.Y.). Bupivacaine is commercially formulated with and without methylparaben and with or without epinephrine. Any such formulation may be used. It is commercially available for pharmaceutical use in concentration of 0.25%, 0.5% and 0.75% which may be used on the invention. Alternative concentrations which elicit desirable effects may be prepared if desired. According to the present invention, about 250 µg to about 10 mg of bupivacaine is administered.

In some embodiments, about 250 µg to about 7.5 mg is administered. In some embodiments, about 0.50 mg to about 5.0 mg is administered. In some embodiments, about 1.0 mg to about 3.0 mg is administered. In some embodiments about 5.0 mg is administered. For example, in some embodiments about 50 µl to about 2 ml, preferably 50 µl to about 1500 µl and more preferably about 1 ml of 0.5% bupivacaine-HCl and 0.1% methylparaben in an isotonic pharmaceutical carrier is administered at the same site as the vaccine before, simultaneously with or after the vaccine is administered. similarly, in some embodiments, about 50 µl to about 2 ml, preferably 50 µl to about 1500 µl and more preferably about 1 ml of 0.5% bupivacaine-HCl in an isotonic pharmaceutical carrier is administered at the same site as the vaccine before, simultaneously with or after the vaccine is administered. Bupivacaine and any other similarly acting compounds, particularly those of the related family of local anesthetics may be administered at concentrations which provide the desired facilitation of uptake of genetic constructs by cells.

In some embodiments of the invention, the individual is first subject to bupivacaine injection prior to genetic vaccination by intramuscular injection. That is, up to, for example, up to a about a week to ten days prior to vaccination, the individual is first injected with bupivacaine. In some embodiments, prior to vaccination, the individual is injected with bupivacaine about 1 to 5 days before administration of the genetic construct. In some embodiments, prior to vaccination, the individual is injected with bupivacaine about 24 hrs before administration of the genetic construct. Alternatively, bupivacaine can be injected simultaneously, minutes before or after vaccination. Accordingly, bupivacaine and the genetic construct may be combined and injected simultaneously as a mixture. In some embodiments, the bupivacaine is administered after administration of the genetic construct. For example, up to about a week to ten days after administration of the genetic construct, the individual is injected with bupivacaine. In some embodiments, the individual is injected with bupivacaine about 24 hrs after vaccination. In some embodiments, the individual is injected with bupivacaine about 1 to 5 days after vaccination. In some embodiments, the individual is administered bupivacaine up to about a week to ten days after vaccination.

In addition to bupivacaine, mepivacaine, lidocaine, procaine, carbocaine and methyl bupivacaine, other similarly acting compounds may be used as response enhancing agents. Such agents acts a cell stiumulating agents which promote the uptake of genetic constructs into the cell and stimulate cell replication as well as initiate an inflammatory response at the site of administration.

Other contemplated response enhancing agents which may function transfecting agents and/or replicating agents and/or inflammatory agents and which may be co-adminstered with bupivacaine and similar acting compounds include lectins, growth factors, cytokines and lymphokines such as α-interferon, gamma-interferon, platelet derived growth factor (PDGF), gCSF, gMCSF, TNF, epidermal growth factor (EGF), IL-1, IL-2, IL-4, IL-6, IL-8, IL-10 and IL-12 as well as collagenase, fibroblast growth factor, estrogen, dexamethasone, saponins, surface active agents such as immunestimulating complexes (ISCOMS), Freund's incomplete adjuvant, LPS analog including monophosphoryl Lipid A (MPL), muramyl peptides, quinone analogs and vesicles such as squalene and squalane, hyaluronic acid and hyaluronidase may also be used administered in conjunction with the genetic construct. In some embodiments, combinations of these agents are administered in conjunction with bupivicaine and the genetic construct. For example, bupivacaine and either hyaluronic acid or hyaluronidase are co-administered with a genetic construct.

The genetic construct may be combined with collagen as an emulsion and delivered parenterally. The collagen emulsion provides a means for sustained release of DNA. 50 µl to 2 ml of collagen are used. About 100 µg DNA are combined with 1 ml of collagen in a preferred embodiment using this formulation.

In some embodiments of the invention, the genetic construct is injected with a needleless injection device. The needleless injection devices are particularly useful for simultaneous administration of the material intramuscularly, intradermally and subcutaneously.

In some embodiments of the invention, the genetic construct is administered with a response enhancing agent by means of a microprojectile particle bombardment procedure as taught by Sanford et al. in U.S. Pat. No. 4,945,050 issued Jul. 31, 1990, which is incorporated herein by reference.

In some embodiments of the invention, the genetic construct is administered as part of a liposome complex with a response enhancing agent.

In some embodiments of the invention, the individual is subject to a single vaccination to produce a full, broad immune response. In some embodiments of the invention, the individual is subject to a series of vaccinations to produce a full, broad immune response. According to some embodiments of the invention, at least two and preferably four to five injections are given over a period of time. The period of time between injections may include from 24 hours apart to two weeks or longer between injections, preferably one week apart. Alternatively, at least two and up to four separate injections are given simultaneously at different sites.

In some embodiments of the invention, a complete vaccination includes injection of a single inoculant which contains a genetic construct including sequences encoding one or more targeted epitopes.

In some embodiments of the invention, a complete vaccination includes injection of two or more different inoculants into different sites. For example, in an HIV vaccine according to the invention, the vaccine comprises two inoculants in which each one comprises genetic material encoding different viral proteins. This method of vaccination allows the introduction of as much as a complete set of viral genes into the individual without the risk of assembling an infectious viral particle. Thus, an immune response against most or all of the virus can be invoked in the vaccinated individual. Injection of each inoculant is performed at different sites, preferably at a distance to ensure no cells receive both genetic constructs. As a further safety precaution, some genes may be deleted or altered to further prevent the capability of infectious viral assembly. As used herein, the term "pharmaceutical kit" is meant to collectively refer to multiple inoculant used in the present invention. Such kits include separate containers containing different inoculants and/or cell stimulating agents. It is intended that these kits be provided to include a set of inoculants used in an immunizing method.

While the disclosure herein primarily relates to uses of the methods of the present invention to immunize humans, the methods of the present invention can be applied to veterinary medical uses too. It is within the scope of the present invention to provide methods of immunizing non-human as well as human individuals against pathogens and protein specific disorders and diseases. Accordingly, the present invention relates to genetic immunization of mammals, birds and fish. The methods of the present invention can be particularly useful for mammalian species including human, bovine, ovine, porcine, equine, canine and feline species.

While this disclosure generally discusses immunization in the context of prophylactic methods of protection, the term "immunizing" is meant to refer to both prophylactic and therapeutic methods. Thus, a method of immunizing includes both methods of protecting an individual from pathogen challenge or occurrence or proliferation of specific cells as well as methods of treating an individual suffering from pathogen infection, hyperproliferative disease or autoimmune disease. Accordingly, the present invention may be used as a vaccine for prophylactic protection or in a therapeutic manner; that is, as immunotherapeutic methods and preparations.

Other aspects of the invention include the use of bupivacaine and related, similarly acting cell stimulating agents in methods of introducing therapeutic genes into cells of an individual. Thus, one aspect of the present invention relates gene therpy; that is, to methods of introducing nucleic acid molecules that encode therapeutic proteins into the cells of an individual. The administration protocols and genecic constructs useful in gene therapy applications are the same as those described above for genetic immunization except the genetic constructs include nucleotide sequences that encode proteins whose presence in the individual will eliminate a deficiency in the individual and/or whose presence will provide a therapeutic effect on the individual.

The Examples set out below include representative examples of aspects of the present invention. The Examples are not meant to limit the scope of the invention but rather serve exemplary purposes. In addition, various aspects of the invention can be summarized by the following description. However, this description is not meant to limit the scope of the invention but rather to highlight various aspects of the invention. One having ordinary skill in the art can readily appreciate additional aspects and embodiments of the invention.

EXAMPLES

Example 1

According to the present invention, an effective vaccine has been produced which can invoke a protective immune response against HIV infected cells as well as cell free virus. As the awareness of AIDS and HIV infection has grown, repeated attempts and vast expenditures of resources and efforts have been made to produce an HIV vaccine. Despite enormous efforts, little progress has been made thus far and the long felt need for an HIV vaccine has gone unabated.

The present invention provides an HIV vaccine using direct genetic immunization. Genetic constructs are provided which, when delivered into the cells of an individual, are expressed to produce HIV proteins. According to some embodiments, the production of all viral structural proteins in the cells of the individual elicit a protective immune response which protects against HIV infection. The HIV vaccine of the present invention may be used to immunize uninfected individuals from HIV infection or serve as an immunotherapeutic for those individuals already infected. The HIV vaccine of the present invention invokes an immune response including CTLs which recognize and attack HIV infected cells and recognize the widest contingent of HIV protein. Thus, uninfected individuals are protected from HIV infection.

In some embodiments, the present invention relates to a method of immunizing an individual against HIV by administering two inoculants. These two inoculants comprise at least two and preferably more than two, a plurality or all of the genes of the HIV virus. However, the inoculants are not delivered together. Accordingly, an inoculated cell will not be administered a complete complement of genes. The vaccinated individual will receive at least two different and preferably more than two, more preferably a plurality or all of the viral genes. Immune responses can then be directed at the total complement of HIV protein target.

This strategy serves two purposes. First, it is unknown which target protein is most effective as an immunizing antigen to protect an individual against infection. Thus, immunizing with two or more provides a greater probability that the vaccinated individual will be provided with sufficient immunogenic target proteins for eliciting a protective immune response. Secondly, HIV proteins are known to undergo structural changes due to mutation. By providing multiple antigenic targets, the probability that a viral particle will escape detection by the immune response is reduced despite structural changes in one or more viral proteins. Accordingly, it is desirable to vaccinate an individual with multiple and preferably a nearly complete or complete complement of genes encoding viral proteins.

If a single cell is provided with a complete complement of viral genes, it is possible that a complete infectious virus can be assembled within the cell. Accordingly, a genetic construct according to the present invention is not provided with such a full complement of genes. Furthermore, two or more inoculants, each having an incomplete set of genes and combined having up to a full complement of viral genes, are administered to different cells, preferably at a distant site from each other to ensure that no vaccinated cell will inadvertently be exposed to a full set of genes. For example, a portion of the HIV genome may be inserted into a first construct and the remaining portion of the HIV genome is inserted in a second construct. The first construct is administered to an individual as a genetic vaccine in the muscle tissue of one arm while the second construct is administered to an individual as a genetic vaccine in the muscle tissue of the individual's other arm. The individual may be exposed to a full set of viral genes; thus essentially vaccinating against the whole virus but with no risk that an infectious viral particle will be assembled.

As an additional safety precaution, even when genetic material is delivered by two or more inoculants at distant parts of the individual's body, one or more essential genes can be deleted or intentionally altered to further ensure that an infectious viral particle cannot be formed. In such embodiments, the individual is not administered a complete functional set of viral genes.

A further safety precaution provides non-overlapping portions of the viral genome on the separate genetic constructs that make up the separate inoculants respectively. Accordingly, recombination between the two genetic constructs is prevented.

In some embodiments of the present invention, a full complement of structural genes are provided. The structural genes of HIV consist of gag, pol and env. These three genes are provided on two different DNA or RNA constructs. Accordingly, in one preferred embodiment, gag and pol are on one DNA or RNA construct and env is on another. In another preferred embodiment, gag is on one DNA or RNA construct and pol and env is on the other. In another preferred embodiment, gag and env are on one DNA or RNA construct and pol is on the other. Optionally, in any of these combinations, HIV regulatory genes may also be present. The HIV regulatory genes are: vpr, vif, vpu, nef, tat and rev.

The DNA construct in a preferred embodiment consists of a promoter, an enhancer and a polyadenylation signal. The promoter may be selected from the group consisting of: HIV LTR, human Actin, human Myosin, CMV, RSV, Moloney, MMTV, human Hemoglobin, human muscle creatine and EBV. The enhancer may be selected from the group consisting of: human Actin, human Myosin, CMV, RSV, human Hemoglobin, human muscle creatine and EBV. The polyadenylation signal may be selected from the group consisting of: LTR polyadenylation signal and SV40 polyadenylation signal, particularly the SV40 minor polyadenylation signal among others.

In some embodiments, the two inoculant vaccine is administered intramuscularly at spatially segregated tissue of the individual, preferably in different appendages, such as for example in the right and left arms. Each inoculant of the present invention may contain from about 0.1 to about 1000 micrograms of DNA. Preferably, each inoculant contains about 1 to about 500 micrograms of DNA. More preferably, each inoculant contains about 25 to about 250 micrograms of DNA. Most preferably, each inoculant contains about 100 micrograms DNA.

The inoculant in a preferred embodiment is in a sterile isotonic carrier, preferably phosphate buffered saline or saline solution.

In some embodiments, prior to vaccine administration, the tissue to be vaccinated is injected with a cell proliferating agent, preferably bupivacaine. Bupivacaine injections may be performed up to about 24 hours prior to vaccination. It is contemplated that bupivacaine injection will occur immediately before vaccination. About 50 µl to about 2 ml of 0.5% bupivacaine-HCl and 0.1% methylparaben in isotonic NaCl is administered to the site where the vaccine is to be administered, preferably, 50 µl to about 1500 µl, more preferably about 1 ml.

In other embodiments, a cell proliferating agent, preferably bupivacaine is included in the formulation together with the genetic construct. About 50 µl to about 2 ml of 0.5% bupivacaine-HCl and 0.1% methylparaben in isotonic NaCl is administered to the site where the vaccine is to be administered, preferably, 50 µl to about 1500 µl, more preferably about 1 ml.

Accordingly, some embodiments comprise a two inoculant vaccine: one inoculant comprising a DNA or RNA construct having two HIV structural genes, the other inoculant comprising a DNA or RNA construct having the third, remaining HIV structural gene such that the combined inoculants contain a full complement of HIV structural genes. The structural genes on each DNA construct are operably linked to a promoter, an enhancer and a polyadenylation signal. The same or different regulatory elements may control expression of the viral genes. When vaccinating an individual, the two inoculants are administered intramuscularly to different sites, preferably on different arms. In some embodiments of the invention, bupivacaine is first administered at the site where inoculant is to be administered. In some embodiments of the invention, bupivacaine is included in the formulations together with the genetic constructs.

In some embodiments, the vaccination procedure is repeated at least once and preferably two or three times. Each vaccination procedure is performed from 24 hours to two months apart.

In some embodiments, the vaccine is administered using a needleless injection device. In some embodiments, the vaccine is administered hypodermically using a needleless injection device thus providing intramuscular, intradermal, subcutaneous administration simultaneously while also administering the material interstitially.

Preferred genetic constructs include the following. Plasmids and Cloning Strategies:

Two plasmids were constructed: one which contains HIV gag/pol and the other which contains HIV env.

The HIV-1 genomic clone pNL43 was obtained through the NIH AIDS Research and Reference Reagent Program (ARRRP), Division of AIDS, NIAID, NIH, from Dr. Malcom Martin, and can be used as the starting material for HIV-1 viral genes for genetic constructs. Alternatively, any HIV molecular clone of infected cell can, through use of the polymerase chain technology, be modified sufficiently for construction including the HXB2 clone the MN clone as well as the SF or BAL-1 clone. The pNL43 clone is a construct that consists of HIV-1 proviral DNA plus 3 kb of host sequence from the site of integration cloned into PUC18.

Construction of pNL-puro-env plasmid

This plasmid was constructed for expression of gag pol. The StuI site within the non-HIV 5' flanking human DNA of pNL43 was destroyed by partial digestion with StuI followed by digestion of the free ends with E. coli polymerase 1. The linear plasmid was filled and then self ligated, leaving a unique StuI site within the HIV genome. This plasmid, pNLDstu, was then digested with the blunting enzymes StuI and BsaBI which eliminated a large section of the coding sequence for gp120. The SV40 promoter and puromycin resistance coding region (puromycin acetyl transferase (PAC)) were isolated from pBABE-puro (Morgenstern and Land, 1990 Nucl. Acids Res. 18(12):3587–3596, which is incorporated herein by reference, kindly provided by Dr. Hartmut Land of the Imperial Cancer Research Fund) using EcoRI and ClaI. This fragment was blunted, then cloned into the StuI/BsaBI-digested pNLDstu. A clone was selected with the SV40-puro fragment in the correct orientation so that the 3' LTR of HIV could provide poly A functions for the PAC message. This plasmid was designated pNLpuro.

Cloning strategy for deletion of vpr regulatory gene from the HIV gag pol vector A region from just upstream of the unique PflMI site to just after the vif termination codon was amplified via PCR using primers that introduced a non-conservative amino acid change (glu-→val) at amino acid 22 of vpr, a stop codon in the vpr reading frame immediately after amino acid 22, and an EcoRI site immediately following the new stop codon. This PCR fragment was substituted for the PflMI-EcoR I fragment of pNLpuro or pNL43. This substitution resulted in the deletion of 122 nucleotides of the open reading frame of vpr, thus eliminating the possibility of reversion that a point mutation strategy entails. The resulting plasmids, pNLpuroΔvpr, encode the first 21 natural amino acids of vpr plus a valine plus all other remaining HIV-1 genes and splice junctions in their native form. Such deletion strategy would also be applicable to nef, vif, and vpu and allow for structural gene expression but protect from the generation of a live recombinant virus. Plasmid construction for envelope expression:

The DNA segment encoding the envelope gene of HIV-1 HXB2 was cloned by the polymerase chain reaction (PCR) amplification technique utilizing the lambda cloned DNA obtained from the AIDS Research and Reference Reagent Program. The sequences of the 5' and 3' primers are 5'-AGGCGTCTCGAGACAGAGGAGAGCAAGAAATG-3' (SEQ ID NO: 1) with incorporation of XhoI site and 5'-TTTCCCTCTAGATAAGCCATCCAATCACAC-3' (SEQ ID NO: 2) with incorporation of XbaI site, respectively, which encompass gp160, tat and rev coding region. Gene specific amplification was performed using Taq DNA polymerase according to the manufacturer's instructions (Perkin-Elmer Cetus Corp.). The PCR reaction products were treated with 0.5 ug/ml proteinase K at 37° C. for thirty minutes followed by a phenol/chloroform extraction and ethanol precipitation. Recovered DNA was then digested with XhoI and XbaI for two hours at 37° C. and subjected to agarose gel electrophoresis. The isolated and purified XhoI-XbaI PCR fragment was cloned into Bluescript plasmid (Stratagene Inc., La Jolla, Calif.) and then subcloned into the eukaryotic expression vector pMAMneoBlue (Clontech Laboratories, Inc., Palo Alto, Calif.). The resulting construct was designated as pM160. The plasmid DNA was purified with CsCl gradient ultracentrifugation. An alternative envelope expression plasmid construction called HIV-1 env-rev plasmid:

The region encoding the two exons of rev and the vpu and envelope open reading frames of HIV-1 HXB2 was amplified via PCR and cloned into the expression vector pCNDA/neo (Invitrogen). This plasmid drives envelope production through the CMV promoter.

Production and Purification

The plasmid in *E. coli* (DH5 alpha) is grown up as follows: An LB plus ampicillin agar plate is streaked with the desired plasmid culture from frozen stock. The plate is incubated overnight (14–15 hours) at 37° C. A single colony is taken from the plate and inoculated into 15 ml of LB medium with a peptone preparation and 50 μg/ml ampicillin. This culture is grown at 37° C. while being shaken (ca. 175 rpm) for 8–10 hours. $OD_{600}$ readings should be at least 1.0. 1 liter of LB medium with peptone and 50 μg/ml ampicillin is inoculated with 1.0 OD of culture. These 1–2 liter cultures are grown overnight at 37° C. while being shaken (175 rpm).

Plasmid grown in *E. coli* (strain DH5 alpha) are harvested and purified by the following methods. General procedures for the lysis of cells and purification of plasmid can be found in "Molecular Cloning: A Laboratory Manual", 2nd Edition, J. Sambrook, E. F. Fritsch, and T. Maniatis, Cold Spring Harbor Press, 1989. The cells are concentrated and washed with glucose-tris-EDTA pH 8.0 buffer. The concentrated cells are lysed by treatment with lysozyme and briefly treated with 0.2N KOH, the pH is then adjusted 5.5 with potassium acetate/acetic acid buffer. Insoluble material is removed by centrifugation. To the supernatant is added 2-propanol to precipitate the plasmid. The plasmid is redissolved in tris-EDTA buffer and further purified by phenol/chloroform extraction and an additional precipitation with 2-propanol.

Endotoxin can optionally be removed by a variety of methods including the following: specific adsorption by immobilized materials such as polymyxin ("Endotoxin removed from hemoglobin solution using polymyxin B-immobilized fibre (PMX-F). . . ", Tani et al., *Biomater. Artif. Cells Immobilization Biotechnol.* 20(2–4):457–62 (1992); "Efficient endotoxin removal with a new sanitizable affinity column: Affi-Prep Polymyxin", Issekutz, *J. Immunol. Methods* 61(3):275–81 (1983)); anti-endotoxin monoclonal antibodies, such as 8A1 and HA-1A™ (Centocor, Malvern, Pa.; "Human Monoclonal Antibody HA-1A Binds to Endotoxin via an Epitope in the Lipid A Domain of Lipopolysaccharide" Bogard et al. *J. Immunol.* 150(10):4438–4449 (1993); Rietschel et al., *Infect. Immunity* page 3863 (1993)); positively charged depth filters ("Depyrogenation by endotoxin removal with positively charged depth filter cartridge", Hou et al., *J. Parenter. Sci. Technol.* 44(4):204–9(July–August 1990)); poly(gamma-methyl L-glutamate) ("Removal of endotoxin from culture supernatant of *Bortedella pertussis* with aminated poly (gamma-methyl L-glutamate) spherical beads", Hirayama et al., *Chem. Pharm. Bull.* (Tokyo) 40(8):2106–9 (1992)); histidine ("Specific removal of endotoxin from protein solutions by immobilized histidine", Matsumae et al., *Biotechnol. Appl. Biochem.* 12: (2):129–40 (1990)); hydrophobic interaction columns and membranes (e.g., "Removal of endotoxin from protein solutions by phase separation using Triton X-114", Aida et al., *J. Immunol Methods* 132(2):191–5 (1990); "Novel endotoxin adsorbing materials, polymyxin-sepharose and polyporous polyethylene membrane for removal of endotoxin from dialysis systems", Umeda et al., *Biomater Artif Cells Artif Organs* 18(4):491–7 (1990); "The effect of hydrophobic interaction on endotoxin adsorption by polymeric affinity matrix", Hou et al., *Biochem. Biophys. Acta* 1073(1):149–54 (1991); "Endotoxin removal from water using microporous polyethylene chopped fibres as a new adsorbent", Sawada et al., *J. Hyg.* (London) 97(1):103–14 (1986)); specific hydrophobic resins useful for removing endotoxin including hydrophobic polystyrene/divinylbenzene or divinylbenzene resins such as Brownlee Polypore Resin (Applied Biosystems, Palo Alto, Calif.); XUS 40323.00 (Dow Chemical, Midland, Mich.); HP20, CHP20P (Mitsubishi Kasei, U.S.); Hamilton PRP-1, PRP-infinity (Hamilton, Reno, Nev.); Jordi Reversed-Phase DVB, Jordi Gel DVB, Polymer Labs PLgel™ (Alltech, Deerfield, Ill.); Vydac PLx™ (Separations Group, Hesperia, Calif.); other endotoxin removing materials and methods include Detoxi-Gel™ Endotoxin Removing Gel (Pierce Chemical, Rockford, Ill.); Application Note 206, "Chromatographic removal of endotoxins and/or ethanol from albumin", (Pharmacia Biotech Inc, Piscataway, N.J.). See also generally, "Endotoxin Detection and Elimination in Biotechnology", Sharma, *Biotech. App. Biochem.* 8:5–22 (1986).

Preferred anti-endotoxin monoclonal antibodies bind to the conserved domains of endotoxin, preferably antibodies to lipid A, the most structurally conserved portion of the endotoxin molecule. Such anti-lipid A monoclonal antibodies include the high affinity murine IgG monoclonal antibody 8A1 and the human anti-lipid A IgM(k) monoclonal antibody HA-1A™. HA-1™ was derived from a human B *E. coli* J5 vaccine. HA-1A ™. HA-1A ™ is reported to be broadly cross-reactive with a variety of bacterial endotoxins (lipopolysaccharides).

Example 2

In experiments designed to compare the immunogenic response elicited by genetic vaccination and protein vaccination, animal models were designed using tumor cells that specifically express a foreign target protein. Three immune competent mouse models have been developed which express foreign antigens. Three clonal tumor cell lines which are derived from the Balb/c mouse strain are used. The cell lines are: 1) a lymphoid cell line which does not metastasize significantly to other tissues but forms large palpable tumors which appear to kill the animal within an 8–12 week period; 2) a murine melanoma cell line with some ability to metastasize, mostly to the lung, and in which, following inoculation with 1 million cells, results in the development in the mice of large palpable tumors which similarly kill the animal within 10–12 weeks; and 3) a murine lung adenocarcinoma cell line which metastasizes to multiple tissues and kills the animal within 12 or more weeks. Subclones have been selected which can display foreign antigens in an unrecognized form. When transfected tumors are implanted into a parent mouse strain, unlike the majority of similar murine tumor lines, the animals do not make a protective immune response to the foreign antigens displayed and the tumors are accepted. These tumors then kill the animal with the same phenotype in the same time frame as the original untransfected tumor. Using these models, the immune response elicited by genetic vaccination against an antigen can be measured.

It was observed that mice vaccinated with a genetic vaccine comprising a genetic construct that resulted in production of the target protein by the cell's of the mouse elicited an immune response including a strong cytotoxic that completely eliminated tumors displaying the target protein but with no effect on tumors that did not. In mice inoculated with the target protein itself, the immune response elicited thereby was much less effective. The tumors were reduced in size but, due to an absence of a cytotoxic response, they were not eliminated. As controls, untransfected tumors were used in experiments comparing the immune response of animals vaccinated with the genetic vaccine, subunit vaccine and unvaccinated animals. These experiments clearly demonstrate that the genetic vaccine produced a broader, more effective immune response which was capable, by virtue of CTL's, of completely eliminating tumors. By contrast, immunization using intact target protein produced a more limited, less effective immune response.

Example 3

In some embodiments of the invention, the infectious virus, HIV, which is responsible for AIDS is the pathogenic agent against which a genetic vaccine has been designed. The viral protein gp160, which is processed into gp120 and gp41, is the target protein against which a genetic vaccine is produced. The genetic vaccine contains a DNA construct that comprises a DNA sequence encoding gp160 operably linked regulatory elements. When administered to an individual, the DNA construct of the genetic vaccine is incorporated into the cells of the individual and gp160 is produced. The immune response that is elicited by the protein is broad based and includes the humoral and both arms of the cellular immune response. The broad biological response provides superior protection to that achieved when the protein itself is administered.

The following is a description of the use of genetic immunization for elicitation of an anti-human immunodeficiency virus type 1 (HIV-1) immune response in mice by administering a DNA construct that contains a DNA sequence which encodes the HIV envelope glycoprotein gp160. The gp160 construct (pM160) expresses biologically active HIV-1 envelope proteins in vivo.

Mice were injected intramuscularly with pM160 and subsequently analyzed for anti-HIV immune responses. The antisera from animals immunized in this manner produce anti-HIV envelope glycoprotein immune responses as measured by enzyme linked immunosorbent assay (ELISA) and immunoprecipitation assays. The antisera neutralizes HIV-1 infection and inhibits HIV-1 induced syncytium formation.

The observed neutralization and anti-syncytial activity may be the result of reactivity of the elicited antibodies to functionally important regions of the HIV-1 envelope protein, such as the V3 loop of gp120, CD4 binding site and the N-terminal "immunodominant" region of gp41, among others.

The DNA construct (pM160) encoding the HIV-1/HXB2 (Fisher, A. G., et al., (1985) *Nature* 316:262–265) gp160 membrane bound glycoprotein under control of a RSV enhancer element with the MMTV LTR as a promoter (FIG. 1A) was tested to determine whether this membrane-bound protein, when expressed by endogenous cells, can generate an anti-pathogen immune responses. The construct was generated as follows. The DNA segment encoding the envelope gene of HIV-1 HXB2 was cloned by the polymerase chain reaction (PCR) technique amplification utilizing the lambda cloned DNA obtained from eh AIDS repository. The sequences of the 5' and 3' primers are 5'-AGGCGTCTCGAGACAGAGGAGAGCAAGAAATG-3' (SEQ ID NO: 11) with incorporation of XhoI site and 5'-TTTCCCTCTAGATAAGCCATCCAATCACAC-3' (SEQ ID NO: 12) with incorporation of XbaI site, respectively, which encompass gp160, tat and rev coding region. Gene specific amplification was performed using Taq DNA polymerase according to manufacturer's instruction (Perkin-Elmer Cetus Corp.) The PCR reaction products were treated with 0.5 $\mu$g/ml proteinase K at 37° C. for thirty minutes followed by a phenol/chloroform extraction and ethanol precipitation (Crowe, J. S., et al., (1991) *Nucl. Acids Res.* 19:184). Recovered DNA was then digested with XhoI and XbaI for two hours at 37° C. and subjected to agarose gel electrophoresis. The isolated and purified XhoI-XbaI PCR fragment was cloned into Bluescript plasmid (Stratagene Inc., La Jolla, Calif.) and then subcloned into the eukaryotic expression vector pMAMneoBlue (Clontech, Inc.). The resulting construct was designated as pM160. The plasmid DNA was purified with CsCl purification (Sambrook, J. et al., (1989 *Molecular Cloning: A Laboratory Manual*, Cold Spring Harbor Laboratory Press, Cold Spring Harbor, N.Y.).

The pM160 construct, which contains a DNA sequence that encodes gp160, was transfected into a human rhabdomyosarcoma cell line, TE671 (Stratton, M. R., et al., (1989) *Carcinogenesis* 10:899–905), to evaluate its expression before introduction into living animals. Transfection of pM160 construct into TE671 cells was performed according to Wang, B., et al., (1992) *AIDS Human Retr.*, in press. Briefly, 2 $\mu$g of purified pM160 was added to $2\times10^6$ TE671 cells (Stratton, M. R., et al., (1989) *Carcinogenesis* 10:899–905) and subject to electroporation. Following electroporation, the cells were grown in fresh medium for forty eight hours prior to the addition of 500 $\mu$g/ml neomycin for selection. Individual cells expressing gp160 envelope protein were isolated by binding to M450 magnetic beads (Dynal) which was coated with mixture of monoclonal anti-gp120 antibodies, namely ID6, AD3 and AC4 (Ugen, K. E. et al., (1992) *Generation of Monoclonal Antibodies Against the Amino Region of gp120 Which Elicits Antibody Dependent Cellular Cytotoxicity*, Cold Spring Harbor Laboratory, 1992). Clones were isolated by limiting dilution of the gp160 expressing cells. One of such clone was designated as the 3G7 cell line. Expression of gp120 and gp41 was determined by Western blot analysis of whole cell lysates of 3G7 cells versus vector-alone transfected TE671 cells, performed as previously described (Osther, K., et al., (1989) *Transplantation* 47:834–8; and Weiner, D. B., et al., (1989) *Vaccines*, Cold Spring Harbor Press, 115–120).

Figure 1B:
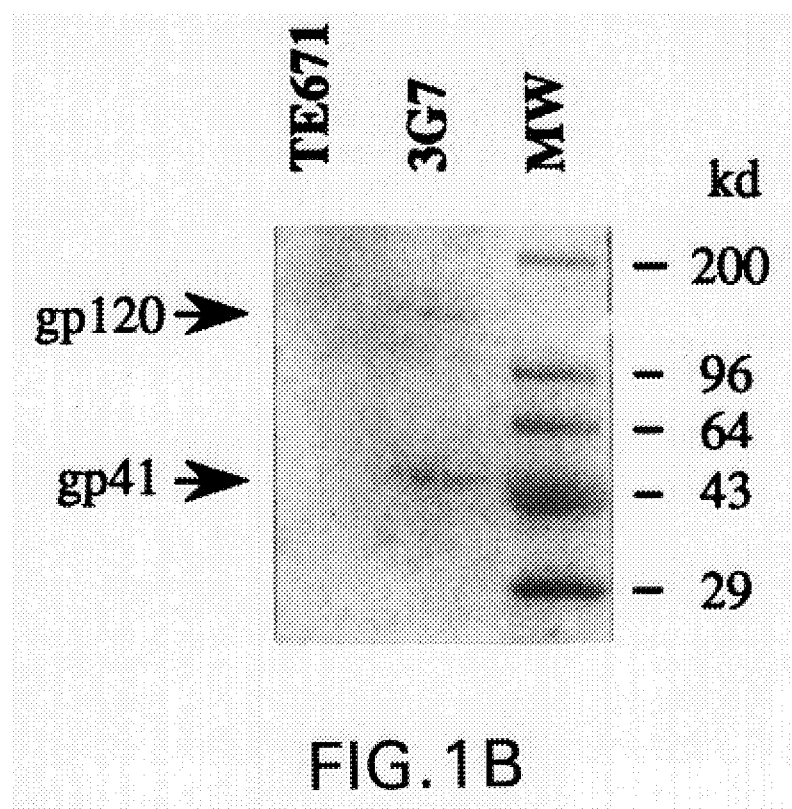
FIG. 1B is a photograph of an autoradiogram of a Western blot of whole cell lysates of cells transfected with the pM160 plasmid (3G7 cells) versus vector-alone transfected cells (TE671 cells) showing production of gp120 and gp41 in 3G7 cells and not in TE671 cells.

Typically, the mature HIV envelope glycoprotein gp160 is processed into gp120 and gp41 (Kowalski, M., et al., (1987) *Science* 237:1351–135). The expression of HIV gp120 and gp41 by the pM160 transfected cell line 3G7 were observed in Western blot analysis with anti-gp160 specific serum (Osther, K., et al., (1991) *Hybridoma* 10:673–683) (FIG. 1B). Functional expression of gp160 by this cell line was further demonstrated by the ability of 3G7 but not TE671 cells to fuse with several CD4+ T-cell cell lines.

In the genetic immunization procedure described herein, the quadriceps muscles of BALB/c mice were injected with 100 μl of 0.5% bupivacaine-HCl and 0.1% methylparaben in isotonic NaCl using a 27-gauge needle to stimulate muscle cell regeneration and facilitate uptake of the genetic construct. Twenty-four hours later, the same injection sites were then injected with either 100 μg of pM160 or with 100 μg of pMAMneoBlue as a control plasmid (FIG. 1A). The mice were boosted by injecting the same amount of DNA construct three times at two week intervals in the same manner but without pre-treatment with bupivacaine-HCl.

For the recombinant gp160 immunization, BALB/C mice were initially immunized with 1 μg of glycosylated recombinant (HIV-1I/III$_B$) gp160 (MicroGeneSys Inc.) in complete Freund's adjuvant followed by three boosters of 1 μg of gp160 each in incomplete Freund's adjuvant at two week intervals. The production of antibody against HIV-1 gp160 was determined by testing the mouse sera for their ability to immunoprecipitate gp160. Immunoprecipitation was performed using 1×10$^6$ cpm of $^{125}$I labeled rgp160, mouse sera and protein-G agarose beads (GIBCO, Inc.) as previously described by Osther, K., et al., (1991)*Hybridoma* 10:673–683, which is incorporated herein by reference. The specific precipitations were analyzed by 10% SDS-PAGE. Lane 1 is 1 μl of preimmune mouse serum reacted with the $^{125}$I-gp160. Lane 2 is 1 μl of mouse serum immunized from the pM160 immunized mice. Lane 3 is 1 μl of 1:100 dilution of ID6 monoclonal anti-gp120 antibody (Ugen, K. E., et al., (1992) *Generation of Monoclonal Antibodies Against the Amino Region of gp120 Which Elicits Antibody Dependent Cellular Cytotoxicity*, Cold Spring Harbor Laboratory) as a positive control. The arrow indicates the specifically immunoprecipitated $^{125}$I-gp160 envelope glycoprotein.

Figure 2:
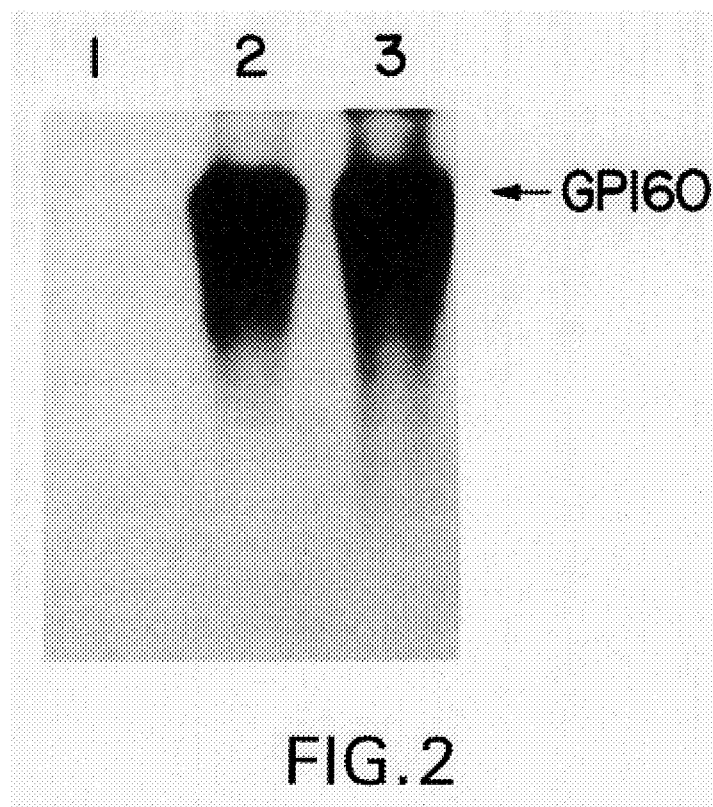
FIG. 2 is a photograph of an autoradiogram showing immunoprecipitations of serum antibodies binding to $^{125}$I-p160.

$^{125}$I-labelled gp160 was specifically immunoprecipitated with antisera derived from the pM160-immunized animals (FIG. 2, lane 2) as well as the positive control anti-gp120 monoclonal antibody, ID6 (FIG. 2, lane 3). In contrast, the preimmune sera (FIG. 2, lane 1) only showed minimal activity in the same assay.

Eight of ten mice immunized with the pM160 construct were positive for reactivity against gp160 as determined by ELISA and the immune responses from the animal with the highest anti-gp160 titer was analyzed in detail. Four mice immunized with the control vector all showed a similar negative reactivity to gp160 in ELISA and one of these sera was used as the control for subsequent experiments.

It has been shown that HIV neutralizing antibodies are specifically targeted to several epitopes in gp120 and gp41, which include the V3 loop in gp120 (Goudsmit, J. et al., (1988) *AIDS* 2:157–164; and Putney, S. D., et al., (1989) *Development Of An HIV Subunit Vaccine*, Montreal), the CD4 binding site near the carboxy terminus of gp120 (Lasky, L. A., et al., (1987) *Cell* 50:975–985) as well as the immunodominant loop of gp41 just downstream of the N-terminal fusion region (Schrier, R. D., et al., (1988) *J. Virol.* 62:2531–2536).

Figure 3A:
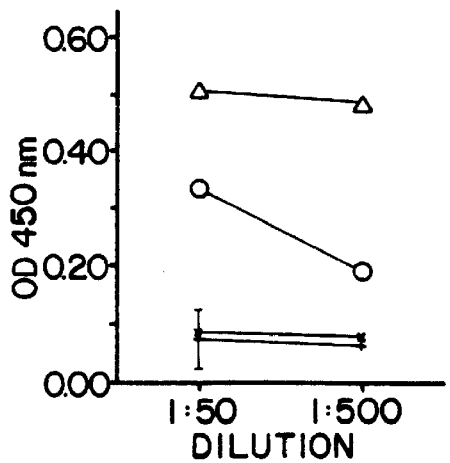
FIGS. 3A–3E are graphs showing ELISA results binding different sera to various proteins immobilized on microtiter plates.
Figure 3B:
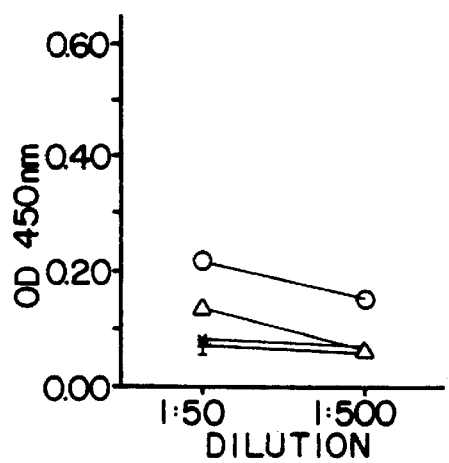
Figure 3C:
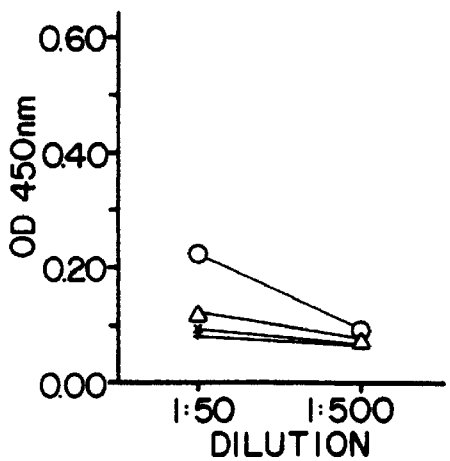
Figure 3D:
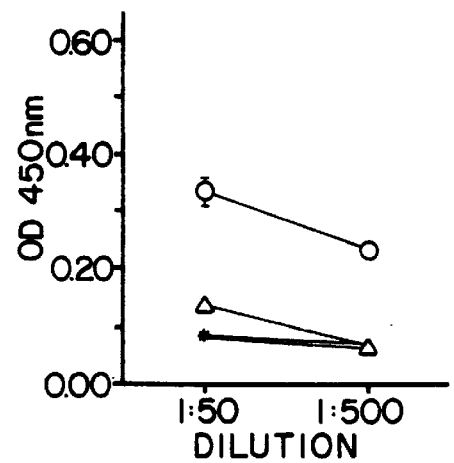
Figure 3E:
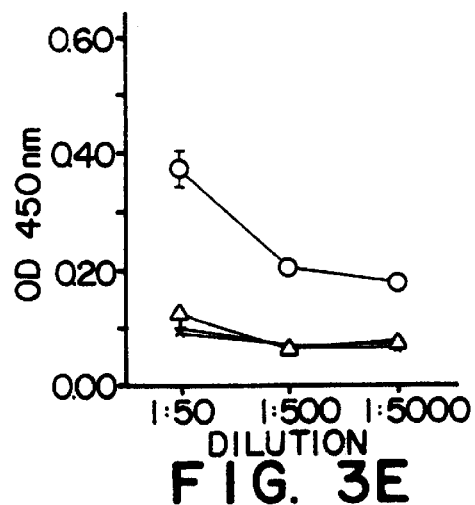

To determine whether the anti-gp160 antibodies elicited in these mice are reactive to these important regions of the envelope glycoproteins, peptides for the BRU/V3 loop, peptides for the MN/V3 loop, peptides for the HXB2/gp41 N-terminus or peptides for HXB2/CD4 binding site were absorbed to microtiter plates and specific reactivities of the mouse antisera determined in ELISA assays. One μg/ml of gp160 or 10 μg/ml of each peptide was coated to microtiter plates in 0.1M bicarbonate buffer (pH 9.5) overnight at 4° C., blocked with 2% bovine serum albumin in PBS, and reacted with goat anti-mouse IgG conjugated with HRPO (Fisher) for one hour at 37° C. and developed with TMB substrate (Sigma) for 10–30 minutes at room temperature in the dark. Results are reported in FIG. 3. Antisera were as follows: (-+-) is preimmune sera, (-x-) is the pMAMneoBlue vector immunized sera, (-O-) is the pM160 immunized sera, (-Δ-) is from mice immunized with the rgp160 protein. FIG. 3A shows results using a rgp160 protein coated plate. FIG. 3B shows results using a BRU/V3 loop peptides (CNTRKRIRIQRGPGRAFVTIGK (SEQ ID NO: 13)) coated plate. FIG. 3C shows results using a plate coated with MN/V loop peptides (YNKRKRIHIQRGPGRAFYTTKNIIC (SEQ ID NO: 14)) with the QR sequence from HIV-1l/III$_B$ in bold-faced type. FIG. 3D shows the results using a HXB2/CD4 binding site peptides (CRIKQFINMWQEVGKAMYAPPISGIRC (SEQ ID NO: 15)) coated plate. FIG. 3E shows the results using a BRU/gp41 immunodominant region peptides (RILAVERYIKDQQLLGIWGCSGKLIC (SEQ ID NO: 16)) coated plate.

For the recombinant gp160 immunization. BALB/C mice were initially immunized with 1 μg of glycosylated recombinant (HIV-1/III$_B$) gp160 (MicroGeneSys Inc.) in complete Freund's adjuvant followed by three boosters of 1 μg of gp160 each in incomplete Freund's adjuvant at two week intervals.

FIG. 3 shows that antiserum from the pM160 construct immunized mouse has significantly higher reactivity to the BRU and MN/V3 loop peptides, the CD4 binding site peptide and the immunodominant gp41 peptide than the recombinant gp160 protein (rgp160) immunized serum. Interestingly, the antiserum from the rgp160 immunized mouse had much higher titer against the rgp160 than the pM160 immunized antiserum, but lower activity against the three specific neutralization epitopes of gp160 tested (FIG. 3 a–d).

To determine whether the antisera generated by DNA immunization possessed antiviral activity, the ability of the antisera to neutralize HIV-1 infection was examined. Cell-free HIV-1/III$_B$ virus at 100 TCID$_{50}$ was incubated with serial dilutions of the antisera before being used to infect MT-2 target cells (Montefiori, D. C., (1988) *J. Clin. Microbio.* 26:231–235).

One hundred TCID$_{50}$HIV-1/III$_B$ cell-free virus was pre-incubated with serial dilutions of antisera for one hour at 37° C. Following incubation the pretreated virus was then plated on the 4×10⁴ of target cell line, MT-2 for one hour at 37° C., following infection the MT-2 cells were washed three times and then incubated at 37° C. at 5% $CO_2$. Fusion was evaluated three days later quantitatively by visually counting the number of syncytia per well in triplicate experiments under a phase contrast microscope.

The results are reported in FIG. 4. FIG. 4A shows the results using vector-immunized mouse sera compared with FIG. 4B which shows the results using pM160 immunized sera. Neutralization values ($V_n/V_o$) versus the dilution factors (Nara, P., (1989) *Techniques In HIV Research* eds. Aldovini, A. & Walkter, B. D., 77–86M Stockton Press) are illustrated in FIG. 4C. The control serum (-x) was from pMAMneoBlue vector immunized mice. The test sera (O) were from pM160 immunized mice.

Figure 4D:
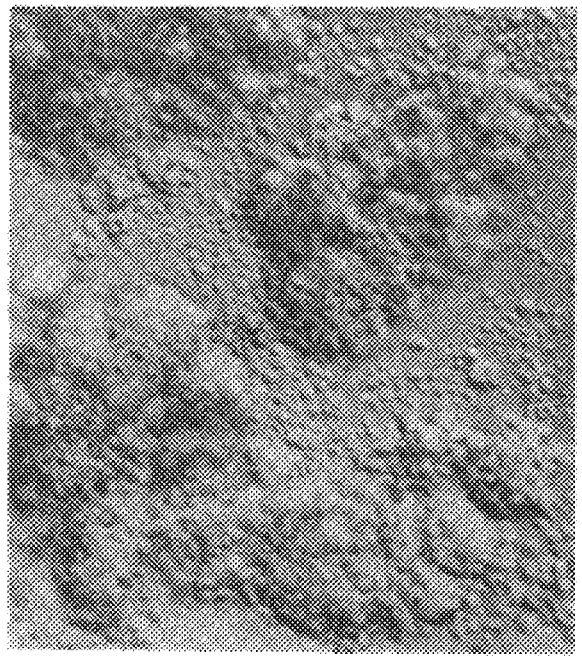
FIGS. 4D–4G are photographs of H9/III$_B$ cells used in experiments to examine syncytial inhibition using sera from immunized and control animals.
Figure 4E:
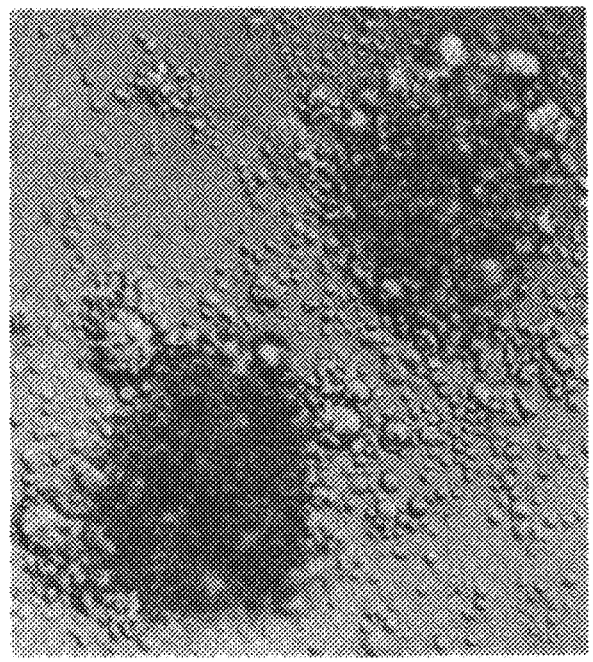
Figure 4F:
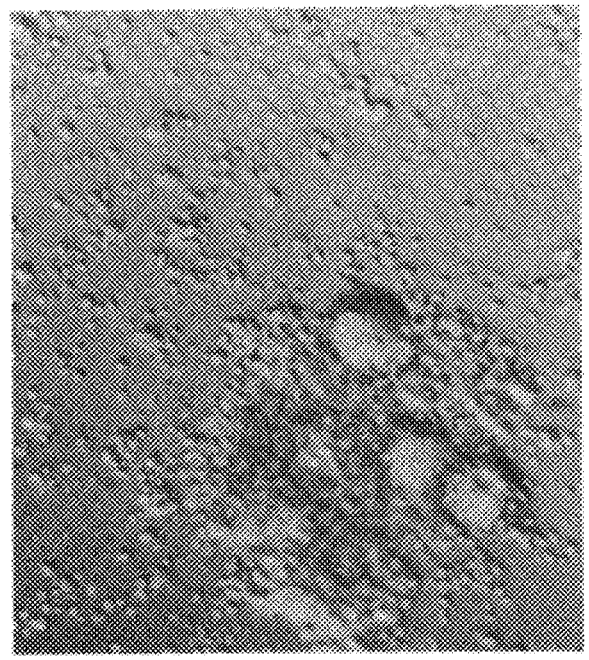
Figure 4G:
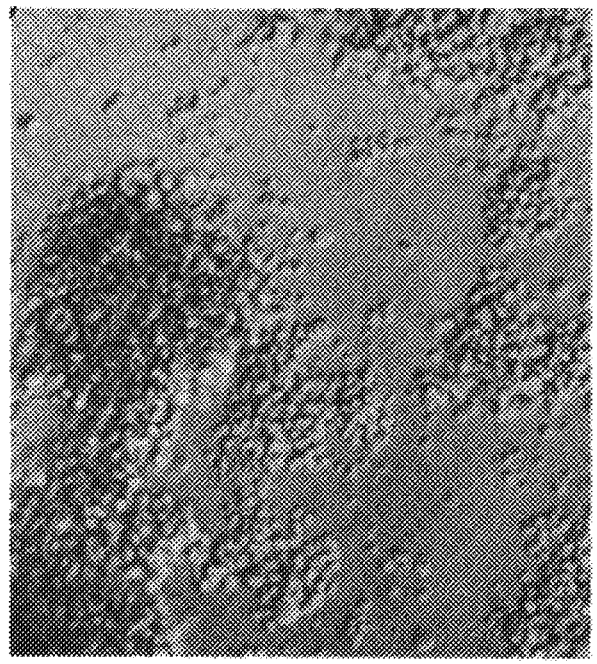
Figure 5:
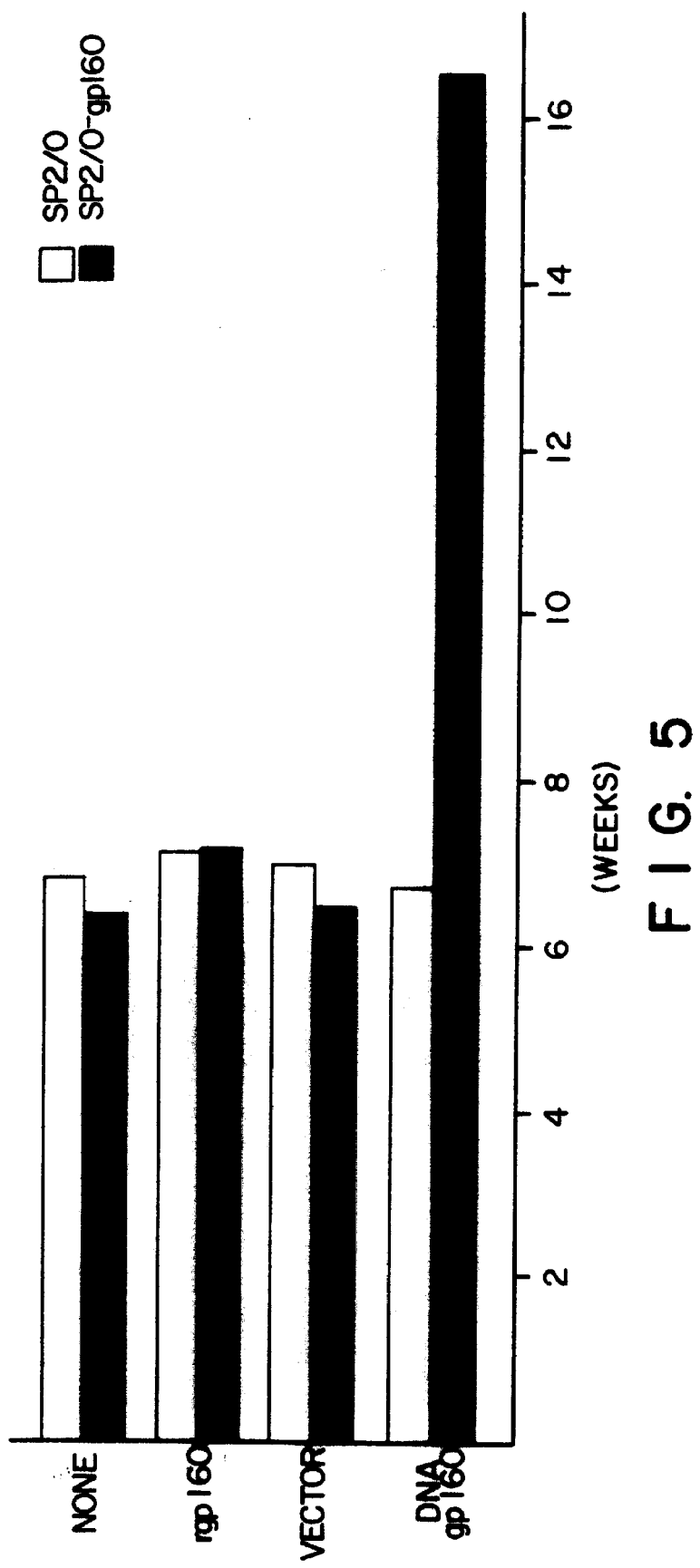
FIG. 5 is a chart depicting the survival of immunized and non-immunized mice challenged with HIV gp160-labelled and unlabelled tumor cells. Mice were immunized with recombinant gp160 protein, vector DNA only or recombinant vector comprising DNA encoding gp160. SP2/0 tumor cells or SP2/0-gp160 (SP2/0 cells transfected with DNA encoding gp160 and expressing gp160 ) tumor cells were introduced into the mice.
Figure 6:
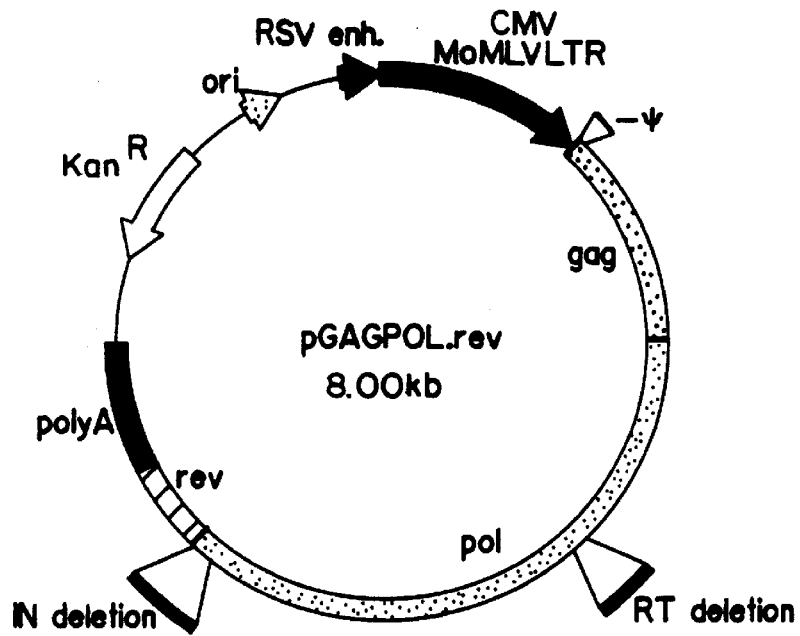
FIG. 6 is a plasmid map of pGAGPOL.rev.
Figure 7:
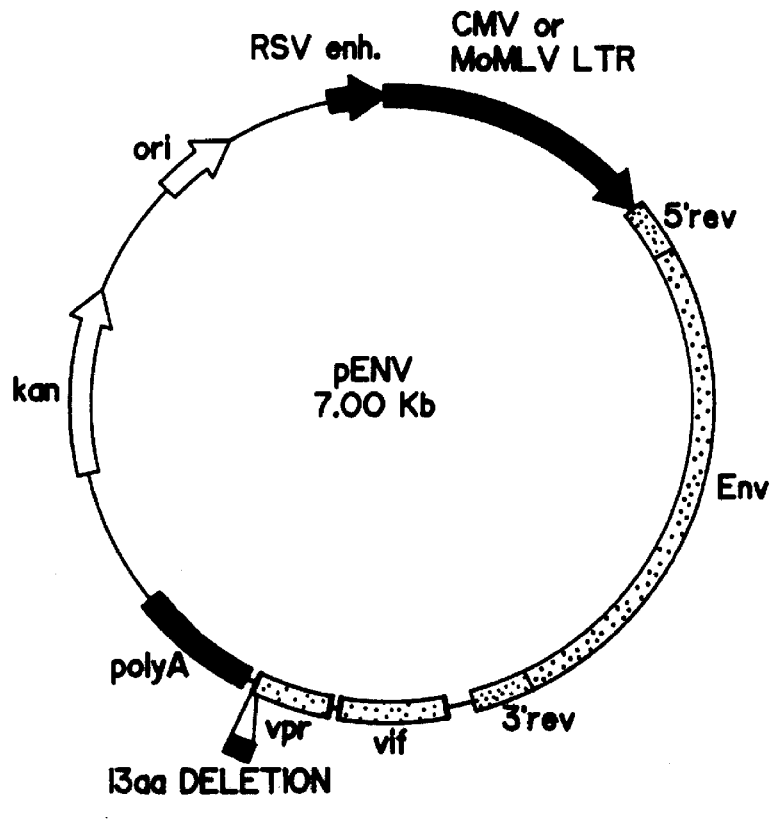
FIG. 7 is a plasmid map of pENV.
Figure 8A:
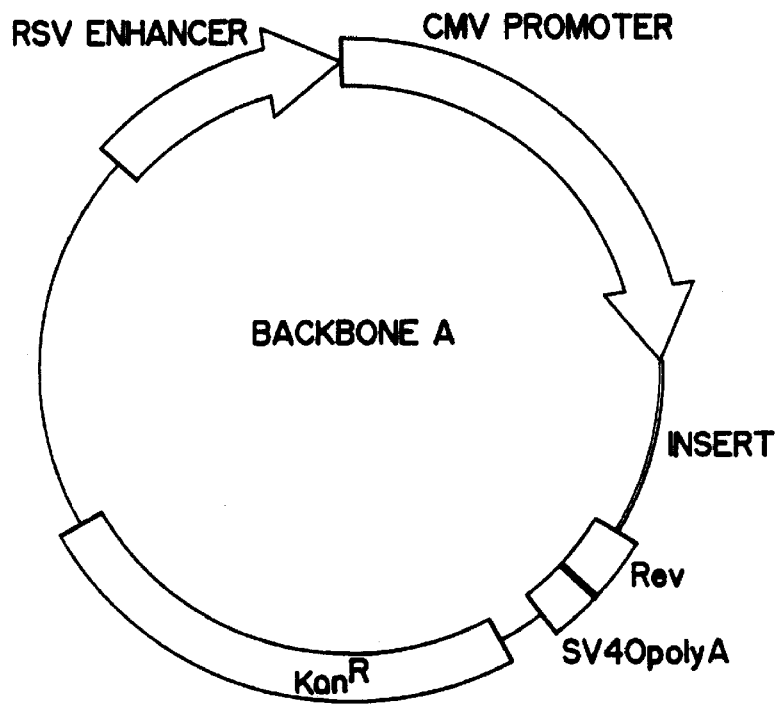
FIGS. 8A–8D is show four backbones, A, B, C and D, used to prepare genetic construct.
Figure 8B:
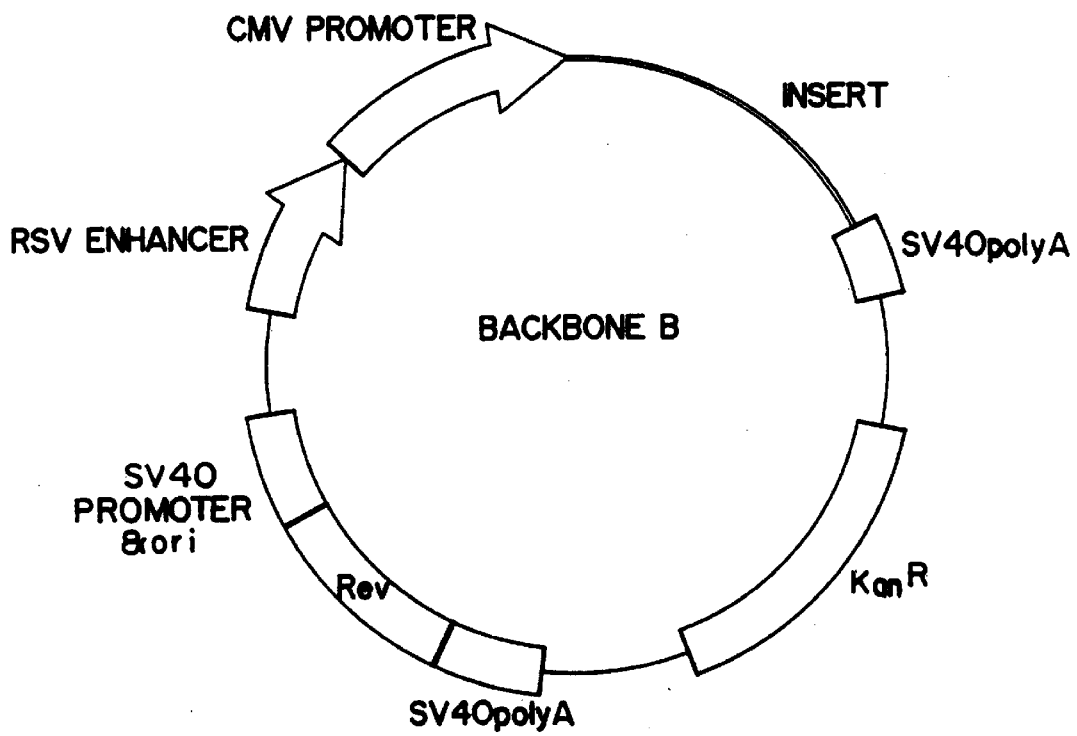
Figure 8C:
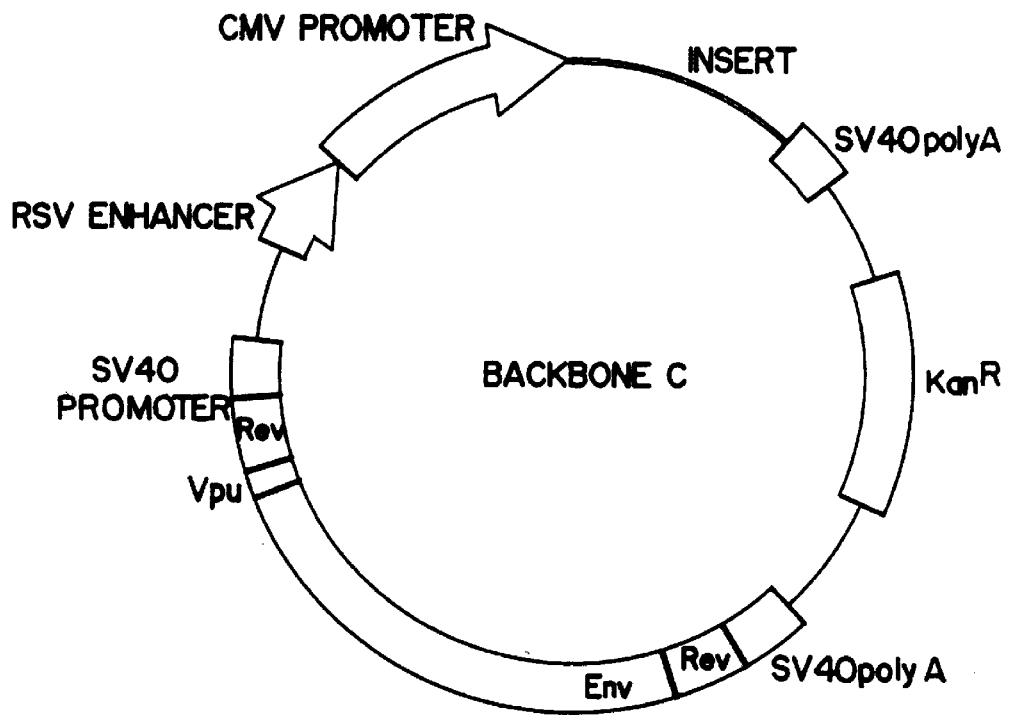
Figure 8D:
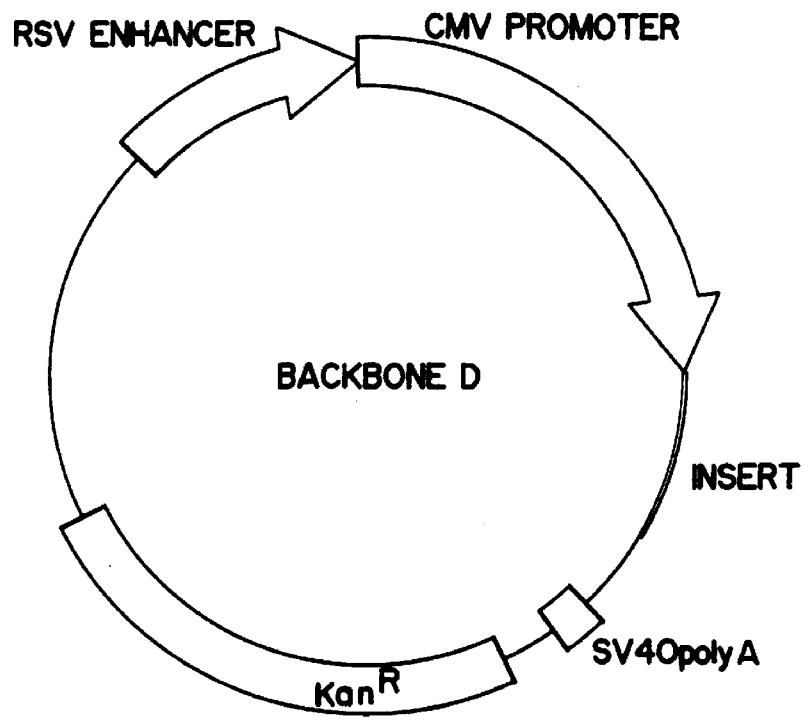
Figure 9:
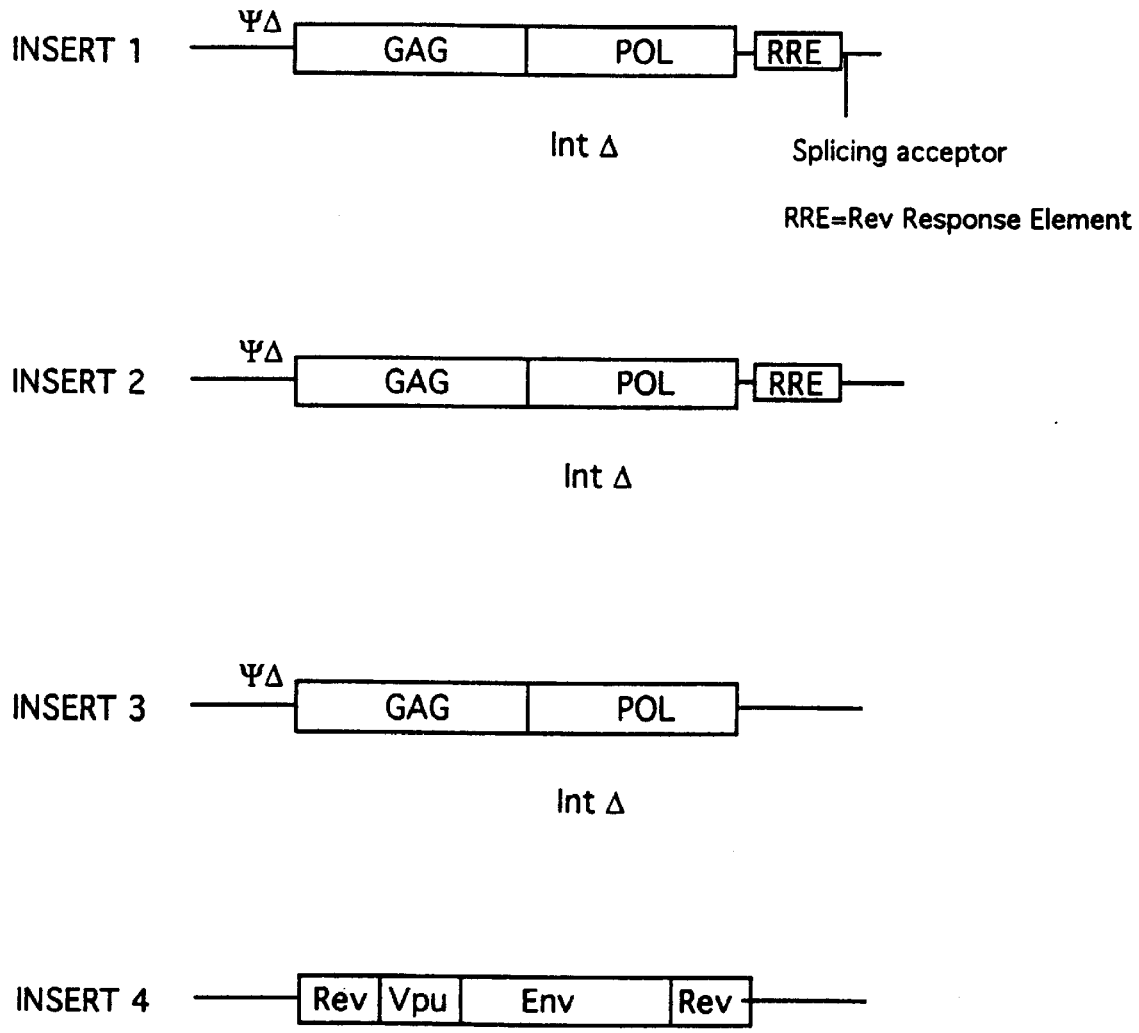
FIG. 9 shows four inserts, 1, 2, 3 and 4 which are inserted into backbones to produce genetic constructs.

Syncytia inhibition was performed as described by Osther, K., et al., (1991) *Hybridoma* 10:673–683. The H9/III$_B$ cell line was pre-incubated with serial dilutions (1:100, 1:200, and 1:400) of antisera were made in 96 well plates in a total volume of 50 μl for thirty minutes at 37° C. at 5% $CO_2$. Fusion was evaluated three days later quantitatively by visually counting the number of syncytia per well under a phase construct microscope. FIG. 4D is the target cells co-cultivated with HIV-1/III$_B$ cell line treated with preimmune serum. FIG. 4E is the same as FIG. 4D but treated with vector control immunized serum. FIG. 4F is the same as FIG. 4D but treated with rgp160 immunized serum. FIG. 4G is the same as FIG. 4D but treated with pM160 immunized serum. FIGS. 4D to 4G show that inhibition of syncytia was apparent at dilution at 1:200 in these assays. MT-2 cells were infected with cell-free HIV-1/III$_B$ which had been preincubated with vector-immunized antiserum readily formed syncytia (FIG. 4A). In comparison, preincubation with pM160 immunized mouse serum prevented syncytium formation (FIG. 4B). The neutralization kinetics were determined by $V_n/V_o$ versus serial dilutions of antisera (Nara, P., (1989) *Techniques In HIV Research*, eds. Aldovini, A. & Walker, B. D., 77–86, M Stockton Press) (FIG. 4C). The serum from the pM160 immunized mouse had biologically active neutralizing activity at dilutions of up to 1:320 while control antisera did not show similar activity.

To determine if the antiserum from the pM160 immunized mouse could inhibit envelope-mediated virus spread through direct cell-to-cell fusion, syncytium inhibition assays were performed. Antiserum from the pM160 immunized mouse inhibits HIV-1 induced syncytium formation at 1:200 dilutions (FIG. 4G). In contrast, the preimmune sera (FIG. 4D), antisera from the rgp160 immunized mice (FIG. 4F) and antisera from the control vector-immunized animals (FIG. 4E) failed to inhibit syncytium formation at the same dilutions.

Observations from the neutralization (FIGS. 4A–C) and syncytium inhibition assays (Figures D–G) of these sera correlates with the observed ELISA reactivities (FIG. 3). The antiserum from the pM160 immunized mouse which showed a high level of binding to neutralizing epitopes likewise demonstrated high level anti-viral activities; conversely, sera with little binding to these epitopes including the antiserum from rgp160 immunized mice have low anti-viral activity.

Low level neutralizing activity has been observed by other groups when using rgp160 immunization (Lasky, L. A. et al., (1986) *Science* 233:209–212; and Berman P. W., et al., (1990) *Nature* 345:622–625. The reasons for the more effective generation of anti-viral activities by the genetic immunization than by recombinant protein immunization are not clear. However, the differences in the generated immune responses may be due to the introduction of the gp160 gene directly into the mouse muscle cells and expression of this gene in vivo which may correctly process the products and lead to more effective processing of the target antigen.

HIV enters cells binding to the CD4 molecule found predominantly on human helper T-cells, macrophages, and possibly glial cells (Maddon, P. J., et al., (1986) *Cell* 47:333–348; Koenig, S., et al., (1986) *Science* 233:1089–1093; and Cheng-Mayer, C., et al., (1987) *Proc. Natl. Acad. Sci. USA* 84:3526–3530). Interruption of this binding has been shown to prevent HIV infection in vivo (Fisher, R. A., et al., (1988) *Nature* 331:76–78; and Sun, H. C., et al., 1989 *J. Virol.* 63:3579–85).

To test whether the antisera from pMl160 immunized mice can inhibit gp120 binding to CD4-bearing T-cells, a direct inhibition assay monitored by fluorocytometry was employed (Chen, Y. H., et al., (1992) *AIDS* 6:533–539. It was observed that serum from the pM160 construct-immunized mouse was able to block the binding of gp120 to CD4-bearing T-cells: a 1:15 dilution of immune serum inhibited FITC-gp120 binding to CD4⁺SupT1 cells by 22%±2% in replicate experiments as evaluated by flow cytometry. This indicates that this region for HIV entry into target cells can also be functionally inhibited by this antiserum. These data are consistent with observed ELISA reactivity of the antiserum to the CD4 binding site peptides (FIG. 3c).

Immunoglobulin isotyping studies were performed by using a commercial murine monoclonal antibody isotyping kit (Sigma). of the anti-gp160 specific antibodies elicited by pM160 immunization, 19% are IgG1, 51% are IgG2, 16% are IgG3, 10% are IgM and 5% are IgA. The predominance of IgG isotypes indicates that a secondary immune response has taken place, and further suggests that helper T-cells can be elicited by genetic immunization.

To determine whether immunization with the DNA construct can lead to the generation of anti-DNA antibodies in these experimental animals, pM160 and pMAMneoBlue DNAs were coated onto microtiter plates and specific binding was determined by ELISA using sera all immunized animals. No significant binding to plasmid DNA was observed. Thus, using genetic material for inoculation into muscle tissue appears unlikely to produce an anti-plasmid DNA response.

Introducing construct DNA into mouse muscle by needle injection may cause inconsistent results, as this technique does not provide a means to control DNA uptake by muscle cells. Injection of construct DNA alone (n≈4) with bupivacaine pretreated animals (n≈4) was compared. The immune responses observed in the two groups were dissimilar, with 25% and 75% animals responding in ELISA assays respectively. Increased efficiency may be achieved by use of a direct DNA delivery system such as particle bombardment (Klein, T. M. et al., (1992) *Bio/technology* 10:286–291.

Evidence of neutralization, syncytia inhibition, inhibition of CD4-gp120 binding, and specific binding to several important regions on the gp160 demonstrate that introduction of a DNA construct encoding HIV gp160 membrane-bound glycoprotein directly into muscle cells of living animals can elicit specific humoral responses, and generate biologically relevant anti-viral antibodies.

To test whether the vaccine is capable of eliciting a protective immune response, the animal model described above was used. Tumor cells were transfected with DNA encoding p160, confirmed to express the protein and implanted into the animal. Controls included untransfected tumor lines.

Genetically immunized animals were vaccinated with plasmid pm160. Controls included unvaccinated animals, animals vaccinated with vector DNA only and animals administered the gp160 protein.

Results demonstrate that the immune response of genetically vaccinated mice was sufficient to completely eliminate the transfected tumors while having no effect on untranslated tumors. gp160 protein vaccination led to some reduction in tumor size in transfected tumors as compared to untransfected tumors but had no effect on mortality. Unvaccinated animals showed similar mortality for both transfected and untransfected tumors.

Example 4

The following is a list of constructs which may be used in the methods of the present invention. The vector pBabe.puro, which is used as a starting material to produce many of the below listed constructs, was originally constructed and reported by Morgenstern, J. P. and H. Land, 1990 *Nucl. Acids Res.* 18(12):3587–3596, which is incorporated herein by reference. The pBabe.puro plasmid is particularly useful for expression of exogenous genes in mammalian cells. DNA sequences to be expressed are inserted at cloning sites under the control of the Moloney murine leukemia virus (Mo MuLV) long terminal repeat (LTR) promoter. The plasmid contains the selectable marker for puromycin resistance.

Example 5

Plasmid pBa.Vα3 is a 7.8 kb plasmid that contains a 2.7 kb EcoRI genomic fragment encoding the T cell receptor Va3 region containing the L, V and J segments cloned into the EcoRI site of pBabe.puro. The T cell receptor-derived target protein is useful in the immunization against and treatment of T cell mediated autoimmune disease and clonotypic T cell lymphoma and leukemia.

Example 6

Plasmid pBa.gagpol-vpr is a 9.88 kb plasmid that contains the gag/pol and vif genes from HIV/MN cloned into pBabe.puro. The vpr gene is deleted. The plasmid which contains these HIV viral genes, which encode HIV target proteins, is useful in the immunization against and treatment of HIV infection and AIDS. The HIV DNA sequence is published in Reiz, M. S., 1992 *AIDS Res. Human Retro.* 8:1549, which is incorporated herein by reference. The sequence is accessible from Genbank No.: M17449, which is incorporated herein by reference.

Example 7

Plasmid pM160 is an 11.0 kb plasmid that contains the 2.3 kb PCR fragment encoding the HIV-I/3B envelope protein and rev/tat genes cloned into pMAMneoBlue. The nef region is deleted. The plasmid which contains these HIV viral genes, which encode HIV target proteins, is useful in the immunization against and treatment of HIV infection and AIDS. The DNA sequence of HIV-1/3B is published in Fisher, A., 1985 *Nature* 316:262, which is incorporated herein by reference. The sequence is accessible from Genbank No.: K03455, which is incorporated herein by reference.

Example 8

Plasmid pBa.VL is a 5.4 kb plasmid that contains PCR fragment encoding the VL region of an anti-DNA antibody cloned into pBabe.puro at the XbaI and EcoRI sites. The antibody-derived target protein is an example of a target protein useful in the immunization against and treatment of B cell mediated autoimmune disease and clonotypic B cell lymphoma and leukemia. A general method for cloning functional variable regions from antibodies can be found in Chaudhary, V. K., et al., 1990 *Proc. Natl. Acad. Sci. USA* 87:1066, which is incorporated herein by reference.

Example 9

Plasmid pOspA.B is a 6.84 kb plasmid which contains the coding regions encoding the OspA and OspB antigens of the *Borrelia burgdorferi*, the spirochete responsible for Lyme's disease cloned into pBabe.puro at the BamHI and SalI sites. The PCR primers used to generate the OspA and OspB fragments are 5'-GAAGGATCCAGAAAAAAATATTTAT TGGG-3' (SEQ ID NO: 3) and 5'-ACTGTCGACTTATT TTAAAGCGTTTTTAAG-3' (SEQ ID NO: 4). See: Williams, W. V., et al. 1992 *DNA and Cell. Biol.* 11(3):207, which is incorporated herein by reference. The plasmid which contains these pathogen genes, which encode target proteins, is useful in the immunization against Lyme's disease.

Example 10

Plasmid pBa.Rb-G is a 7.10 kb plasmid which contains a PCR generated fragment encoding the rabies G protein cloned into pBabe.puro at the BamHI site. The plasmid which contains this pathogen gene, which encodes the rabies G protein, is useful in the immunization against Rabies. The DNA sequence is disclosed in Genebank No.:M32751, which is incorporated herein by reference. See also: Anilionis, A., et al., 1981 *Nature* 294:275, which is incorporated herein by reference.

Example 11

Plasmid pBa.HPV-L1 is a 6.80 kb plasmid which contains a PCR generated fragment encoding the L1 capsid protein of the human papillomavirus (HPV) including HPV strains 16, 18, 31 and 33 cloned into pBabe.puro at the BamHI and EcoRI sites. The plasmid is useful in the immunization against HPV infection and the cancer caused thereby. The DNA sequence is disclosed in Genebank No.:M15781, which is incorporated herein by reference. See also: Howley, P., 1990 *Fields Virology*, Volume 2, Eds.: Channock, R. M. et al. Chapter 58:1625; and Shah, K. and P. Howley, 1990 *Fields Virology*, Volume 2, Eds.: Channock, R. M. et al. Chapter 59; both of which are incorporated herein by reference.

Example 12

Plasmid pBa.HPV-L2 is a 6.80 kb plasmid which contains a PCR generated fragment encoding the L2 capsid protein of the human papillomavirus (HPV) including HPV strains 16, 18, 31 and 33 cloned into pBabe.puro at the BamHI and EcoRI sites. The plasmid is useful in the immunization against HPV infection and the cancer caused thereby. The DNA sequence is disclosed in Genebank No.:M15781, which is incorporated herein by reference. See also: Howley, P., 1990 *Fields Virology*, Volume 2, Eds.: Channock, R. M. et al. Chapter 58:1625; and Shah, K. and P. Howley, 1990 *Fields Virology*, Volume 2, Eds.: Channock, R. M. et al. Chapter 59; both of which are incorporated herein by reference.

Example 13

Plasmid pBa.MNp7 is a 5.24 kb plasmid which contains a PCR generated fragment encoding the p7 coding region including the HIV MN gag (core protein) sequence cloned into pBabe.puro at the BamHI site. The plasmid which contains these HIV viral genes, which encode HIV target proteins, is useful in the immunization against and treatment of HIV infection and AIDS. Reiz, M. S., 1992 *AIDS Res. Human Retro.* 8:1549, which is incorporated herein by reference. The sequence is accessible from Genbank No.:M17449, which is incorporated herein by reference.

Example 14

Plasmid pGA733–2 is a 6.3 kb plasmid that contains the GA733–2 tumor surface antigen cloned from the colorectal carcinoma cell line SW948 into pCDM8 vector (Seed, B. and A. Aruffo, 1987 *Proc. Natl. Acad. Sci. USA* 84:3365, which is incorporated herein by reference) at BstXI site. The tumor-associated target protein is an example of a target protein useful in the immunization against and treatment of hyperproliferative disease such as cancer. The GA733-2 antigen is a useful target antigen against colon cancer. The GA733 antigen is reported in Szala, S. et al., 1990 *Proc. Natl. Acad. Sci. USA* 87:3542–3546, which is incorporated herein by reference.

Example 15

Plasmid pT4-pMV7 is a 11.15 kb plasmid that contains cDNA which encodes human CD4 receptor cloned into pMV7 vector at the EcoRI site. The CD4 target protein is useful in the immunization against and treatment of T cell lymphoma. Plasmid pT4-pMV7 is available from the AIDS Repository, Catalog No. 158.

Example 16

Plasmid pDJGA733 is a 5.1 kb plasmid that contains the GA733 tumor surface antigen cloned into pBabe.puro at the BamHI site. The tumor-associated target protein is an example of a target protein useful in the immunization against and treatment of hyperproliferative disease such as cancer. The GA733 antigen is a useful target antigen against colon cancer.

Example 17

Plasmid pBa.RAS is a 6.8 kb plasmid that contains the ras coding region that was first subcloned from pZIPneoRAS and cloned into pBabe.puro at the BamHI site. The ras target protein is an example of a cytoplasmic signalling molecule. The method of cloning ras is reported in Weinberg 1984 *Mol. Cell. Biol.* 4:1577, which is incorporated herein by reference. Ras encoding plasmid are useful for the immunization against and treatment of hyperproliferative disease such as cancer; in particular, ras related cancer such as bladder, muscle, lung, brain and bone cancer.

Example 18

Plasmid pBa.MNp55 is a 6.38 kb plasmid which contains a PCR generated fragment encoding the p55 coding region including the HIV MN gag precursor (core protein) sequence cloned into pBabe.puro at the BamHI site. The plasmid which contains these HIV viral genes, which encode HIV target proteins, is useful in the immunization against and treatment of HIV infection and AIDS. Reiz, M. S., 1992 *AIDS Res. Human Retro.* 8:1549, which is incorporated herein by reference. The sequence is accessible from Genbank No.:M17449, which is incorporated herein by reference.

Example 19

Plasmid pBa.MNp24 is a 5.78 kb plasmid which contains a PCR generated fragment from the pMN-SF1 template encoding the p24 coding region including the whole HIV MN gag coding region cloned into pBabe.puro at the BamHI and EcoRI sites. The plasmid which contains these HIV viral genes, which encode HIV target proteins, is useful in the immunization against and treatment of HIV infection and AIDS. Reiz, M. S., 1992 *AIDS Res. Human Retro.* 8:1549, which is incorporated herein by reference. The sequence is accessible from Genbank No.: M17449, which is incorporated herein by reference.

Example 20

Plasmid pBa.MNp17 is a 5.5 kb plasmid which contains a PCR generated fragment encoding the p17 coding region including the HIV MN gag (core protein) sequence cloned into pBabe.puro at the BamHI and EcoRI sites. The plasmid which contains these HIV viral genes, which encode HIV target proteins, is useful in the immunization against and treatment of HIV infection and AIDS. Reiz, M. S., 1992 *AIDS Res. Human Retro.* 8:1549, which is incorporated herein by reference. The sequence is accessible from Genbank No.: M17449, which is incorporated herein by reference.

Example 21

Plasmid pBa.SIVenv is a 7.8 kb plasmid which contains a 2.71 PCR generated fragment amplified from a construct containing SIV 239 in pBR322 cloned into pBabe.puro at the BamHI and EcoRI sites. The primers used are 5'-GCCAGTTTTGGATCCTTAAAAAAGGCTTGG-3' (SEQ ID NO: 5) and 5'-TTGTGAGGGACAGAA TTCCAATCAGGG-3' (SEQ ID NO: 6). The plasmid is available from the AIDS Research and Reference Reagent Program; Catalog No. 210.

Example 22

Plasmid pcTSP/ATK.env is a 8.92 kb plasmid which contains a PCR generated fragment encoding the complete HTLV envelope coding region from HTLV-1/TSP and /ATK isolates subcloned into the pcDNA1/neo vector. The primers used are 5'-CAGTGATATCCCGGGAGACTCCTC-3' (SEQ ID NO: 7) and 5'-GAATAGAAGAACTCCTCTAGAATTC-3' (SEQ ID NO: 8). Plasmid pcTSP/ATK.env is reported in 1988 *Proc. Natl. Acad. Sci. USA* 85:3599, which is incorporated herein by reference. The HTLV env target protein is useful in the immunization against and treatment of infection by HTLV and T cell lymphoma.

Example 23

Plasmid pBa.MNgp160 is a 7.9 kb plasmid which contains a 2.8 kb PCR generated fragment amplified from a construct containing MNenv in pSP72 and cloned into pBabe.puro at the BamHI and EcoRI sites. The primers used are 5'-GCCTTAGGCGGATCCTATGGCAGGAAG-3' (SEQ ID NO: 9) and 5'-TAAGATGGGTGGCCATGGT GAATT-3' (SEQ ID NO: 10). Reiz, M. S., 1992 *AIDS Res. Human Retro.* 8:1549, which is incorporated herein by reference. The sequence is accessible from Genbank No.:M17449, which is incorporated herein by reference. The plasmid which contains these HIV viral genes, which encode HIV target proteins, is useful in the immunization against and treatment of HIV infection and AIDS.

Example 24

Plasmid pC.MNp55 is a 11.8 kb plasmid which contains a 1.4 kb PCR generated fragment amplified from the gag region of MN isolate and cloned into the pCEP4 vector. The plasmid which contains these HIV viral genes, which encode HIV target proteins, is useful in the immunization against and treatment of HIV infection and AIDS. Reiz, M. S., 1992 *AIDS Res. Human Retro.* 8:1549, which is incorporated herein by reference. The sequence is accessible from Genbank No.: M17449, which is incorporated herein by reference.

Example 25

Plasmid pC.Neu is a 14.2 kb plasmid that contains a 3.8 kb DNA fragment containing the human neu oncogene coding region that was cut out from the LTR-2/erbB-2 construct and subcloned into the pCEP4 vector. The pC.Neu plasmid is reported in DiFiore 1987 *Science* 237:178, which is incorporated herein by reference. The neu oncogene target protein is an example of a growth factor receptor useful as a target protein for the immunization against and treatment of hyperproliferative disease such as cancer; in particular, colon, breast, lung and brain cancer.

Example 26

Plasmid pC.RAS is a 11.7 kb plasmid that contains a 1.4 kb DNA fragment containing the ras oncogene coding region that was first subcloned from pZIPneoRAS and subcloned into pCEP4 at the BamHI site. The pC.RAS plasmid is reported in Weinberg 1984 *Mol. Cell. Biol.* 4:1577, which is incorporated herein by reference. The ras target protein is an example of a cytoplasmic signalling molecule. Ras encoding plasmid are useful for the immunization against and treatment of hyperproliferative disease such as cancer; in particular, ras related cancer such as bladder, muscle, lung, brain and bone cancer.

Example 27

Plasmid pNLpuro is a 15 kb plasmid which contains HIV gag/pol and SV40-puro insertion. The plasmid which contains these HIV viral genes, which encode HIV target proteins, is useful in the immunization against and treatment of HIV infection and AIDS.

Example 28

A DNA construct was designed to test the effectiveness of a genetic vaccine against human CD4 in mice. These experiments were designed to test the ability of a vaccine to protect against a T lymphoma antigen. In T cell lymphoma, CD4 is a tumor specific antigen. Accordingly, this model demonstrates the ability of the genetic vaccine to protect against T lymphoma. Further, these experiments tested the effectiveness against a member of the immunoglobulin superfamily of molecules. CD4 is highly conserved between human and murine species.

The animal model used was described above. Tumor cells were transfected with DNA encoding CD4, confirmed to express the protein and implanted into the animal. Controls included untransfected tumor lines. Although the animals were immunocompetent, an immune response was not directed against the implanted, CD4-labelled tumors in unvaccinated animals.

Genetically immunized animals were vaccinated with plasmid pT4-pMV7, a 11.15 kb plasmid that contains cDNA which encodes human CD4 receptor cloned into pMV7 vector at the EcoRI site. Plasmid pT4-pMV7 is available from the AIDS Repository, Catalog No. 158. Controls included unvaccinated animals and animals administered the CD4 protein.

In the genetic immunization procedure described herein, the quadriceps muscles of BALB/c mice were injected with 100 μl of 0.5% bupivacaine-HCl and 0.1% methylparaben in isotonic NaCl using a 27-gauge needle to stimulate muscle cell regeneration to facilitate uptake of the genetic construct. Twenty-four hours later, the same injection sites were then injected with either 100 μg of pT4-pMV7 or with 100 μg of pMV7 as a control plasmid. The mice were boosted by injecting the same amount of DNA construct three times at two week intervals in the same manner but without pre-treatment with bupivacaine-HCl.

Animals received 1,000,000 CD4-labelled tumor cells. In non-vaccinated animals, large tumors formed and death resulted after about 7–10 weeks. Vaccinated animals did not develop similar deadly tumors.

Results demonstrate that the immune response of genetically vaccinated mice was sufficient to completely eliminate the transfected tumors while having no effect on untransfected tumors. CD4 protein vaccination led to some reduction in tumor size in transfected tumors as compared to untransfected tumors but had no effect on mortality. Unvaccinated animals showed similar mortality for both transfected and untransfected tumors.

Example 29

A DNA construct was designed to test the effectiveness of a genetic vaccine against human GA733 in mice. These experiments were designed to test the ability of a vaccine to protect against GA733 associated cancer such as colon cancer. The animal model used was described above. Tumor cells were transfected with DNA encoding GA733, confirmed to express the protein and implanted into the animal. Controls included untransfected tumor lines.

Genetically immunized animals were vaccinated with plasmid pGA733–2, a 6.3 kb plasmid that contains the GA733-2 tumor surface antigen cloned from the colorectal carcinoma cell line SW948 into pCDM8 vector at BstXI site following the method described above. Controls included unvaccinated animals and animals administered the GA733 protein.

Results demonstrate that the immune response of genetically vaccinated mice was sufficient to completely eliminate the transfected tumors while having no effect on untransfected tumors. GA733 protein vaccination led to some reduction in tumor size in transfected tumors as compared to untransfected tumors but had no effect on mortality. Unvaccinated animals showed similar mortality for both transfected and untransfected tumors.

Example 30

A DNA construct was designed to test the effectiveness of a genetic vaccine against human p185 neu in mice. These experiments were designed to test the ability of a vaccine to protect against p185 neu associated cancer such as breast, lung and brain cancer. The animal model used was described above. Tumor cells were transfected with DNA encoding neu, confirmed to express the protein and implanted into the animal. Controls included untransfected tumor lines.

Genetically immunized animals were vaccinated with plasmid pLTR-2/erbB-2, a 14.3 kb plasmid that contains the human neu oncogene coding region cloned into the LTR-2 vector at the XhoI site following the method described above. The 5'LTR and 3'LTR are from Moloney-MuLV LTR. Controls included unvaccinated animals and animals administered the p185neu protein.

Results demonstrate that the immune response of genetically vaccinated mice was sufficient to completely eliminate the transfected tumors while having no effect on untranslated tumors. p185 protein vaccination led to some reduction in tumor size in transfected tumors as compared to untransfected tumors but had no effect on mortality. Unvaccinated animals showed similar mortality for both transfected and untransfected tumors.

Example 31

A DNA construct was designed to test the effectiveness of a genetic vaccine against human Ras in mice. These experiments were designed to test the ability of a vaccine to protect against Ras associated cancer such as bladder, muscle, lung, brain and bone cancer. The animal model used was described above. Tumor cells were transfected with DNA encoding Ras, confirmed to express the protein and implanted into the animal. Controls included untransfected tumor lines.

Genetically immunized animals were vaccinated with plasmid pBa.RAS is a 6.8 kb plasmid that contains the ras coding region that was first subcloned from pZIPneoRAS and cloned into pBabe.puro at the BamHI site following the vaccination method described above. The ras target protein is an example of a cytoplasmic signalling molecule. The method of cloning ras is reported in Weinberg 1984 *Mol. Cell. Biol.* 4:1577, which is incorporated herein by reference. Controls included unvaccinated animals and animals administered the Ras protein.

Example 32

A DNA construct was designed to test the effectiveness of a genetic vaccine against human rabies G protein antigen in mice. The animal model used was described above. Tumor cells were transfected with DNA encoding rabies G protein, confirmed to express the protein and implanted into the animal. Controls included untransfected tumor lines.

Genetically immunized animals were vaccinated with plasmid pBa.Rb-G is a 7.10 kb plasmid which contains a PCR generated fragment encoding the rabies G protein cloned into pBabe.puro at the BamHI site, following the vaccination method described above. The rabies G target protein is an example of a pathogen antigen. The DNA sequence is disclosed in Genebank No.:M32751. Controls included unvaccinated animals and animals administered the G protein.

Example 33

A DNA construct was designed to test the effectiveness of a genetic vaccine against Lyme's disease antigen in mice. The animal model used was described above. Tumor cells were transfected with DNA encoding OspA and Osp B, confirmed to express the protein and implanted into the animal. Controls included untransfected tumor lines.

Genetically immunized animals were vaccinated with plasmid pOspA.B is a 6.84 kb plasmid which contains the coding regions encoding the OspA and Osp.B antigens of the *Borrelia burgdorferi*, the spirochete responsible for Lyme's disease cloned into pBabe.puro at the BamHI and SalI sites, following the vaccination method described above. The OspA and OspB target proteins are examples of pathogen antigens. The PCR primers used to generate the OspA and OspB fragments are 5'-GAAGGATCCATGAAAAAATAT TTATTGGG-3' (SEQ ID NO: 3) and 5'-ACTGTCG ACTTATTTAAAGCGTTTTAAG-3' (SEQ ID NO: 4).

See: Williams, W. V., et al. 1992 *DNA and Cell. Biol.* 11(3):207, which is incorporated herein by reference. Controls included unvaccinated animals and animals administered OspA and OspB proteins.

Example 34

A DNA construct was designed to test the effectiveness of a genetic vaccine against a human T cell receptor variable region in mice. These experiments were designed to test the ability of a vaccine to protect against a T cell receptor derived protein associated cancer such as T cell lymphoma and T cell mediated autoimmune disease. The animal model used was described above. Tumor cells were transfected with DNA encoding Ras, confirmed to express the protein and implanted into the animal. Controls included untransfected tumor lines.

Genetically immunized animals were vaccinated with plasmid pBa.Vα3 is a 7.8 kb plasmid that contains a 2.7 kb EcoRI genomic fragment encoding the T cell receptor Vα3 region containing the L, V and J segments cloned into the EcoRI site of pBabe.puro following the vaccination method described above.

Example 35

The plasmid pM160 can be used as a starting material for several plasmids useful to express one or more genes from the env portion of HIV. As described above, the DNA segment encoding the envelope gene of HIV-1 HXB2 was cloned by the polymerase chain reaction (PCR) amplification technique utilizing the lambda cloned DNA obtained from the AIDS Research and Reference Reagent Program. The sequences of the 5' and 3' primers are 5'-AGGCGTCTCGAGACAGAGGAGAGCAAGAAATG-3' (SEQ ID NO: 1) with incorporation of XhoI site and 5'-TTTCCCTCTAGATAAGCCATCCAATCACAC-3' (SEQ ID NO: 2) with incorporation of XbaI site, respectively, which encompass gp160, tat and rev coding region. The nef gene is absent. Gene specific amplification was performed using Taq DNA polymerase according to the manufacturer's instructions (Perkin-Elmer Cetus Corp.). The PCR reaction products were treated with 0.5 ug/ml proteinase K at 37° C. for thirty minutes followed by a phenol/chloroform extraction and ethanol precipitation. Recovered DNA was then digested with XhoI and XbaI for two hours at 37° C. and subjected to agarose gel electrophoresis. The isolated and purified XhoI-XbaI PCR fragment was cloned into Bluescript plasmid (Stratagene Inc., La Jolla, Calif.) and then subcloned into the eukaryotic expression vector pMAMneoBlue (Clontech Laboratories, Inc., Palo Alto, Calif.). The resulting construct was designated as pM160. The plasmid DNA was purified with CsCl gradient ultracentrifugation. The restriction enzyme map for pMAMneoBlue plasmid is available from the manufacturer and may be used by those having ordinary skill in the art to engineer, that is to change, delete and add various elements using standard molecular biology techniques and widely available starting material.

The promoter controlling gp160/rev/tat gene expression is MMTV LTR. The promoter may be deleted and replaced with Actin promoter, myosin promoter, HIV LTR promoter and CMV promoter.

The gene conferring ampicillin resistance may be deleted or otherwise inactivated. The gene conferring neomycin resistance may be placed under the control of a bacterial promoter.

The Rous sarcoma virus enhancer may be deleted from the plasmid. The RSV enhancer may be replaced with the muscle creatine enhancer.

The gp160/rev/tat genes overlap and share the same nucleotide sequences in different reading frames. The rev gene may be deleted by changing its initiation codon to a different codon. Similarly, the tat gene may be eliminated by the same means. In each plasmid except those using the HIV LTR promoter to control gp160/rev/tat, either rev, tat, or both rev and tat may be eliminated. In plasmids using the HIV LTR promoter, tat must be present.

The following Table lists pM160-modified plasmids. Each plasmid has an inactivated ampicillin gene. Each has deleted the RSV enhancer. Some have no enhancer (no); some have creatine muscle enhancer (CME). Some have the HIV rev gene (yes) while it is deleted in others (no). Some have the HIV tat gene (yes) while it is deleted in others (no).

| Construct | Promoter | enhancer | rev | tat |
|---|---|---|---|---|
| RA-1 | Actin | no | yes | yes |
| RA-2 | Actin | no | yes | no |
| RA-3 | Actin | no | no | yes |
| RA-4 | Actin | CME | yes | yes |
| RA-5 | Actin | CME | yes | no |
| RA-6 | Actin | CME | no | yes |
| RA-7 | CMV | no | yes | yes |
| RA-8 | CMV | no | yes | no |
| RA-9 | CMV | no | no | yes |
| RA-10 | CMV | CME | yes | yes |
| RA-11 | CMV | CME | yes | no |
| RA-12 | CMV | CME | no | yes |
| RA-13 | MMTV | no | yes | yes |
| RA-14 | MMTV | no | yes | no |
| RA-15 | MMTV | no | no | yes |
| RA-16 | MMTV | CME | yes | yes |
| RA-17 | MMTV | CME | yes | no |
| RA-18 | MMTV | CME | no | yes |
| RA-19 | Myosin | no | yes | yes |
| RA-20 | Myosin | no | yes | no |
| RA-21 | Myosin | no | no | yes |
| RA-22 | Myosin | CME | yes | yes |
| RA-23 | Myosin | CME | yes | no |
| RA-24 | Myosin | CME | no | yes |
| RA-25 | HIV-1 LTR | no | yes | yes |
| RA-26 | HIV-1 LTR | no | no | yes |
| RA-27 | HIV-1 LTR | CME | yes | yes |
| RA-28 | HIV-1 LTR | CME | no | yes |

Constructions RA-29 to RA-56 are identical to RA-1 to RA-32 respectively except in each case the promoter controlling the neomycin gene is a bacterial promoter.

Example 36

The plasmid pNLpuro may be used as a starting material to produce several different plasmids which express the HIV gag/pol genes. As described above, pNLpuro was constructed for expression of gag pol. The HIV-1 genomic clone pNL43 was obtained through the NIH AIDS Research and Reference Reagent Program (ARRRP), Division of AIDS, NIAID, NIH, from Dr. Malcom Martin. The pNL43 clone is a construct that consists of HIV-1 proviral DNA plus 3 kb of host (i.e. human) sequence from the site of integration (5' and 3' of the HIV sequence) cloned into pUC18. The StuI site within the non-HIV 5' flanking human DNA of pNL43 was destroyed by partial digestion with StuI followed by digestion of the free ends with E. coli polymerase 1. The linear plasmid was filled and then self ligated, leaving a unique StuI site within the HIV genome. This plasmid, pNLDstu, was then digested with the blunting enzymes StuI and BsaBI which eliminated a large section of the coding sequence for gp120. The SV40 promoter and puromycin resistance coding region (puromycin acetyl transferase (PAC)) were isolated from pBABE-puro (Morgenstern and Land, 1990 Nucl. Acids Res. 18(12):3587–3596, which is incorporated herein by reference, kindly provided by Dr. Hartmut Land of the Imperial Cancer Research Fund) using EcoRI and ClaI. This fragment was blunted, then cloned into the StuI/BsaBI-digested pNLDstu. A clone was selected with the SV40-puro fragment in the correct orientation so that the 3' LTR of HIV could provide poly A functions for the PAC message. This plasmid was designated pNLpuro.

The vpr regulatory gene is deleted from the HIV gag pol vector in order to eliminate a necessary regulatory protein from the set of genes to be introduced by vaccination. A region from just upstream of the unique PflMI site to just after the vif termination codon was amplified via PCR using primers that introduced a non-conservative amino acid change (glu-→val) at amino acid 22 of vpr, a stop codon in the vpr reading frame immediately after amino acid 22, and an ECORI site immediately following the new stop codon. This PCR fragment was substituted for the PflMI-EcoR I fragment of pNLpuro or pNL43. This substitution resulted in the deletion of 122 nucleotides of the open reading frame of vpr, thus eliminating the possibility of reversion that a point mutation strategy entails. The resulting plasmids, pNLpuroΔvpr, encode the first 21 natural amino acids of vpr plus a valine plus all other remaining HIV-1 genes and splice junctions in their native form. Such deletion strategy would also be applicable to nef, vif, and vpu and allow for structural gene expression but protect from the generation of a live recombinant virus.

In addition to vpr, other changes may be made by those having ordinary skill in the art to plasmid pNL43puro using standard molecular biology techniques and widely available starting material.

The human flanking sequences 5' and 3' of the HIV sequences can be removed by several methods. For example, using PCR, only HIV, SV40-puro, and pUC18 sequences can be amplified and reconstructed.

The psi region of HIV, which is important in the packaging of the virus, can be deleted from pNL43puro-based plasmids. In order to delete the psi region, the pNLpuro plasmid is cut with SacI and SpeI. This digestion removes the psi region as well as the 5' LTR which is upstream and portion of the gag/pol region which is downstream of psi. In order to reinsert the deleted non-psi sequences, PCR amplification is performed to regenerate those sequences. Primers are designed which regenerate the portions of the HIV sequence 5' and 3' to psi without regenerating psi. The primers reform the SacI site at the portion of the plasmid 5' of the 5' LTR. Primers go downstream from a site upstream of the SacI site to a site just 3' of the 5' end of the psi region, generating an AatI site at the 3' end. Primers starting just 5' of the psi region also generate an AatI site and, starting 3' of the SpeI site, regenerate that site. The PCR generated fragments are digested with SacI, AatI and SpeI and ligated together with the SacI/SpeI digested pHLpuro-psi– fragment. The HIV 5' LTR promoter can be deleted and replaced with Moloney virus promoter, MMTV LTR, Actin promoter, myosin promoter and CMV promoter.

The HIV 3'LTR polyadenylation site can be deleted and replaced with SV40 polyadenylation site.

The gene conferring ampicillin resistance may be deleted or otherwise inactivated.

The following is a list of pNLpuro-based constructions in which HIV psi and vpr regions are deleted and human flanking regions 5' and 3' of the HIV sequences are deleted.

| Construct | Promoter | poly(A) | Amp$^r$ |
|---|---|---|---|
| LA-1 | Moloney | HIV 3'LTR | yes |
| LA-2 | Moloney | SV40 | yes |
| LA-3 | Moloney | HIV 3'LTR | no |
| LA-4 | Moloney | 5V40 | no |
| LA-5 | CMV | HIV 3'LTR | yes |
| LA-6 | CMV | SV40 | yes |
| LA-7 | CMV | HIV 3'LTR | no |
| LA-8 | CMV | SV40 | no |
| LA-9 | MMTV | HIV 3'LTR | yes |
| LA-10 | MMTV | SV40 | yes |
| LA-11 | MTTV | HIV 3'LTR | no |
| LA-12 | MTTV | SV40 | no |
| LA-13 | HIV 5' LTR | HIV 3'LTR | yes |
| LA-14 | HIV 5' LTR | SV40 | yes |
| LA-15 | HIV 5' LTR | HIV 3'LTR | no |
| LA-16 | HIV 5' LTR | SV40 | no |

Constructions LA-17 to LA-32 are identical to LA-1 to LA-16 respectively except in each case at least one of the human flanking sequence remains.

Example 37

In another construction for expressing the env gene, that region of HIV may be inserted into the commercially available plasmid pCEP4 (Invitrogen). The pCEP4 plasmid is particularly useful since it contains the Epstein Barr virus origin of replication and nuclear antigen EBNA-1 coding region which produces high copy episomal replication without integration. pCEP4 also contains the hygromycin marker under the regulatory control of the thymidine kinase promoter and polyadenylation site. The HIV env coding region is placed under the regulatory control of the CMV promoter and SV40 polyadenylation site. The HIV env coding region was obtained as a 2.3 kb PCR fragment form HIV/3B, Genebank sequence K03455. The resulting pCEP4-based plasmid, pRA-100, is maintained extrachromosomally and produces gp160 protein.

Example 38

In another construction for expressing the env gene, that region of HIV may be inserted into the commercially available plasmid pREP4 (Invitrogen). The pREP4 plasmid is particularly useful since it contains the Epstein Barr virus origin of replication and nuclear antigen EBNA-1 coding region which produces high copy episomal replication without integration. pREP4 also contains the hygromycin marker under the regulatory control of the thymidine kinase promoter and polyadenylation site. The HIV env coding region is placed under the regulatory control of the RSV promoter and SV40 polyadenylation site. The HIV env coding region was obtained as a 2.3 kb PCR fragment form HIV/3B, Genebank sequence K03455. The resulting pCEP4-based plasmid, pRA-101, is maintained extrachromosomally and produces gp160 protein.

Example 39

In another construction for expressing the gag/pol genes, that region of HIV may be inserted into the commercially available plasmid pCEP4 (Invitrogen). The pCEP4 plasmid is particularly useful since it contains the Epstein Barr virus origin of replication and nuclear antigen EBNA-1 coding region which produces high copy episomal replication without integration. pCEP4 also contains the hygromycin marker under the regulatory control of the thymidine kinase promoter and polyadenylation site. The HIV gag/pol coding region is placed under the regulatory control of the CMV promoter and SV40 polyadenylation site. The HIV gag/pol coding region was obtained from HIV MN, Genebank sequence MI7449, and includes the vif gene. The vpr gene is not included. The resulting pCEP4-based plasmid, pLA-100, is maintained extrachromosomally and produces GAG55, reverse transcriptase, protease and integrase proteins.

Example 40

In another construction for expressing the gag/pol genes, that region of HIV may be inserted into the commercially available plasmid pREP4 (Invitrogen). The pREP4 plasmid is particularly useful since it contains the Epstein Barr virus origin of replication and nuclear antigen EBNA-1 coding region which produces high copy episomal replication without integration. pREP4 also contains the hygromycin marker under the regulatory control of the thymidine kinase promoter and polyadenylation site. The HIV gag/pol coding region is placed under the regulatory control of the CMV promoter and SV40 polyadenylation site. The HIV gag/pol coding region was obtained from HIV MN, Genebank sequence MI7449, and includes the vif gene. The vpr gene is not included. The resulting pREP4-based plasmid, pLA-101, is maintained extrachromosomally and produces GAG55, reverse transcriptase, protease and integrase proteins.

Example 41

The following construction, referred to herein as pGAGPOL.rev, is useful to express HIV gag/pol genes.

The plasmid includes a Kanamycin resistance gene and a pBR322 origin of DNA replication. The sequences provided for transcription regulation include: a cytomegalovirus promoter; a Rous sarcoma virus enhancer; and an SV40 polyadenylation signal. The HIV-1 sequences included in pGAGPOL.rev include a sequence that encodes gag; a sequence that encodes pol; a sequence that encodes reverse transcriptase which contains a small deletion; a sequence that encodes the inactive amino terminus of Int; and a sequence that encodes rev. Each of the HIV sequences are derived from HIV-1 strain HXB2.

Several safety features are included in pGAGPOL.rev. These include use of the CMV promoter and a non-retroviral poly(A) site. Furthermore, deletion of the ψ sequence limits the ability to package viral RNA. In addition, multiple mutations of the reverse transcriptase yield an enzymatically inactive product. Moreover, a large deletion of integrase yields an inactive product and a Kanamycin resistance marker is used for stabilizing bacterial transformants.

Plasmid pGAGPOL.rev is constructed as follows.

Step 1. A subclone of part of the HIV-1 (HXB2) genome that is cloned into Bluescript (Stratagene) is used. The subclone of HIV-1 contains the complete 5'LTR and the rest of the HIV-1 genome to nucleotide 5795 (Genebank numbering). The HIV-1 sequences are obtained from the HXB2D plasmid (AIDS Repository).

Step 2. PCR part of gag from the open reading frame HXB2D plasmid (AIDS Repository). Cut PCR fragment with NotI and SpeI and ligate with HIV-1 subclone described above restricted with NotI and SpeI.

Step 3. PCR gag/pol junction and part of pol-encoding sequences from the HXB2D plasmid (AIDS Repository) with primers SEQ ID NO.:17 and SEQ ID NO.:18. Cut PCR product with ClaI and ligate together.

Cut ligated fragments with BclI and SalI and ligate with plasmid from Step 2 digested with BclI and SalI.

Step 4. Cut plasmid from Step 3 with BspMI and EcoRI and religate with adapters formed by annealing linkers SEQ ID NO.:19 and SEQ ID NO.:20.

Step 5. Cut plasmid from Step 4 with NotI and SalI and ligate with plasmid from either 4a or 4b in description written for PENV (below). Cut also with NotI and SalI.

Step 6. Restrict plasmid from Step 5 with SalI and MluI and ligate with PCR product obtained by PCR of rev with primers SEQ ID NO.:21 and SEQ ID NO.:22.

Step 7. Cut plasmid from Step 6 with NotI and ligate with product obtained by PCR of the rev responsive element in the HXB2D plasmid (AIDS Repository) with primers SEQ ID NO.:23 and SEQ ID NO.:24.

Steps 6 and 7 are optional.

Example 42

The following construction, referred to herein as pENV, is useful to express HIV env genes.

The plasmid includes a Kanamycin resistance gene and a pBR322 origin of DNA replication. The sequences provided for transcription regulation include: a cytomegalovirus promoter; a Rous sarcoma virus enhancer; and an SV40 polyadenylation signal. The HIV-1 sequences included in pENV include a sequence that encodes vpu; a sequence that encodes rev; a sequence that encodes gp160; a sequence that encodes 50% of nef; a sequence that encodes vif; and, a sequence that encodes vpr with a 13 amino acid carboxy-end deletion. The vpu, rev, gp160 and nef sequences are derived from HIV-1 strain MN. The vif and vpr sequences are derived from HIV-1 strain HXB2.

Several safety features are included in PGAGPOL.rev. These include use of the CMV promoter and a non-retroviral poly(A) site. Furthermore, tat has been deleted and a 50% deletion of nef yields an "inactive" nef product. In addition, vif and vpr are placed out of normal sequence and a partial deletion of vpr further ensures an inactive vpr product.

Plasmid pENV is constructed as follows.

Step 1. Start with pUC18 digested with HindIII and EcoRI. The resulting fragment that contains the ColE1 origin of replication and the laci gene should be ligated with the EcoRI/HindIII fragment from pMAMneoBlue that contains the our sarcoma virus enhancer. The resulting plasmid or pMAMneo-Blue from Clontech (Palo Alto, Calif.) can then be digested with HindIII and BglII. Using standard techniques, ligate with fragment containing kn gene obtained by PCR of geneblock plasmid (Pharmacia).

Step 2. If pMAMneo-Blue used as starting plasmid, digest with MluI and EcoRI, fill in the ends with Klenow fragment of Polymerase I and religate.

Step 3. Them, with either pMAMneo-Blue or pUC18-derived plasmid, digest with HindIII and ligate with the SV40 polyA site and early splicing region obtained by PCR of pCEP4 (Invitrogen, San Diego, Calif.) with primers SEQ ID NO.:25 and SEQ ID NO.:26.

Step 4a. Digest with BamHI and ligate with the CMV promoter obtained by PCR of pCEP4 (Invitrogen, San Diego, Calif.) with primers SEQ ID NO.:27 and SEQ ID NO.:28.

Step 4b. Digest with BamHI and ligate with the MOMLV LTR obtained by PCR with primers SEQ ID NO.:29 and SEQ ID NO.:30.

Step 5. Digest with NotI and MluI and ligate with GP160 coding region obtained by PCR of pMN-ST1 with primers SEQ ID NO.:31 and SEQ ID NO.:32.

Step 6. Digest with MluI and ligate with sequences that encode vif in its entirety and vpr with a 13aa carboxy-end deletion by CPR of HXB2D plasmid (AIDS Repository) with primers SEQ ID NO.:33 and SEQ ID NO.:34.

Example 43

An immunization system is provided which comprises:

a pharmaceutical composition comprising about 100 μg of pGAGPOL. rev in an isotonic, pharmaceutically acceptable solution; and, a pharmaceutical preparation comprising 100 μg of PENV in an isotonic, pharmaceutically acceptable solution. In addition, the immunization system preferably comprises a pharmaceutical composition comprising about 1 ml of 0.5% bupivacaine-HCl and 0.1% methylparaben in an isotonic pharmaceutical carrier.

In such a preferred immunization system, a first set of administrations is performed in which bupivacaine and one of the two pharmaceutical compositions are administered intramuscularly to an individual, preferably into a muscle of an arm or buttock. Bupivacaine and the other of the two pharmaceutical compositions are administered intramuscularly to the individual at a different site, preferably remote from the site of the administration of the one pharmaceutical composition, preferably into a muscle of the other arm or buttock. Subsequence sets of administrations may be performed later in time, preferably 48 hours to two weeks or more later.

The immunization system may be used to vaccinate an individual in order to protect that individual from HIV infection or to treat an HIV infected individual with an immunotherapeutic.

Example 44

In some embodiments, the present invention relates to a method of immunizing an individual against HIV by administering a single inoculant. This inoculant includes a genetic construct that comprises at least one, preferably two, more preferably more than two or a plurality of the genes of the HIV virus or all of the structural genes. However, the inoculant does not contain a complete complement of all HIV genes. If a single cell is provided with a complete complement of viral genes, it is possible that a complete infectious virus can be assembled within the cell. Accordingly, a genetic construct according to the present invention is not provided with such a full complement of genes. As a safety precaution, one or more essential genes can be deleted or intentionally altered to further ensure that an infectious viral particle cannot be formed.

In some embodiments of the present invention, at least portions of one, two or all HIV structural genes are provided. The structural genes of HIV consist of gag, pol and env. Portions of at least one of these three genes are provided on a genetic construct. Accordingly, in some embodiments, at least a portion of each of gag and pol are provided on a genetic construct; in some embodiments, at least a portion of env is provided on a genetic construct; in some embodiments, at least a portion of gag is provided on a genetic construct; in some embodiments at least a portion of each of pol and env are provided on a genetic construct; in some embodiments, at least a portion of each of gag and env are provided on a genetic construct; in some embodiments at least a portion of pol is provided on a genetic construct. Optionally, the entire gene is provided. Optionally, in any of these constructs, HIV regulatory genes may also be present. The HIV regulatory genes are: vpr, vif, vpu, nef, tat and rev.

Example 45

As used herein, the term "expression unit" is meant to refer to a nucleic acid sequence which comprises a promoter operably linked to a coding sequence operably linked to a polyadenylation signal. The coding sequence may encode one or more proteins or fragments thereof. In preferred embodiments, a expression unit is within a plasmid.

As used herein, the term "HIV expression unit" is meant to refer to a nucleic acid sequence which comprises a promoter operably linked to a coding sequence operably linked to a polyadenylation signal in which the coding sequence encodes a peptide that comprises an epitope that is identical or substantially similar to an epitope found on an HIV protein. "Substantially similar epitope" is meant to refer to an epitope that has a structure which is not identical to an epitope of an HIV protein but nonetheless invokes an cellular or humoral immune response which cross reacts to an HIV protein. In preferred embodiments, the HIV expression unit comprises a coding sequence which encodes one or more HIV proteins or fragments thereof. In preferred embodiments, an HIV expression unit is within a plasmid.

In some embodiments of the present invention, a single genetic construct is provided that has a single HIV expression unit which contains DNA sequences that encode one or more HIV proteins or fragments thereof. As used herein, the term "single HIV expression unit construct" is meant to refer to a single genetic construct that contains a single HIV expression unit. In preferred embodiments, a single HIV expression unit construct is in the form of a plasmid.

In some embodiments of the present invention, a single genetic construct is provided that has more than one HIV expression units in which each contain DNA sequences that encode one or more HIV proteins or fragments thereof. As used herein, the term "multiple HIV expression unit genetic construct" is meant to refer to a single plasmid that contains more than one HIV expression units. In preferred embodiments, a multiple HIV expression unit construct is in the form of a plasmid.

In some embodiments of the present invention, a single genetic construct is provided that has two HIV expression units in which each contain DNA sequences that encode one or more HIV proteins or fragments thereof. As used herein, the term "two HIV expression unit genetic construct" is meant to refer to a single plasmid that contains two HIV expression units, i.e a multiple HIV expression unit genetic construct that contains two HIV expression unit genetic expression units. In a two HIV expression unit genetic construct, it is preferred that one HIV expression unit operates in the opposite direction of the other HIV expression unit. In preferred embodiments, a two HIV expression unit construct is in the form of a plasmid.

In some embodiments of the present invention, an HIV genetic vaccine is provided which contains a single genetic construct. The single genetic construct may be a single HIV expression unit genetic construct, a two HIV expression unit genetic construct or a multiple HIV expression unit genetic construct which contains more than two HIV expression units.

In some embodiments of the present invention, an HIV genetic vaccine is provided which contains more than one genetic construct in a single inoculant.

In some embodiments of the present invention, an HIV genetic vaccine is provided which contains more than one genetic construct in more than one inoculant. As used herein, the term "multiple inoculant" is meant to refer to a genetic vaccine which comprises more than one genetic construct, each of which is administered separately. In some embodiments of the present invention, an HIV genetic vaccine is provided which contains two genetic constructs. Each genetic construct may be, independently, a single HIV expression unit genetic construct, a two HIV expression unit genetic construct or a multiple HIV expression unit genetic construct which contains more than two HIV expression units. In some embodiments, both genetic constructs are single HIV expression unit genetic constructs. In some embodiments, both genetic constructs are two HIV expression unit genetic constructs. In some embodiments, both genetic constructs are multiple HIV expression unit genetic constructs. In some embodiments, one genetic construct is a single HIV expression unit genetic construct and the other is a two HIV expression unit genetic construct. One having ordinary skill in the art can readily recognize and appreciate the many variations depending upon the number of genetic constructs used in a genetic vaccine and the number of HIV expression units that may be present on each genetic construct.

It is preferred that the genetic constructs of the present invention do not contain certain HIV sequences, particularly, those which play a role in the HIV genome integrating into the chromosomal material of the cell into which it is introduced. It is preferred that the genetic constructs of the present invention do not contain LTRs from HIV. Similarly, it is preferred that the genetic constructs of the present invention do not contain a psi site from HIV. Further, it is preferred that the reverse transcriptase gene is deleted and the integrase gene is deleted. Deletions include deletionof only some of the codons or replacing some of the codons in order to essentially delete the gene. For example, the initiation codon may be deleted or changed or shifted out of frame to result in a nucleotide sequence that encodes an incomplete and non-functioning.

It is also preferred that the genetic constructs of the present invention do not contain a transcribable tat gene from HIV. The tat gene, which overlaps the rev gene may be completely deleted by substituting the codons that encode rev with other codons that encode the same amino acid for rev but which does not encode the required tat amino acid in the reading frame in which tat is encoded. Alternatively, only some of the codons are switched to either change, i.e. essentially delete, the initiation codon for tat and/or change, i.e. essentially delete, sufficient codons to result in a nucleotide sequence that encodes an incomplete and non-functioning tat.

It is preferred that a genetic construct comprises coding sequences that encode peptides which have at least an epitope identical to or substantially similar to an epitope from HIV gag, pol, env or rev proteins. It is more preferred that a genetic construct comprises coding sequences that encode at least one of HIV gag, pol, env or rev proteins or fragments thereof. It is preferred that a genetic construct comprises coding sequences that encode peptides which have more than one epitopes identical to or substantially similar to an epitope from HIV gag, pol, env or rev proteins. It is more preferred that a genetic construct comprises coding sequences that encode more than one of HIV gag, pol, env or rev proteins or fragments thereof.

In some embodiments, a genetic construct comprises coding sequences that encode peptides which have at least an epitope identical to or substantially similar to an epitope from HIV vif, vpr, vpu or nef proteins. In some embodiments, a genetic construct comprises coding sequences that encode at least one of HIV vif, vpr, vpu or nef proteins or fragments thereof.

A single HIV expression unit genetic construct may comprise coding regions for one or more peptides which share at least one epitope with an HIV protein or fragment thereof in a single expression unit under the regulatory control of single promoter and polyadenylation signal. It is preferred that genetic constructs encode more than one HIV protein or fragment thereof. The promoter may be any promoter functional in a human cell. It is preferred that the promoter is an SV40 promoter or a CMV promoter, preferably a CMV immediate early promoter. The polyadenylation signal may be any polyadenylation signal functional in a human cell. It is preferred that the polyadenylation signal is an SV40 polyadenylation signal, preferably the SV40 minor polyadenylation signal. If more than one coding region is provided in a single expression unit, they may be immediately adjacent to each other or separated by non-coding regions. In order to be properly expressed, a coding region must have an initiation codon and a termination codon.

A two HIV expression unit genetic construct may comprise coding regions for one or more peptides which share at least one epitope with an HIV protein or fragment thereof on each of the two expression units. Each expression unit is under the regulatory control of single promoter and polyadenylation signal. In some embodiments, it is preferred that genetic constructs encode more than one HIV protein or fragment thereof. In some embodiments, it is preferred that nucleotide sequences encoding gag and pol are present on one expression unit and nucleotide sequences encoding env and rev are present on the other. The promoter may be any promoter functional in a human cell. It is preferred that the promoter is an SV40 promoter or a CMV promoter, preferably a immediate early CMV promoter. The polyadenylation signal may be any polyadenylation signal functional in a human cell. It is preferred that the polyadenylation signal is an SV40 polyadenylation signal, preferably the SV40 minor polyadenylation signal. If more than one coding region is provided in a expression unit, they may be immediately adjacent to each other or separated by non-coding regions. In order to be properly expressed, a coding region must have an initiation codon and a termination codon.

According to some embodiments of the present invention, the MHC Class II crossreactive epitope in env is deleted and replaced with the analogous region from HIV II.

When a genetic construct contains gag and/or pol, it is generally important that rev is also present. In addition to rev, a rev response element may be provided with gag and pol for increased expression of those genes.

When genetic constructs are produced that it is preferred that the env gene used in plasmid 1 is derived from MN or MN-like isolates including clinical isolates resembling MN, preferably non-syncytial inducing clinical isolates, preferably those that are macrophage tropic from early stage clinical isolates.

Multiple proteins may be produced from a single expression unit by alternative splicing. Splicing signals are provided tp allow alternative splicing which produces different messages encoding different proteins.

Example 46

FIG. 8 shows four backbones, A, B, C and D. FIG. 9 shows 4 inserts, 1, 2, 3 and 4. Insert 1 supports expression of gag and pol; the rev response element was cloned in a manner to conserve the HIV splice acceptor. Insert 2 is similar to insert 1 as it too supports expression of gag and pol except the rev reponse element was cloned without conserving the HIV splice acceptor Insert 3 supports expression of gag and pol, includes a deletion of the integrase gene and does not include the presence of the cis acting rev response element. Insert 4 supports expression of rev, vpu and env. The env may have the MHC class II cross reactive epitope altered to eliminate crossreactivity and the V3 loop may be alterered to eliminate the possibility of syncytia formation.

In some embodiments, backbone A is used with insert 1. Such constructs optionally contain the SV40 origin of replication. Plasmid pA1ori+is backbone A with insert 1 and the SV40 origin of replication. Plasmid pA1ori− is backbone A with insert 1 without the SV40 origin of replication. Additionally, either pA1ori+ or pA1ori− may include integrase yielding pA1ori+int+ and pA1ori−int+, respectively. Plasmids pAlori+, pA1ori−, pA1ori+int+ and pA1ori−int+ may be further modified by functionally deleing the reverse transcriptase (RT) gene yielding pA1ori+RT−, pA1ori−RT−, pA1ori+int+RT− and pA1ori−int+RT−, respectively.

In some embodiments, backbone A is used with insert 2. Such constructs optionally the SV40 origin of replication. Plasmid pA2ori+is backbone A with insert 2 and the SV40 origin of replication. Plasmid pA2ori− is backbone A with insert 1 without the SV40 origin of replication. Additionally, either pA2ori+ or pA2ori− may include integrase yeilding pA2ori+int+ and pA2ori−int+, respectively. Plasmids pA2ori+, pA2ori−, pA2ori+int+ and pA2ori−int+ may be further modified by functionally deleing the reverse transcriptase (RT) gene yielding pA2ori+RT−, pA2ori−RT−, pA2ori+int+RT− and pA2ori−int+RT−, respectively.

In some embodiments, backbone B is used with insert 1. Such constructs optionally the SV40 origin of replication. Plasmid pB1ori+ is backbone B with insert 1 and the SV40 origin of replication. Plasmid pB1ori− is backbone B with insert 1 without the SV40 origin of replication. Additionally, either pB1ori+ or pB1ori− may include integrase yeilding pB1ori+int+ and pB1ori−int+, respectively. Plasmids pB1ori+, pB1ori−, pB1ori+int+ and pB1ori−int+ may be further modified by functionally deleting the reverse transcriptase (RT) gene yielding pB1ori+RT−, pB1lori−RT−, pB1ori+int+RT− and pB1ori−int+RT−, respectively.

In some embodiments, backbone B is used with insert 2. Such constructs optionally the SV40 origin of replication. Plasmid pB2ori+ is backbone B with insert 2 and the SV40 origin of replication. Plasmid pB2ori− is backbone B with insert 1 without the SV40 origin of replication. Additionally, either pB2ori+ or pB2ori− may include integrase yeilding pB2ori+int+ and pB2ori−int+, respectively. Plasmids pB2ori+, pB2ori−, pB2ori+int+ and pB2ori−int+ may be further modified by functionally deleing the reverse transcriptase (RT) gene yielding pB2ori+RT−, pB2ori−RT−, pB2ori+int+RT− and pB2ori−int+RT−, respectively.

In some embodiments, backbone A minus rev is used with insert 3. Such constructs optionally the SV40 origin of replication. Plasmid pA/r−3ori+ is backbone A with insert 2 and the SV40 origin of replication. Plasmid pA/r−3ori− is backbone A minus rev with insert 3 without the SV40 origin of replication. Additionally, either pA/r−3ori+ or pA/r−3ori− may include integrase yeilding pA/r−3ori+int+ and pA/r−3ori−int+, respectively. Plasmids pA/r−3ori+, pA/r−3ori−, pA/r− 3ori+int+ and pA/r−3ori−int+ may be further modified by functionally deleing the reverse transcriptase (RT) gene yielding pA/r−3ori+RT−, pA/r−3ori−RT−, pA/r−3ori+int+RT− and pA/r−3ori−int+RT−, respectively.

In some embodiments, backbone C is used with insert 1. Such constructs optionally the SV40 origin of replication. Plasmid pclori+ is backbone C with insert 1 and the SV40 origin of replication. Plasmid pC1ori− is backbone C with insert 1 without the SV40 origin of replication. Additionally, either pc1ori+ or pc1ori– may include integrase yeilding pc1ori+int+ and pC1ori–int+, respectively. Plasmids pC1ori+, pc1ori–, pc1ori+int+ and pc1ori–int+ may be further modified by functionally deleing the reverse transcriptase (RT) gene yielding pC1ori+RT–, pC1ori–RT–, pC1ori+int+RT– and pC1ori–int+RT–, respectively.

In some embodiments, backbone C is used with insert 2. Such constructs optionally the SV40 origin of replication. Plasmid pC2ori+ is backbone C with insert 2 and the SV40 origin of replication. Plasmid pC2ori– is backbone C with insert 2 without the SV40 origin of replication. Additionally, either pC2ori+ or pC2ori– may include integrase yeilding pC2ori+int+ and pC2ori–int+, respectively. Plasmids pC2ori+, pC2ori–, pC2ori+int+ and pC2ori–int+ may be further modified by functionally deleing the reverse transcriptase (RT) gene yielding pC2ori+RT–, pC2ori–RT–, pC2ori+int+RT– and pC2ori–int+RT–, respectively.

In some embodiments, backbone C is used with insert 3. Such constructs optionally the SV40 origin of replication. Plasmid pC3ori+is backbone C with insert 3 and the SV40 origin of replication. Plasmid pC3ori– is backbone C with insert 3 without the SV40 origin of replication. Additionally, either pC3ori+ or pC3ori– may include integrase yeilding pC3ori+int+ and pC3ori–int+, respectively. Plasmids pC3ori+, pC3ori–, pC3ori+int+ and pC3ori–int+ may be further modified by functionally deleing the reverse transcriptase (RT) gene yielding pC3ori+RT–, pC3ori–RT–, pC3ori+int+RT– and pC3ori–int+RT–, respectively.

In some embodiments, backbone D is used with insert 4. Such constructs optionally the SV40 origin of replication. Plasmid pD4ori+ is backbone D with insert 4 and the SV40 origin of replication. Plasmid pD4ori– is backbone D with insert 4 without the SV40 origin of replication.

Example 47

In some embodiments, a single expression unit/single inoculant genetic vaccine is provided which comprises a genetic construct that includes a coding sequence which encodes a peptide that has at least one epitope which is an identical to or substantially similar to epitopes of HIV proteins. The coding sequence is under the regulatory control of the CMV immediate early promoter and the SV40 minor polyadenylation signal.

In some embodiments, a single expression unit/single inoculant genetic vaccine is provided which comprises a genetic construct that includes a coding sequence which encodes at least one HIV protein or a fragment thereof. The coding sequence is under the regulatory control of the CMV immediate early promoter and the SV40 minor polyadenylation signal. The HIV protein is selected from the group consisting of gag, pol, env and rev. In some embodiments it is preferred that the genetic vaccine is provided which comprises a genetic construct that includes a coding sequence which encodes at least two HIV proteins or a fragments thereof selected from the group consisting of gag, pol, env and rev or fragments thereof. In some embodiments, it is preferred that the genetic vaccine is provided which comprises a genetic construct that includes a coding sequence which encodes at least three HIV proteins or a fragments thereof selected from the group consisting of gag, pol, env and rev or fragments thereof. In some embodiments, it is preferred that the genetic vaccine is provided which comprises a genetic construct that includes a coding sequence which encodes gag, pol, env and rev or fragments thereof.

In some embodiments, a dual expression unit/single inoculant genetic vaccine is provided which comprises a genetic construct that includes two expression units each of which comprises a coding sequence which encodes a peptide that has at least one epitope which is an identical to or substantially similar to epitopes of HIV proteins. The coding sequence is under the regulatory control of the CMV immediate early promoter and the SV40 minor polyadenylation signal. The two expression units are encoded in opposite directions of each other.

In some embodiments, a dual expression unit/single inoculant genetic vaccine is provided which comprises a genetic construct that includes two expression units each of which comprises a coding sequence which encodes at least one HIV protein or a fragment thereof. Each expression unit comprises a coding sequence that is under the regulatory control of the CMV immediate early promoter and the SV40 minor polyadenylation signal. The HIV protein is selected from the group consisting of gag, pol, env and rev. In some embodiments it is preferred that the genetic vaccine is provided which comprises a genetic construct that includes two expression units, at least one of which comprises a coding which encodes at least two HIV proteins or a fragments thereof selected from the group consisting of gag, pol, env and rev or fragments thereof and the other comprises at least one HIV proteins or a fragments thereof selected from the group consisting of gag, pol, env and rev or fragments thereof. In some embodiments, it is preferred that the genetic vaccine is provided which comprises a genetic construct that includes two expression units, at least one of which comprises a coding sequence which encodes at least three HIV proteins or a fragments thereof selected from the group consisting of gag, pol, env and rev or fragments thereof and the other comprises at least one HIV proteins or a fragments thereof selected from the group consisting of gag, pol, env and rev or fragments thereof. In some embodiments, it is preferred that the genetic vaccine is provided which comprises a genetic construct that comprises two expression units and includes a coding sequence which encodes gag, pol, env and rev or fragments thereof.

TABLE 1

Picornavirus Family
    Genera:    Rhinoviruses: (Medical) responsible for ~50% cases of the common cold.
        Ehteroviruses: (Medical) includes polioviruses, coxsackieviruses, echoviruses, and human enteroviruses such as hepatitis A virus.
        Apthoviruses: (Veterinary) these are the foot and mouth disease viruses.
    Target antigens: VP1, VP2, VP3, VP4, VPG
Calcivirus Family
    Genera:    Norwalk Group of Viruses: (Medical) these viruses are an important causative agent of epidemic gastroenteritis.
Togavirus Famiiy
    Genera:    Alphaviruses: (Medical and Veterinary) examples include Senilis viruses, RossRiver virus and Eastern & Western Equine*** encephalitis.
        Reovirus: (Medical) Rubella virus.
Flariviridue Family
        Examples include: (Medical) dengue, yellow fever, Japanese encephalitis, St. Louis encephalitis and tick borne encephalitis viruses.
Hepatitis C Virus: (Medical) these viruses are not placed in a family yet but are believed to be either a togavirus or a flavivirus. Most similarity is with togavirus family.

TABLE 1-continued

Coronavirus Family: (Medical and Veterinary)
Infectious bronchitis virus (poultry)
Porcine transmissible gastroenteric virus (pig)
Porcine hemagglutinatiny encephalomyelitis virus (pig)
Feline infectious peritonitis virus (cats)
Feline enteric coronavirus (cat)
Canine coronavirus (dog)
The human respiratory coronaviruses cause ~40 cases of common cold. EX. 224E, 0C43
Note - coronaviruses may cause non-A, B or C hepatitis
Target antigens:
E1 - also called M or matrix protein
    E2 - also called S or Spike protein
    E3 - also called HE or hemagglutin-elterose glycoprotein (not present in all coronaviruses)
    N - nucleocapsid Rhabdovirus Family
  Genera: Vesiliovirus
    Lyssavirus: (Medical and veterinary) rabies
  Target antigen: G protein
    N protein Filoviridue Family: (Medical)
  Hemorrhagic fever viruses such as Marburg and Ebola virus Paramyxovirus Family:
  Genera: Paramyxovirus: (Medical and Veterinary) Mumps virus, New Castle disease virus (important pathogen in chickens)
    Morbillivirus: (Medical and Veterinary) Measles, canine distemper
    Pneuminvirus: (Medical and Veterinary) Respiratory syncytial virus Orthomyxovirus Family (Medical)
  The Influenza virus Bungavirus Family
  Genera: Bungavirus: (Medical) California encephalitis, LA Crosse
    Phlebovirus: (Medical) Rift Valley Fever
    Hantavirus: Puremala is a hemahagin fever virus
    Nairvirus (Veterinary) Nairobi sheep disease
    Also many unassigned bungaviruses Arenavirus Family (Medical)
  LCM, Lassa fever virus Reovirus Family
  Genera: Reovirus: a possible human pathogen
    Rotavirus: acute gastroenteritis in children
    Orbiviruses: (Medical and Veterinary) Colorado Tick fever, Lebombo (humans) equine encephalosis, blue tongue Retrovirus Family
  Sub-Family:
    Oncorivirinal: (Veterinary) (Medical) feline leukemia virus, HTLVI and HTLVII
    Lentivirinal: (Medical and Veterinary) HIV, feline immunodeficiency virus, equine infections, anemia virus
    Spumavirinal Papovavirus Family
  Sub-Family:
    Polyomaviruses: (Medical) BKU and JCU viruses
  Sub-Family:
    Papillomavirus: (Medical) many viral types associated with cancers or malignant progression of papilloma Adenovirus (Medical)
  EX AD7, ARD., O.B. - cause respiratory disease - some adenoviruses such as 275 cause enteritis Parvovirus Family (Veterinary)
  Feline parvovirus: causes feline enteritis

TABLE 1-continued

Feline panleucopeniavirus
  Canine parvovirus
  Porcine parvovirus

Herpesvirus Family
  Sub-Family: alphaherpesviridue
  Genera: Simplexvirus (Medical)
    HSVI, HSVII
    Varicellovirus: (Medical - Veterinary) pseudorabies - varicella zoster
  Sub-Family - betaherpesviridue
  Genera: Cytomegalovirus (Medical)
    HCMV
    Muromegalovirus
  Sub-Family: Gammaherpesviridue
  Genera: Lymphocryptovirus (Medical)
    EBV - (Burkitts lympho)
    Rhadinovirus Poxvirus Family
  Sub-Family: Chordopoxviridue (Medical - Veterinary)
  Genera: Variola (Smallpox)
    Vaccinia (Cowpox)
    Parapoxivirus - Veterinary
    Auipoxvirus - Veterinary
    Capripoxvirus
    Leporipoxvirus
    Suipoxvirus
  Sub-Family: Entemopoxviridue Hepadnavirus Family
  Hepatitis B virus Unclassified
  Hepatitis delta virus

TABLE 2

Bacterial pathogens
  Pathogenic gram-positive cocci include: pneumococcal; staphylococcal; and streptococcal.
  Pathogenic gram-negative cocci include: meningococcal; and gonococcal.
  Pathogenic enteric gram-negative bacilli include: enterobacteriaceae; pseudomonas, acinetobacteria and eikenella; melioidosis; salmonella; shigellosis; hemophilus; chancroid; brucellosis; tularemia; yersinia (pasteurella); streptobacillus moniliformis and spirillum; listeria monocytogenes; erysipelothrix rhusiopathiae; diphtheria; cholera; anthrax; donovanosis (granuloma inguinale); and bartonellosis.
  Pathogenic anaerobic bacteria include: tetanus; botulism; other clostridia; tuberculosis; leprosy; and other mycobacteria. Pathogenic spirochetal diseases include: syphilis; treponematoses: yaws, pinta and endemic syphllis; and leptospirosis.
  Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis.
  Rickettsial infections include rickettsial and rickettsioses.
  Examples of mycoplasma and chlamydial infections include: mycoplasma pneumoniae; lymphogranuloma venereum; psittacosis; and perinatal chlamydial infections.

Pathogenic eukaryotes
  Pathogenic protozoans and helminths and infections thereby include: amebiasis; malaria; leishmaniasis; trypanosomiasis; toxoplasmosis; pneumocystis carinii; babesiosis; giardiasis; trichinosis; filariasis; schistosomiasis; nematodes; trematodes or flukes; and cestode (tapeworm) infections.

We claim:

1. An pharmaceutical immunizing kit comprising:
   a) a first inoculant comprising:
     i) a pharmaceutically acceptable carrier or diluent; and,
     ii) a first nucleic acid molecule comprising a nucleotide sequence that encodes at least one HIV protein operatively linked to regulatory sequences; wherein said nucleotide sequence is capable of being expressed in human cells;
   b) a second inoculant comprising:
     i) a pharmaceutically acceptable carrier or diluent; and,
     ii) a second nucleic acid molecule comprising a nucleotide sequence that encodes at least one HIV protein operatively linked to regulatory sequences; wherein said nucleotide sequence is capable of being expressed in human cells;
wherein said first nucleic acid molecule is not identical to said second nucleic acid molecule and, taken together, said first nucleic acid molecule and said second nucleic acid molecule encode HIV proteins gag, pol and env; and
   c) a third inoculant comprising bupivacaine.

2. A pharmaceutical composition comprising:
   a) a compound selected from the group consisting of: bupivacaine, mepivacaine, lidocaine, procaine, carbocaine and methyl bupivacaine; and
   b) a DNA molecule that comprises a DNA sequence that encodes an antigen; wherein said DNA sequence operatively linked to regulatory sequences which control the expression of said DNA sequence.

3. The pharmaceutical composition of claim 2 wherein said composition comprises bupivacaine.

4. The pharmaceutical composition of claim 2 wherein said DNA molecule is a plasmid.

5. The pharmaceutical composition of claim 2 wherein said DNA sequence encodes a variable region of a T cell receptor.

6. The pharmaceutical composition of claim 2 wherein said DNA sequence encodes a pathogen antigen.

7. The pharmaceutical composition of claim 6 wherein said DNA sequence encodes an antigen from an intracellular pathogen.

8. The pharmaceutical composition of claim 7 wherein said antigen is a viral antigen.

9. The pharmaceutical composition of claim 8 wherein said pathogen is a virus selected from the group consisting of: human immunodeficiency virus, HIV; human T cell leukemia virus, HTLV; influenza virus; hepatitis A virus; hepatitis B virus; hepatitis C virus; human papilloma virus, HPV; Herpes simplex 1 virus, HSV1; Herpes simplex 2 virus, HSV2; Cytomegalovirus, CMV; Epstein-Barr virus, EBR; rhinovirus; and, coronavirus.

10. The pharmaceutical composition of claim 9 wherein said pathogen is Herpes simplex 2 virus, HSV2.

11. The pharmaceutical composition of claim 9 wherein said pathogen is Hepatitis B virus, HBV.

12. The pharmaceutical composition of claim 9 wherein said pathogen is human T cell leukemia virus, HTLV.

13. The pharmaceutical composition of claim 9 wherein said pathogen is a human immunodeficiency virus.

14. The pharmaceutical composition of claim 2 wherein said DNA sequence encodes a hyperproliferative disease associated protein.

15. The pharmaceutical composition of claim 13 wherein said hyperproliferative disease is cancer.

16. The pharmaceutical composition of claim 14 wherein said hyperproliferative disease is a lymphoma.

17. The pharmaceutical composition of claim 14 wherein said hyperproliferative disease is a melanoma.

18. a method of immunizing an individual against an antigen comprising administering to tissue of said individual's body,
   a) a compound selected from the group consisting of bupivacaine, mepivacaine, lidocaine, procaine, carbocaine and methyl bupivacaine, and
   b) a DNA molecule that comprises a DNA sequence that encodes said antigen, said DNA sequence operatively linked to regulatory sequences which control the expression of said DNA sequence;
wherein said DNA molecule is taken up by cells, said DNA sequence is expressed in said cells and an immune response is generated against said antigen.

19. The method of claim 18 wherein said compound is bupivacaine.

20. The method of claim 18 wherein said DNA molecule is a plasmid.

21. The method of claim 18 wherein said immune response generated against said antigen is an immune response against a pathogen antigen.

22. The method of claim 21 wherein said pathogen is an intracellular pathogen.

23. The method of claim 22 wherein said pathogen is a virus selected from the group consisting of: human immunodeficiency virus, HIV; human T cell leukemia virus, HTLV; influenza virus; hepatitis a virus; hepatitis B virus; hepatitis C virus; human papilloma virus, HPV; Herpes simplex 1 virus, HSV1; Herpes simplex 2 virus, HSV2; Cytomegalovirus, CMV; Epstein-Barr virus, EBR; rhinovirus; and, coronavirus.

24. The method of claim 23 wherein said pathogen is HIV and said DNA molecule comprises a DNA sequence that encodes an HIV antigen.

25. The method of claim 18 wherein said immune response generated against said antigen is an immune response against a hyperproliferative disease-associated protein.

26. The method of claim 25 wherein said hyperproliferative disease-associated protein is selected from the group consisting of: protein products of oncogenes myb, myc, fyn, ras, src, neu and trk; protein products of translocation gene bcr/abl; P53; variable regions of antibodies made by B cell lymphomas; and variable regions of T cell receptors of T cell lymphomas.

27. The method of claim 18 wherein said immune response generated against said antigen is an immune response against an autoimmune disease-associated protein.

28. The method of claim 27 wherein said autoimmune disease-associated protein is selected from the group consisting of: variable regions of antibodies involved in B cell mediated autoimmune disease; and variable regions of T cell receptors involved in T cell mediated autoimmune disease.

29. The method of claim 18 wherein said bupivacaine and a DNA molecule are administered subcutaneously.

30. The method of claim 18 wherein said bupivacaine and a DNA molecule are administered intramuscularly, intraperitoneally, intravenously, intraarterially, intraoccularly, orally transdermally and/or by inhalation.

31. The method of claim 18 wherein said bupivacaine and a DNA molecule are administered intradermally.

32. The method of claim 31 wherein said immune response generated against said antigen is an immune response against a pathogen antigen.

33. The method of claim 31 wherein said immune response generated against said antigen is an immune response against a hyperproliferative disease-associated protein.

34. The method of claim 31 wherein said immune response generated against said antigen is an immune response against an autoimmune disease-associated protein.

* * * * *

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

AGGCGTCTCG AGACAGAGGA GAGCAAGAAA TG　　　　　　　　　　　　32

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

TTTCCCTCTA GATAAGCCAT CCAATCACAC　　　　　　　　　　　　　30

( 2 ) INFORMATION FOR SEQ ID NO:3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

GAAGGATCCA TGAAAAAATA TTTATTGGG　　　　　　　　　　　　　29

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

ACTGTCGACT TATTTTAAAG CGTTTTTAAG　　　　　　　　　　　　　30

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

GCCAGTTTTG GATCCTTAAA AAAGGCTTGG                                              30

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

TTGTGAGGGA CAGAATTCCA ATCAGGG                                                 27

( 2 ) INFORMATION FOR SEQ ID NO:7:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:7:

CAGTGATATC CCGGGAGACT CCTC                                                    24

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:8:

GAATAGAAGA ACTCCTCTAG AATTC                                                   25

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

GCCTTAGGCG GATCCTATGG CAGGAAG                                                 27

( 2 ) INFORMATION FOR SEQ ID NO:10:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

TAAGATGGGT GGCCATGGTG AATT                                                    24

( 2 ) INFORMATION FOR SEQ ID NO:11:

(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:11:

AGGCGTCTCG AGACAGAGGA GAGCAAGAAA TG     32

(2) INFORMATION FOR SEQ ID NO:12:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:12:

TTTCCCTCTA GATAAGCCAT CCAATCACAC     30

(2) INFORMATION FOR SEQ ID NO:13:

(i) SEQUENCE CHARACTERISTICS:
(A) LENGTH: 22 amino acids
(B) TYPE: amino acid
(D) TOPOLOGY: linear (ii) MOLECULE TYPE: peptide (xi) SEQUENCE DESCRIPTION: SEQ ID NO:13:

Cys Asn Thr Arg Lys Arg Ile Arg Ile Gln Arg Gly Pro Gly Arg Ala
 1               5                  10                 15
Phe Val Thr Ile Gly Lys
             20

(2) INFORMATION FOR SEQ ID NO:14:

(i) SEQUENCE CHARACTERISTICS:
(A) LENGTH: 25 amino acids
(B) TYPE: amino acid
(D) TOPOLOGY: linear (ii) MOLECULE TYPE: peptide (xi) SEQUENCE DESCRIPTION: SEQ ID NO:14:

Tyr Asn Lys Arg Lys Arg Ile His Ile Gln Arg Gly Pro Gly Arg Ala
 1               5                  10                 15
Phe Tyr Thr Thr Lys Asn Ile Ile Cys
             20                  25

(2) INFORMATION FOR SEQ ID NO:15:

(i) SEQUENCE CHARACTERISTICS:
(A) LENGTH: 27 amino acids
(B) TYPE: amino acid
(D) TOPOLOGY: linear (ii) MOLECULE TYPE: peptide (xi) SEQUENCE DESCRIPTION: SEQ ID NO:15:

Cys Arg Ile Lys Gln Phe Ile Asn Met Trp Gln Glu Val Gly Lys Ala
 1               5                  10                 15
Met Thr Ala Pro Pro Ile Ser Gly Ile Arg Cys
             20                  25

( 2 ) INFORMATION FOR SEQ ID NO:16:

( i ) SEQUENCE CHARACTERISTICS:
           ( A ) LENGTH: 26 amino acids
           ( B ) TYPE: amino acid
           ( D ) TOPOLOGY: linear ( i i ) MOLECULE TYPE: peptide ( x i ) SEQUENCE DESCRIPTION: SEQ ID NO:16:

```
Arg Ile Leu Ala Val Glu Arg Tyr Ile Lys Asp Gln Gln Leu Leu Gly Ile
 1               5                  10                  15
Trp Gly Cys Ser Gly Lys Leu Ile Cys
            20                  25
```

( 2 ) INFORMATION FOR SEQ ID NO:17:

( i ) SEQUENCE CHARACTERISTICS:
           ( A ) LENGTH: 27 base pairs
           ( B ) TYPE: nucleic acid
           ( C ) STRANDEDNESS: single
           ( D ) TOPOLOGY: linear ( i i ) MOLECULE TYPE: DNA ( x i ) SEQUENCE DESCRIPTION: SEQ ID NO:17:

TTGTTTAACT TTTGATCGAT CCATTCC          27

( 2 ) INFORMATION FOR SEQ ID NO:18:

( i ) SEQUENCE CHARACTERISTICS:
           ( A ) LENGTH: 21 base pairs
           ( B ) TYPE: nucleic acid
           ( C ) STRANDEDNESS: single
           ( D ) TOPOLOGY: linear ( i i ) MOLECULE TYPE: DNA ( x i ) SEQUENCE DESCRIPTION: SEQ ID NO:18:

GATTTGTATC GATGATCTGA C          21

( 2 ) INFORMATION FOR SEQ ID NO:19:

( i ) SEQUENCE CHARACTERISTICS:
           ( A ) LENGTH: 25 base pairs
           ( B ) TYPE: nucleic acid
           ( C ) STRANDEDNESS: single
           ( D ) TOPOLOGY: linear ( i i ) MOLECULE TYPE: DNA ( x i ) SEQUENCE DESCRIPTION: SEQ ID NO:19:

TGTAGTAGCA AAAGAAATAG TTAAG          25

( 2 ) INFORMATION FOR SEQ ID NO:20:

( i ) SEQUENCE CHARACTERISTICS:
           ( A ) LENGTH: 25 base pairs
           ( B ) TYPE: nucleic acid
           ( C ) STRANDEDNESS: single
           ( D ) TOPOLOGY: linear ( i i ) MOLECULE TYPE: DNA ( x i ) SEQUENCE DESCRIPTION: SEQ ID NO:20:

AATTCTTAAC TATTTCTTTT GCTAC          25

(2) INFORMATION FOR SEQ ID NO:21:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

ATTTGTCGAC TGGTTTCAGC CTGCCATGGC AGGAAGAAGC     40

(2) INFORMATION FOR SEQ ID NO:22:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

ACGACGCGTA TTCTTTAGCT CCTGACTCC     29

(2) INFORMATION FOR SEQ ID NO:23:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

GCTGACGGTA GCGGCCGCAC AATT     24

(2) INFORMATION FOR SEQ ID NO:24:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

GTATTAAGCG GCCGCAATTG TT     22

(2) INFORMATION FOR SEQ ID NO:25:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

AAAAAGCTTC GCGGATCCGC GTTGCGGCCG CAACCGGTCA CCGGCGACGC GTCGGTCGAc     60

CGGTCATGGC TGGGCCCC     78

(2) INFORMATION FOR SEQ ID NO:26:

(i) SEQUENCE CHARACTERISTICS:

(A) LENGTH: 29 base pairs
    (B) TYPE: nucleic acid
    (C) STRANDEDNESS: single
    (D) TOPOLOGY: linear ( i i ) MOLECULE TYPE: DNA ( x i ) SEQUENCE DESCRIPTION: SEQ ID NO:26:

CCCAAGCTTA GACATGATAA GATACATTG 29

( 2 ) INFORMATION FOR SEQ ID NO:27:

( i ) SEQUENCE CHARACTERISTICS:
    (A) LENGTH: 22 base pairs
    (B) TYPE: nucleic acid
    (C) STRANDEDNESS: single
    (D) TOPOLOGY: linear ( i i ) MOLECULE TYPE: DNA ( x i ) SEQUENCE DESCRIPTION: SEQ ID NO:27:

CTAGCAGCTG GATCCCAGCT TC 22

( 2 ) INFORMATION FOR SEQ ID NO:28:

( i ) SEQUENCE CHARACTERISTICS:
    (A) LENGTH: 24 base pairs
    (B) TYPE: nucleic acid
    (C) STRANDEDNESS: single
    (D) TOPOLOGY: linear ( i i ) MOLECULE TYPE: DNA ( x i ) SEQUENCE DESCRIPTION: SEQ ID NO:28:

GGATTTCTGG GGATCCAAGC TAGT 24

( 2 ) INFORMATION FOR SEQ ID NO:29:

( i ) SEQUENCE CHARACTERISTICS:
    (A) LENGTH: 31 base pairs
    (B) TYPE: nucleic acid
    (C) STRANDEDNESS: single
    (D) TOPOLOGY: linear ( i i ) MOLECULE TYPE: DNA ( x i ) SEQUENCE DESCRIPTION: SEQ ID NO:29:

TATAGGATCC GCGCAATGAA AGACCCCACC T 31

( 2 ) INFORMATION FOR SEQ ID NO:30:

( i ) SEQUENCE CHARACTERISTICS:
    (A) LENGTH: 31 base pairs
    (B) TYPE: nucleic acid
    (C) STRANDEDNESS: single
    (D) TOPOLOGY: linear ( i i ) MOLECULE TYPE: DNA ( x i ) SEQUENCE DESCRIPTION: SEQ ID NO:30:

ATATGGATCC GCAATGAAAG ACCCCGCTG A 31

( 2 ) INFORMATION FOR SEQ ID NO:31:

( i ) SEQUENCE CHARACTERISTICS:
    (A) LENGTH: 30 base pairs
    (B) TYPE: nucleic acid
    (C) STRANDEDNESS: single
    (D) TOPOLOGY: linear

```
      (  i  i  ) MOLECULE TYPE: DNA (  x  i  ) SEQUENCE DESCRIPTION: SEQ ID NO:31:

TAAAGCGGCC    GCTCCTATGG    CAGGAAGACG                                          30
```

( 2 ) INFORMATION FOR SEQ ID NO:32:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:32:

```
ATTACGCGTC    TTATGCTTCT    AGCCAGGCAC    AATG                                  34
```

( 2 ) INFORMATION FOR SEQ ID NO:33:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:33:

```
ATTACGCGTT    TATTACAGAA    TGGAAAACAG    ATGGCAGGTG                            40
```

( 2 ) INFORMATION FOR SEQ ID NO:34:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:34:

```
ATTACGCGTT    ATTGCAGAAT    TCTTATTATG    GC                                    32
```